United States Patent
Wang et al.

(10) Patent No.: US 11,560,408 B2
(45) Date of Patent: Jan. 24, 2023

(54) CONJUGATED VIRUS-LIKE PARTICLES AND USES THEREOF AS ANTI-TUMOR IMMUNE REDIRECTORS

(71) Applicant: VERIMMUNE INC., Washington, DC (US)

(72) Inventors: Joshua Weiyuan Wang, Alexandria, VA (US); Nattha Ingavat, Bangkok (TH); Ken Matsui, Frederick, MD (US)

(73) Assignee: VERIMMUNE INC., Washington, DC (US)

( * ) Notice: Subject to any disclaimer, the term of this patent is extended or adjusted under 35 U.S.C. 154(b) by 0 days.

(21) Appl. No.: 16/727,781

(22) Filed: Dec. 26, 2019

(65) Prior Publication Data
US 2020/0291072 A1    Sep. 17, 2020

Related U.S. Application Data

(60) Provisional application No. 62/785,502, filed on Dec. 27, 2018.

(51) Int. Cl.
| | |
|---|---|
| *A61K 35/00* | (2006.01) |
| *C07K 14/005* | (2006.01) |
| *A61P 35/00* | (2006.01) |
| *A61K 35/76* | (2015.01) |
| *C12N 7/00* | (2006.01) |
| *G01N 33/50* | (2006.01) |

(52) U.S. Cl.
CPC ............ *C07K 14/005* (2013.01); *A61K 35/76* (2013.01); *A61P 35/00* (2018.01); *C12N 7/00* (2013.01); *G01N 33/5094* (2013.01); *C12N 2710/20022* (2013.01); *C12N 2710/20023* (2013.01); *C12N 2710/20033* (2013.01)

(58) Field of Classification Search
CPC ............ A61K 35/76; A61K 2039/5258; A61K 2039/545; A61K 2039/585; A61K 35/17; A61K 35/761; A61K 35/763; A61K 39/02; A61K 39/12; A61K 39/39; A61K 9/107; A61P 35/00; C07K 14/005; C12N 2710/20022; C12N 2710/20023; C12N 2710/20033; C12N 7/00; G01N 33/5094
See application file for complete search history.

(56) References Cited

U.S. PATENT DOCUMENTS

| | | | |
|---|---|---|---|
| 7,521,209 B2 * | 4/2009 | Brown ................ | C12P 21/06 435/344.1 |
| 8,062,642 B1 | 11/2011 | Rose et al. | |
| 8,168,190 B2 | 5/2012 | Murray | |
| 9,045,727 B2 | 6/2015 | Compans et al. | |
| 9,149,503 B2 | 10/2015 | Roden et al. | |
| 9,580,474 B2 | 2/2017 | Viscidi et al. | |
| 9,855,347 B2 | 1/2018 | De Los Pinos et al. | |
| 10,117,947 B2 | 11/2018 | De Los Pinos et al. | |
| 10,688,172 B2 | 6/2020 | Coursaget et al. | |
| 10,933,129 B2 | 3/2021 | Altreuter et al. | |
| 2002/0039584 A1 | 4/2002 | Hallek et al. | |
| 2004/0209295 A1 | 10/2004 | Schwabe et al. | |
| 2004/0223976 A1 | 11/2004 | Bianchi et al. | |
| 2005/0142115 A1 | 6/2005 | Qiao et al. | |
| 2007/0104689 A1 | 5/2007 | Gillies et al. | |
| 2007/0160628 A1 | 7/2007 | Birkett et al. | |
| 2007/0184473 A1 | 8/2007 | Shirwan et al. | |
| 2010/0092504 A1 | 4/2010 | Rose et al. | |
| 2010/0135902 A1 | 6/2010 | Roberts et al. | |
| 2010/0172936 A1 | 7/2010 | Lowy et al. | |
| 2010/0260792 A1 * | 10/2010 | Murata ................ | C07K 14/005 424/192.1 |

(Continued)

FOREIGN PATENT DOCUMENTS

| | | |
|---|---|---|
| CN | 102153656 A | 8/2011 |
| EP | 2416798 B1 | 9/2017 |

(Continued)

OTHER PUBLICATIONS

Vartak et al. Matrix metalloproteases: Underutilized targets for drug delivery. (J Drug Target. 2007; 15(1): 1-20). (Year: 2007).*
David G. Millar et al., "Anti-body mediated delivery of viral epitopes to tumors harnesses CMV-specific T cells for cancer therapy", Nature Biotechnology, 2020, pp. 1-6.
Andreas M. Kaufmann et al., "Vaccination trial with HPV16 L1E7 chimeric virus-like particles in women suffering from high grade cervical intraepithelial neoplasia (CIN 2/3)", International Journal of Cancer, 121(12), Dec. 2007, pp. 2794-2800.
PCT International Search Report and Written Opinion dated Mar. 10, 2020, International Application No. PCT/US2019/068619, pp. 1-24.

(Continued)

*Primary Examiner* — Aradhana Sasan
*Assistant Examiner* — Mercy H Sabila
(74) *Attorney, Agent, or Firm* — BioPharma Law Group, PLLC

(57) ABSTRACT

Disclosed is a new class of conjugated virus-like particles (VLPs). These conjugated VLPs bind a wide variety of tumors and comprise epitopes recognized by a prior T cell immune response already existing in a host. These epitopes are derived from pathogens or previous vaccinations (such as early childhood vaccines). This provokes the body's pre-existing cytotoxic immunity obtained through previous infection or previous childhood vaccination to be redirected to the tumor cells for the elimination of cancer, and form long-term anti-tumor immunity. The described conjugated VLPs are useful for tailoring a broad range of tumors towards a response from existing immunity circumventing the need to identify tumor antigens or generate tumor-specific immune responses. Importantly, the compositions and methods described herein broadens opportunities for treatment for all cancer types in subjects who previously had un-targetable cancers due to various technological and biological limitations of currently available immuno-therapeutic drugs.

19 Claims, 24 Drawing Sheets

Specification includes a Sequence Listing.

(56) References Cited

U.S. PATENT DOCUMENTS

| | | | |
|---|---|---|---|
| 2014/0050753 A1* | 2/2014 | Viscidi | A61K 47/6425 424/186.1 |
| 2014/0099337 A1 | 4/2014 | Davis et al. | |
| 2015/0231239 A1 | 8/2015 | Hung et al. | |
| 2016/0058852 A1 | 3/2016 | Ter Meulen et al. | |
| 2017/0152316 A1 | 6/2017 | Cobbold | |
| 2017/0274099 A1 | 9/2017 | De Los Pinos et al. | |
| 2017/0327543 A1 | 11/2017 | Viscidi et al. | |
| 2018/0078655 A1 | 3/2018 | Dziadek et al. | |
| 2018/0104320 A1 | 4/2018 | Gravekamp | |
| 2018/0110883 A1 | 4/2018 | De Los Pinos et al. | |
| 2018/0193382 A1 | 7/2018 | Barrat | |
| 2018/0311269 A1 | 11/2018 | Lobb et al. | |
| 2018/0311374 A1* | 11/2018 | Lobb | A61K 9/0019 |
| 2018/0325952 A1 | 11/2018 | Masopust, Jr. et al. | |
| 2019/0022206 A1 | 1/2019 | Pedersen et al. | |
| 2019/0117760 A1 | 4/2019 | Graham et al. | |
| 2020/0121779 A1 | 4/2020 | Garcea et al. | |
| 2020/0164054 A1 | 5/2020 | Snyder et al. | |

FOREIGN PATENT DOCUMENTS

| | | |
|---|---|---|
| WO | 96/11274 A1 | 4/1996 |
| WO | 99/50424 A1 | 10/1999 |
| WO | 01/23422 A1 | 4/2001 |
| WO | 2009055491 A2 | 4/2009 |
| WO | 2010/001409 A2 | 1/2010 |
| WO | 2010/118424 A2 | 10/2010 |
| WO | 2012/033911 A2 | 3/2012 |
| WO | 2012/123755 A1 | 9/2012 |
| WO | 2013080187 A1 | 6/2013 |
| WO | 2014043523 A1 | 3/2014 |
| WO | 2014145932 A1 | 9/2014 |
| WO | 2016112921 A1 | 7/2016 |
| WO | 2016176164 A1 | 11/2016 |
| WO | 201720570 A1 | 2/2017 |
| WO | 2017/075615 A1 | 5/2017 |
| WO | 2017/079747 A1 | 5/2017 |
| WO | 2017087789 A1 | 5/2017 |
| WO | 2017/112830 A1 | 6/2017 |
| WO | 2017/177204 A1 | 10/2017 |
| WO | 2018/106972 A1 | 6/2018 |
| WO | 2018/237115 A2 | 12/2018 |
| WO | 2019/028406 A1 | 2/2019 |
| WO | 2019/090304 A1 | 5/2019 |
| WO | 2020017962 A1 | 1/2020 |
| WO | 2020198344 A1 | 10/2020 |

OTHER PUBLICATIONS

Xiaojiang S. Chen et al., "Structure of Small Virus-like Particles Assembled from the L1 Protein of Human Papillomavirus 16", Molecular Cell, vol. 5, Mar. 2000, pp. 557-567.

Jeffrey I. Cohen, "Epstein-barr virus vaccines", Clinical & Transitional Immunology, vol. 4, No. 4, 2015, pp. 1-6.

Christopher P. Fox et al., "A novel latent membrane 2 transcript expressed in Epstein-Barr virus-positive NK- and T-cell lymphoproliferative disease encodes a target for cellular immunotherapy", Blood Journal, vol. 116, No. 19, Nov. 11, 2010, pp. 3695-3704.

Gregson et al., "Phase I trail of an alhydrogel adjuvanted hepatitis B core virus-like particle containing epitopes of Plasmodium falciparum circumsporozoite protein", PLoS One, 3(2), Feb. 6, 2008, p. e1556 (Abstract Submitted).

PCT International Search Report and Written Opinion dated Dec. 12, 2018, International Application No. PCT/US2018/038701, pp. 1-19.

Wen Jun Liu et al., "Papillomavirus Virus-like Particles for the Delivery of Multiple Cytotoxic T Cell Epitopes", Virology, vol. 273, 2000, pp. 374-382.

Slavica Matic et al., "Efficient production of chimeric Human papillomavirus 16 L1 protein bearing the M2e influenza epitope in Nicotiana benthamiana plants", BMC Biotechnology, 11:106, 2011, pp. 1-12.

Cuburu Nicolas et al., "Harnessing pre-existing anti-viral immunity for tumor therapy", SITC 2019, Retrieved from the Internet on Nov. 11, 2019: www. sitcancer.org, pp. 920-921.

Sharmila Pejawar-Gaddy et al., "All in one: VLP-MUC1 vaccine for prevention and treatment of epithelial tumors", The FASEB Journal, vol. 22, No. 1_supplement, Mar. 2008, pp. 1077-7 (Abstract Submitted).

John T. Schiller et al., "Papillomavirus-like particle based vaccines: cervical cancer and beyond", Expert Opinion on Biological Therapy, vol. 1, No. 4, Aug. 2001, pp. 571-581.

Julian P. Sefrin et al., "Sensitization of Tumors for Attack by Virus-Specific CD8+ T-Cells Through Antibody-Mediated Delivery of Immunogenic T-Cell Epitopes", Frontiers in Immunology, vol. 10, Article 1962, Aug. 2019, pp. 1-14.

Katharina Slupetzky et al., "Chimeric papillomavirus-like particles expressing a foreign epitope on capsid surface loops", Journal of General Virology, vol. 82, Issue 11, Nov. 2001, pp. 2799-2804.

Susan Thrane et al., "A Novel Virus-like Particle Based Vaccine Platform Displaying the Placental Malaria Antigen VAR2CSA", PLoS One, 10(11), Nov. 23, 2015, pp. 1-16.

S. Kirk Wright et al., "Evaluation of methods for the quantitation of cysteines in proteins", Analytical Biochemistry, vol. 265, Issue 1, Dec. 1, 1998, pp. 8-14 (Abstract Submitted).

Deepali G. Vartak et al., "Matrix metalloproteases: Underutilized targets for drug delivery," Journal of Drug Targeting, Jan. 2007, 15(1), pp. 1-20.

Marion Braun et al., "Virus-like particles induce robust human T-helper cell responses," European Journal of Immunology, 2012, 42: pp. 330-340.

Extended European Search Report dated Mar. 18, 2021, European Application No. 18820136.2, pp. 1-7.

Stefania Bellone et al., "Human Papillomavirus Type 16 (HPV-16) Virus-Like Particle L1-Specific CD8+ Cytotoxic T Lymphocytes (CTLs) Are Equally Effective as E7-Specific CD8+ CTLs in Killing Autologous HPV-16-Positive Tumor Cells in Cervical Cancer Patients: Implications for L1 Dendritic Cell-Based Therapeutic Vaccines," Journal of Virology, vol. 83, No. 13, Jul. 2009, pp. 6779-6789.

R. Kirnbauer et al., "Virus-like Particles of Bovine Papillomavirus Type 4 in Prophylactic and Therapeutic Immunization," Virology, vol. 219, Article 0220, 1996, pp. 37-44.

Eurasian Office Action dated Mar. 24, 2022, Eurasian Patent Application No. 202090030, pp. 1-3 (English Translation of Original Office Action).

Huber, B., et al., "Chimeric L2-based virus-like particle (VLP) vaccines targeting cutaneous human papillomaviruses (HPV).", PLOS One, Jan. 5, 2017, vol. 12, No. 1, e0169533, pp. 1-27.

Plummer, E.M., et al., "Viral nanoparticles and virus-like particles: platforms for contemporary vaccine design.", Wires Nanomedicine and Nano Biotechnology, Sep. 24, 2010, vol. 3, No. 2, pp. 174-196.

JPO Notice of Reasons for Rejection dated Jun. 28, 2022, Japanese Application No. 2020-520192, pp. 1-9.

\* cited by examiner

CONJUGATED VIRUS-LIKE PARTICLES AND USES THEREOF AS ANTI-TUMOR IMMUNE REDIRECTORS

PRIORITY

This application claims priority to, and the benefit of, U.S. Provisional Patent Application Ser. No. 62/785,502, filed Dec. 27, 2018, which is hereby incorporated by reference in its entirety.

REFERENCE TO SEQUENCE LISTING SUBMITTED VIA EFS-WEB

Pursuant to the EFS-Web legal framework and 37 CFR §§ 1.821-825 (see MPEP § 2442.03(a)), a Sequence Listing in the form of an ASCII-compliant text file (entitled "8002PCT_ST25.txt" created on Dec. 26, 2019, and 28,572 bytes in size) is submitted concurrently with the instant application, and the entire contents of the Sequence Listing are incorporated herein by reference in its entirety.

FIELD OF THE INVENTION

The invention relates to conjugated virus-like particles (VLPs) that preferentially bind tumors. The VLPs of the invention include a recall protein capable of eliciting a T cell response using preexisting recall protein-specific T cells that selectively attack the tumor to which the VLP is bound.

BACKGROUND

According to the National Cancer Institute, the overall rate of cancer deaths continue to decrease: the overall cancer incidence rates have declined in men and have stabilized in women. The five-year survival has also improved for most but not all common cancers. And yet it is estimated that in 2017 there will be an additional 1,688,780 new cancer cases diagnosed and 600,920 cancer deaths in the US alone. Typical cancer treatment includes chemotherapy, radiation, and surgery. However, surgery is highly invasive and often fails-especially after metastasis. Chemotherapy and radiation can be effective, but result in harsh side-effects that drastically reduce quality of life. Despite these treatments, many cancers remain refractory to treatment and the treatments can be ineffective in combating metastatic cancers even when successful in reducing or eliminating the primary tumor. Targeted delivery has become one of the most promising, but also most challenging, opportunities for improving the treatment of these diseases. The first attempts at developing delivery vehicles were antibody-drug conjugates. In almost all cases, the goal is to deliver cytotoxic T cells (CTLs) to the site of cancer cells to achieve selective killing of cancer cells. More recently, attempts have been made to use such immunotherapy to stimulate the immune system and specifically target proteins preferentially present on the surface of the cancer cell, resulting in targeted elimination of the cancer cells. Such therapies are attractive in that they are target specific, and potentially less toxic without nonspecific autoimmunity. They are also considered less invasive or traumatic compared to surgery, radiation or chemotherapy. However, cancer vaccines based on cancer-associated antigens can have limited success due to poor clinical immunogenicity, immune tolerance, and off target effects, for example. Moreover, such methods typically require identifying a cancer-associated antigen specific to a given patient's cancer to achieve effective targeting of the cancer. Hence, this approach has failed on multiple occasions because most cancer-associated antigens are self-antigens that are tolerated by the immune system, resulting in poor immune responses. Importantly, successes demonstrated by these specific cancer antigen-specific immunotherapeutics in gold standard animal models have not been always translatable to humans. Last but not least, not all the patients suffering from cancer will express the same antigens on tumors, thus there is a limitation with respect to broad applicability. Recently, this field has now switched to focusing on individual tumor mutations within a patient which might result in a cancer-specific neoepitopes. Using these neoepitopes as antigens, termed "neo-antigens" has revived the cancer vaccine space. However, this is a highly personalized therapy that involves a lengthy development time that is both costly and difficult for widespread implementation. Similar limitations are also seen in conjugated antigen receptor T cell-based (CAR-T cell) strategies although curative One class of therapeutics, which has been gaining favor is the immune checkpoint blockade therapies. This mode of treatment is based on the premise that tumor growth and progression is driven by the its ability to prevent specific targeting and destruction by the immune system. In light of this, checkpoint inhibition therapies act to reverse such "immune-suppression", thereby reinitiating proper and effective antitumor function of the immune system. Indeed, these therapies have shown significant benefit for a variety of cancers (melanoma, colorectal cancer) that previously had very poor prognosis. However, it is well established that the tumor microenvironment dampens the ability of endogenous anti-tumor immune cells to eradicate cancers. As such, drugs that target the checkpoint pathway members programmed cell death-1 (PD-1) or programmed death ligand 1 (PD-L1) work to block immunosuppressive pathways, and have been shown to assist the body's immune system in fighting cancer. Unfortunately, checkpoint inhibitor drugs do not work in the majority of patients, with a dismal 70% non-responder rate. This is primarily due to the lack of a pre-existing anti-tumor CD8+ T cell immune response that can infiltrate the tumor. Hence, checkpoint inhibitors are generally considered ineffective in treating cancers that frequently lack a significant anti-tumor immune infiltrate (also sometimes known as "cold tumors" or "non-immunogenic"), especially during early phases of development when the tumor develops at the site of origin.

As a result of this, current treatments retain the same recognized limitations of toxicity, limited responder population (not applicable to a broad variety of cancers) and most importantly, they also possess a cost-prohibitive development pathway resulting in higher medical costs for the patient. It is therefore important to consider an alternative immunotherapeutic strategy that can circumvent the issues of immune tolerance as well as lack of immune infiltrates and thus there remains a need for compositions and methods that produce strong, durable, cancer-specific T cell responses to inhibit tumor growth, progression, and metastasis without undue characterization of individual patient cancer types.

SUMMARY OF THE INVENTION

In various embodiments a conjugated Virus Like Particle ("VLP") is provided wherein the VLP comprises a capsid protein, wherein said capsid protein is capable of binding, or binds to, a cancer cell; and a fusion protein comprising at least a protein cleavage sequence, wherein the protein cleavage sequence is preferentially cleaved in the presence of a tumor; and at least one recall protein, wherein said recall protein is a protein or fragment thereof having a sequence that is an epitope capable of being bound by, or is bound by, an existing T cell in a patient.

In various embodiments, the capsid protein is from a papillomavirus. In various embodiments, the papillomavirus comprises an L1 protein. In various embodiments, the recall protein comprises the epitope of a pathogen. In various embodiments, the VLP comprises at least one fusion protein comprising at least two recall proteins. In various embodiments, the VLP comprises at least two fusion proteins each comprising a distinct recall protein. In various embodiments, at least two of the recall proteins are proteins or fragments thereof having a sequence from different T cell epitopes from the same pathogen. In various embodiments, at least two of the recall proteins are proteins or fragments thereof having the sequence from different T cell epitopes for different pathogens.

In various embodiments, the pathogen is a virus, a bacterium, a fungus, or a parasite. In various embodiments the epitope is derived from, or comprised of a sequence or subset of the sequence of, an epitope of a human vaccine. In various embodiments the vaccine is an early childhood vaccine or a vaccine approved for adults. In various embodiments, the fusion protein is conjugated to a cysteine, a lysine, or an arginine of the capsid protein via a disulfide linkage, a maleimide lineage, or an amide linkage. In various embodiments, the capsid protein and the fusion protein are expressed contiguously as a fusion protein. In various embodiments, the vaccine is a vaccine for a pathogen. In various embodiments, the pathogen is a virus, a bacterium, a fungus, or a parasite. In various embodiments, the vaccine elicits immunity to a vaccinia virus, varicella zoster virus, a Herpes zoster virus, rubella, a hepatitis virus, e.g., hepatitis A virus, or hepatitis B virus, or hepatitis C virus, an influenza virus type A or type B, a measles virus, a mumps virus, a poliovirus, a variola (smallpox) virus, a rabies virus, dengue virus, Ebola virus, West Nile virus, a yellow fever virus, or a zika virus, or cytomegalovirus, or Epstein-Barr virus. In various embodiments the vaccine elicits an immunity to a bacterial infection, and wherein the bacterium is *Bordetella pertussis, Clostridium tetani, Chlamydia trachomatis*, diphtheria, *Hemophilus influenza, Meningococcus*, e.g., Meningococcal ACWY, *Pneumococcus, Vibrio cholera, Mycobacterium tuberculosis*, Bacille Calmette Guerin (BCG), typhoid, *E. coli, Salmonella, Legionella pneumophila, Rickettsia, Treponema pallidum pallidum, Streptococcus* group A or group B, *Streptococcus pneumonia, Bacillus anthracis, Clostridium botulinum*, or *Yersinia* sp. In various embodiments, the parasite is *Entamoeba histolytica, Toxoplasma gondii*, a *Trichinella* sp., e.g., *Trichinella spiralis*, a *Trichomonas* sp., e.g., *Trichomonas vaginalis*, a *Trypanosoma* sp., e.g., *Trypanosoma brucei gambiense, Trypanosoma brucei rhodesiense*, or a *Trypanosoma cruzi*, or a *Plasmodium*, e.g., *Plasmodium falciparum, Plasmodium vivax*, or *Plasmodium malariae*.

In various embodiments, the VLP is capable of eliciting a T cell response of a threshold of at least 2-fold above baseline of total CD8+ T cells. In various embodiments, the CD8+ T cells are also CD69+. In various embodiments, the CD8+ T cells are also CD69+CD103+. In various embodiments, the CD8+ T cells are Tissue Resident Memory T cells (TRM cells) originating from non-lymphoid organs. In various embodiments the capsid protein is capable of selectively binding a heparin sulfate proteoglycan ("HSPG").

In various embodiments, a method is provided for treating a subject with a cancer, comprising administering a conjugated virus-like particle (VLP), wherein the VLP comprises: (a) a capsid protein, wherein said capsid protein is capable of binding a cancer cell; and (b) a fusion protein comprising at least: i) a cleavage sequence, wherein the cleavage sequence is preferentially cleaved in the presence of a tumor; and ii) at least one recall protein, wherein said recall protein is a protein or fragment thereof having a sequence that is an epitope capable of being bound by an existing T cell in a patient wherein the cleavage sequence is bound to the capsid protein. In various embodiments the method further comprises a second administration of the recall protein. In various embodiments, the second administration of the recall protein is delivered as a conjugated VLP. In various embodiments, the second administration of the recall protein is delivered as a vaccine. In various embodiments, the second administration of the recall protein is delivered as an isolated peptide in an adjuvant.

In various embodiments a method is provided for providing a conjugated virus-like particle (VLP) to a patient in need thereof, comprising: (i) measuring preexisting immunity in a patient; and (ii) selecting an appropriate conjugated VLP for administration to a patient in need thereof, said VLP comprising: (a) a capsid protein, wherein said capsid protein is capable of binding a cancer cell; and (b) a fusion protein comprising at least: i) a cleavage sequence, wherein the cleavage sequence is preferentially cleaved in the presence of a tumor; and ii) at least one recall protein, wherein said recall protein is a protein or fragment thereof having a sequence that is an epitope capable of being bound by an existing T cell in a patient, wherein the cleavage sequence is bound to the capsid protein; wherein the T cell epitope can elicit a T cell the baseline of total CD8+ CD69+ positive T cells.

In various embodiments, a boosting vaccine is delivered to a patient. In various embodiments, the boosting vaccine is delivered at least two weeks following the administration of the conjugated VLP. In various embodiments, the boosting vaccine is delivered two weeks before the administration of the conjugated VLP. In various embodiments, the vaccine is shingles vaccine, a PREVNAR13® vaccine, a HEPLISAV-B® vaccine, an MMR-II vaccine, ZOSTAVAX®, or ENGERIX-B®. In various embodiments the vaccine is for shingles. In various embodiments, the vaccine is PREVNAR13®. In various embodiments, the vaccine is HEPLISAV-B®. In various embodiments the subject is a human patient at least 50 years old. In various embodiments, the patient was previously treated with a CAR-T, therapeutic vaccine, check point inhibitor, oncolytic virus, neo-antigen vaccine, neo-adjuvant, chemo-therapy, radiation, surgery, but was previously not shown to have an anti-tumor effect. In various embodiments, the recall protein is not a tumor associated antigen. In various embodiments, the method inhibits the growth, progression or metastasis of a tumor.

In various embodiments, the tumor is a small lung cell cancer, hepatocellular carcinoma, liver cancer, hepatocellular carcinoma, melanoma, metastatic melanoma, adrenal cancer, anal cancer, aplastic anemia, bile duct cancer, bladder cancer, bone cancer, brain or central nervous system (CNS) cancer, breast cancer, cancer of unknown primary origin, Castleman disease, cervical cancer, colon/rectum cancer, endometrial cancer, esophagus cancer, Ewing family of tumors, eye cancer, gallbladder cancer, gastrointestinal carcinoid tumors, gastrointestinal stromal tumor (GIST), gestational trophoblastic disease, Hodgkin disease, Kaposi sarcoma, kidney cancer, laryngeal and hypopharyngeal cancer, leukemia, liver cancer, lung cancer, lymphoma, malignant mesothelioma, multiple myeloma, myelodysplastic syndrome, nasal cavity and paranasal sinus cancer, nasopharyngeal cancer. neuroblastoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma, skin cancer, stomach cancer, testicular cancer, thymus cancer, thyroid cancer, uterine sarcoma, vaginal cancer. vulvar cancer, Waldenstrom macroglobulinemia, Wilms tumor, non-Hodgkin lymphoma, Hodgkin lymphoma, Burkitt's lymphoma, lymphoblastic lymphomas, mantle cell lymphoma (MCL), multiple myeloma (MM), small lymphocytic lymphoma (SLL), splenic marginal zone lymphoma, marginal zone lymphoma (extra-nodal or nodal), mixed cell type diffuse aggressive lymphomas of adults, large cell type diffuse aggressive lymphomas of adults, large cell immunoblastic diffuse aggressive lymphomas of adults, small non-cleaved cell diffuse aggressive lymphomas of adults, or follicular lymphoma, head and neck cancer, endometrial or uterine carcinoma, non-small cell lung cancer, osteosarcoma, glioblastoma, or metastatic cancer. In one embodiment, the cancer is a breast cancer, a cervical cancer, an ovarian cancer, a pancreatic cancer, or melanoma,

BRIEF DESCRIPTION OF THE DRAWINGS

FIG. 3 illustrates the E7 T cell-mediated cytotoxic effects of HPV16 E7 conjugated VLP in a B16 luciferase and ID8 luciferase tumor cell model in vitro in a time dependent manner. Particularly.

FIG. 4 illustrates the E7 T cell-mediated cytotoxic effects of HPV16 E7 conjugated VLP in a B16 luciferase and ID8 luciferase tumor cell model in vitro in a time dependent manner. Particularly, FIG.

FIG. 5 illustrates batch consistency of E7 T cell-mediated cytotoxic effects of HPV16 E7 conjugated VLP (batches F1-F3) on B16 luciferase and ID8 luciferase cells after two separate studies ending at 23 hrs and 23.5 hrs time points, respectively.

FIG. 6 illustrates batch consistency of E7 T cell-mediated cytotoxic effects of HPV16 E7-conjugated VLP on MC38 cells after two separate studies ending at 23 or 23.5 hrs, time points respectively. For three different batches of conjugated E7-conjugated VLPs.

FIG. 8 illustrates the in vivo efficacy of E7-conjugated VLP anti-tumor immune redirection in B16.F10 mice possessing an acute immune response, i.e. mice were treated 2 weeks post peptide RAHYNIVTF (SEQ ID NO: 1) vaccination, to the HPV16 E7 peptide RAHYNIVTF (SEQ ID NO: 1), by assessment of tumor volume.

FIG. 9 shows SIINFEKL/K$^b$ (SEQ ID NO: 2) FACS analysis of mouse tumor cells incubated in vitro with OVA-conjugated VLP.

Figure 1:
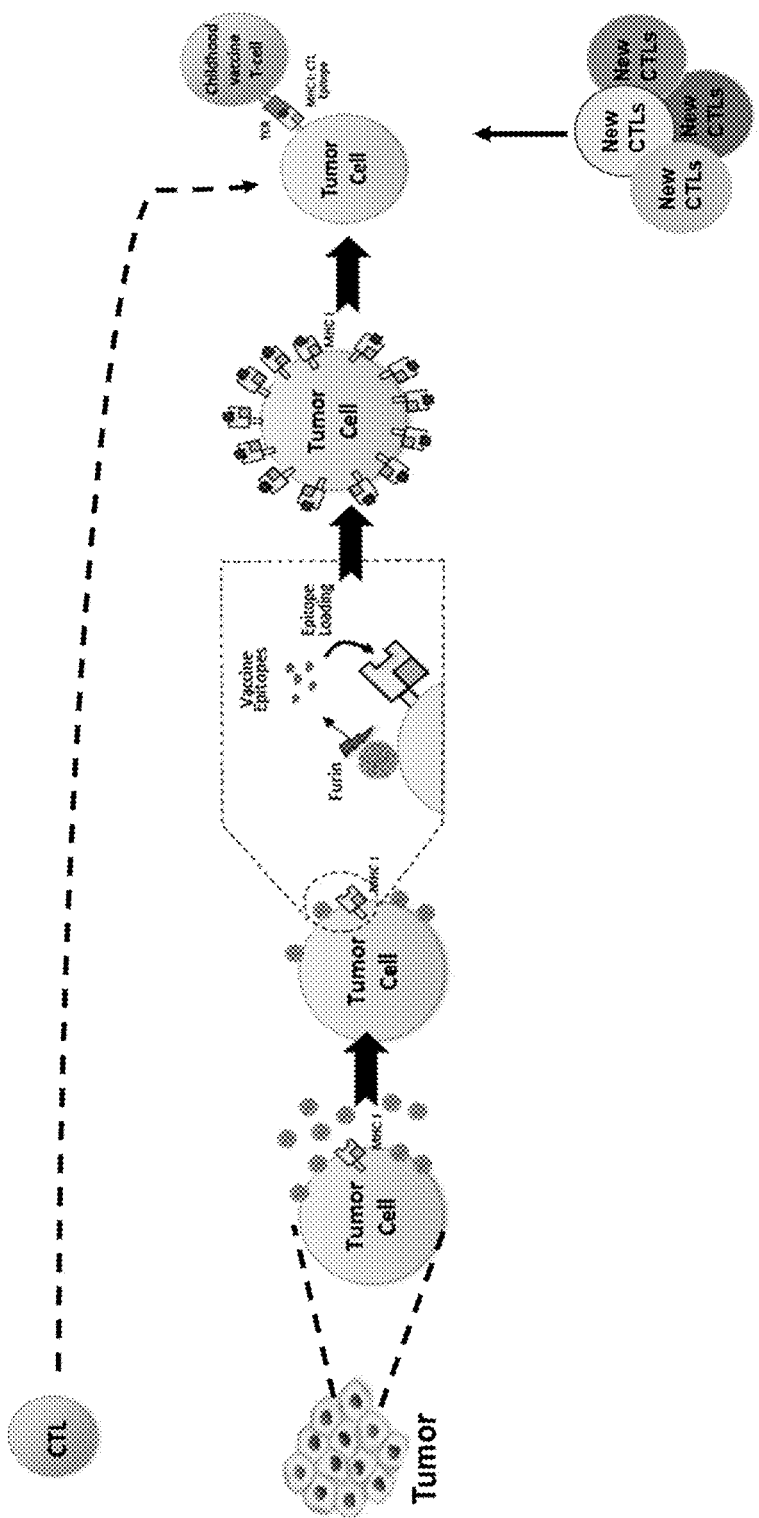
FIG. 1 illustrates the mechanism of action of the disclosed conjugated VLPs.

"MHC" or "major histocompatibility complex" is a group of genes that code for proteins found on the surfaces of cells that help the immune system recognize foreign substances. MHC proteins are found in all higher vertebrates. There are two main types of MHC molecules, MHC class I and MHC class II. In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-A*11 are examples of different MHC class I alleles that can be expressed from these loci.

"Papillomavirus" refers to all members of the papillomavirus family (Papillomaviridae). An extensive list of papillomavirus types and the ability to make the respective VLPs can be referenced using this publication: "Classification of papillomaviruses (PVs) based on 189 PV types and proposal of taxonomic amendments," de Villers et al., 401(1):70-79, 2010, PMID: 20206957 (all the tables).

"Preferentially cleaved protein" as used herein means that the fusion protein is preferentially cleaved from the capsid protein at the site of a tumor. This preferential tumor-site cleavage may be due to: (1) the unique cleavage sequence on the fusion protein, and/or (2) the unique tumor microenvironment. For example, in one embodiment, the fusion protein comprises a cleavage sequence that is preferentially cleaved by the enzyme furin, which is known to be expressed in high concentrations in tumor cells.

"Protein," "polypeptide," and "peptide," as used herein, are not restricted to any particular number of amino acids; these terms are sometimes used interchangeably herein. The properties and amino acid sequences of the proteins of the invention, and of the nucleic acids encoding them, are well-known and can be determined routinely, as well as downloaded from various known databases. (See, e.g., the NCBI GenBank databases). Some sequences are provided herein. However, some sequence information is routinely updated (e.g. to correct mistakes in the previous entries), so updated (corrected) information about the proteins and nucleic acids encoding them is included in this application. Information provided in the sequence databases discussed herein is incorporated by reference.

"Recall protein" as used herein refers to a protein or fragment thereof derived from a vaccine or pathogen to which the patient or subject has been previously exposed, this previous exposure having resulted in durable T cells that recognize and are specific for the recall protein. A recall protein is distinguished from a tumor-specific antigen.

A "recall response" is an immune response in which an antigen-primed cytotoxic T cell, Th1 T cell, Th2 T cell, and/or B cells primed by a vaccine or other pathogen present in the patient binds the recall protein.

A "subject," or "subject in need thereof" as used herein, includes any animal that has a tumor/cancer or has had a tumor/cancer or has a precancerous medical condition or cell. Suitable subjects (patients) include laboratory animals, such as mouse, rat, rabbit, guinea pig, or pig, farm animals, such as cattle, sporting animals, such as dogs or horses, domesticated animals or pets, such as a horse, dog, or cat, nonhuman primates, and humans.

"T cell response" as used herein refers to the immune response elicited by T cells as they encounter antigens. Naïve mature T cells are activated upon encountering antigen presented by B cells, macrophages, and dendritic cells, and produce armed effector T cells. Effector T cells are either CD8+ T cells that differentiate into cytotoxic T cells, or CD4+ T cells that primarily induce the humoral immune response. The T cell immune response further generates immunological memory that gives protection from the subsequent challenge by the pathogen. In various embodiments, the T cell response is at a threshold of at least 2-fold above the baseline of total CD8+ T cells. In various embodiments, the CD8+ T cells are CD69+ as well.

"Therapeutic compositions" are compositions that are designed and administered to patients. Therapeutic compositions, e.g., therapeutic conjugated VLP-containing compositions, are used to treat benign or malignant tumors or patients/subjects at risk for such tumors. In some embodiments, the conjugated VLPs are administered to a subject who previously had a tumor and is currently apparently tumor/cancer free, in an effort to enhance the inhibition or the recurrence of the tumor/cancer.

"Virus-like particle" or "VLP" refers to a multi-protein structure comprised of viral structural proteins, such as envelop or capsid proteins that can self-assemble into a particle that resembles a virus but lacks the viral genetic material. VLPs are non-infectious and non-replicating, yet morphologically similar to viruses. The VLPs disclosed herein bind to or have an inherent tropism for tumor cells.

"VLP vaccine" refers to a formulation, which contains 1, 2, 3, 4, 5, or more conjugated VLPs described herein. In one embodiment, compositions comprising the conjugated VLP described herein are in a form that is administered to a subject in order to redirect immunity already existing in the subject and to thereby inhibit the proliferation, growth, and/or metastasis of a tumor in the subject. Typically, a VLP vaccine comprises a conventional saline or buffered aqueous solution medium in which the compositions described herein are suspended or dissolved, although administration of dry powder, for example by inhalation, and even formulation with an additional adjuvant, such as alum, is also contemplated. The composition of the present invention can be used to inhibit the proliferation, growth, and/or metastasis of a tumor. Upon introduction into a host, a conjugated VLP-containing composition of the invention (e.g., a VLP vaccine) is able to provoke an immune response including, but not limited to, the production of cytokines and/or the activation of cytotoxic T cells, antigen presenting cells, helper T cells, dendritic cells and/or other cellular responses.

Conjugated Virus-Like Particles

In various embodiments, disclosed are conjugated VLPs for treating cancer in a subject. In various embodiments, the compositions described herein comprise a capsid protein, wherein said capsid protein binds a cancer cell. In various embodiments the compositions described herein further comprise a fusion protein comprising at least: (1) a cleavage sequence, wherein the cleavage sequence is preferentially cleaved in the presence of a tumor; and (2) at least one recall protein, wherein said recall protein is a protein or fragment thereof having a sequence that is an epitope that is bound by an existing T cell in a patient. In various embodiments the cleavage sequence is bound to the capsid protein.

Capsid Proteins.

In various embodiments, a VLP is provided. VLPs are comprised of viral structural particles, i.e. capsid proteins that self-assemble into a particle that resembles a virus but lacks the viral genetic material of a virus. VLPs are excellent delivery molecules because they are non-infectious and can be re-engineered to specifically target or bind to tumor cells.

It has been reported that HPV capsids (VLP and pseudovirions (PsV)) have tumor tropism and directly bind and infect tumor cells, including, e.g., ovarian and lung cancer cells. In various embodiments the conjugated VLPs described herein preferentially bind to tumor cells, e.g., they bind more to tumor cells than to non-tumor cells, and the presence of conjugated VLPs may result in a positive pro-inflammatory tumor microenvironment that attracts infiltrating CD8+ T cells. At the same time, the VLPs may stimulate a response by adaptive memory T cells that resulted from a previous vaccination or infection and that recognize the recall protein's CD8+ T cell epitope. In various embodiments these strong responses are able to bypass immune tolerance, and render the tumor cells susceptible to this preexisting immunity thereby inhibiting the growth, progression and metastasis of the tumor.

Any VLP that preferentially binds to tumor cells relative to normal cells may be used with the present invention. In various embodiments, the VLP is an animal virus-based VLP. In various embodiments, the animal virus-based VLP is derived from HBVc or HPV. In various embodiments, the VLP is a bacteriophage-based VLP, such as MS2, QP, or P22. In various embodiments, the VLP is a plant virus-based VLP such as cowpea chlorotic mottle virus (CCMV) or cowpea mosaic virus (CPMV). In various embodiments, the VLP is a currently commercialized prophylactic VLP-based vaccine, including GlaxoSmithKline's ENGERIX® (hepatitis B virus) and CERVARIX® (human papillomavirus), and Merck and Co., Inc.'s RECOMBIVAX HB® (hepatitis B virus) and GARDASIL® (human papillomavirus). Other embodiments of the VLP include VLP-based vaccine candidates in clinical trials or preclinical evaluation, such as, influenza virus, parvovirus, and Norwalk virus. In various embodiments, the VLP is a hamster polyoma virus, *Macrobrachium rosenbergii nodavirus*, HBsAg, HCV, retrovirus, or an HBc.

In one embodiment, the VLP is comprised of structural proteins derived from a papillomavirus. The papillomavirus virion contains 72 pentamers (capsomeres) of L1 protein. The L1 protein is capable of self-assembly into capsid-like structures that are morphologically indistinguishable from native virions when expressed in eukaryotic cells. The L1 monomer contains 12 b-strands, 6 loops (BC, CD, DE, EF, FG, HI), and 5 helices (H1-H5). Most of the loops are highly exposed towards the outer surface of the capsid, attachment of a fusion protein to one of these loops, by, e.g., disulfide linkage, maleimide linkage, by "click" chemistry or by binding to a polyionic docking site, as described herein, in these areas will result in the recall protein being displayed on the outer surface of VLPs.

Papillomavirus VLPs.

In various embodiments, a conjugated VLP is provided comprising a papilloma (PV) L1 protein, or an PVL1 and PV L2 protein. The VLP in some embodiments comprises both papilloma L1 and L2 proteins.

In an embodiment, the conjugated papillomavirus VLP comprises an L1 capsid protein and a fusion protein. In other embodiments, the conjugated VLP comprises an L1 capsid protein, an L2 capsid protein, and a fusion protein. The L1 polypeptide can be full length L1 protein or an L1 polypeptide fragment. In specific embodiments, the full-length L1 protein or L1 polypeptide fragment is VLP assembly-competent; that is, the L1 polypeptide will self-assemble to form capsomeres that are competent for self-assembly into higher-order assemblies, thereby forming a VLP. In more specific embodiments, the VLPs comprise a fully assembled papillomavirus capsid, a structure of about 50 nm and composed of 72 capsomeres or 360 copies of L1 protein.

The L1 sequences are known for substantially all papillomavirus genotypes identified to date, and any of these L1 sequences or fragments are contemplated as being employed in the present compositions. Examples of L1 polypeptides include, without limitation, full-length L1 polypeptides, e.g., HPV16 L1 polypeptide, SEQ ID NO: L1 truncations that lack the native C-terminus, L1 truncations that lack the native N-terminus, and L1 truncations that lack an internal domain. The L1 protein may be for example a modified L1 protein, e.g., a modified HPV16 L1 protein wherein the HPV16 L2 amino acids 17-36 (RG1 epitope) are inserted within the DE-surface loop of HPV16 L1. (See, Schellenbacher et al., 2013, *J. Invest Dermatol;* 133(12):2706-2713; Slupetzky et al, 2007, *Vaccine,* 25:2001-2010; Kondo et al, 2008, *J. Med. Virol,* 80:841-6; Schellenbacher et al., 2009, *J. Virol.,* 83:10085-10095; and Caldeira et al., 2010. *Vaccine,* 28:4384-93).

The L2 polypeptide can be full-length L2 protein or an L2 polypeptide fragment. The L2 sequences are known for substantially all papillomavirus genotypes identified to date, and any of these L2 sequences or fragments can be employed in the present invention. Examples of L2 polypeptides include, without limitation, full-length L2 polypeptides, e.g., HPV16 L2 polypeptide, SEQ ID NO: L2 truncations that lack the native C-terminus, L2 truncations that lack the native N-terminus, and L2 truncations that lack an internal domain.

The papillomavirus VLPs can be formed using the L1 and optionally L2 polypeptides from any animal papillomavirus, or derivatives or fragments thereof. Thus, any known (or hereafter identified) L1 and optionally L2 sequences of human, bovine, equine, ovine, porcine, deer, canine, feline, rodent, rabbit, etc., papillomaviruses can be employed to prepare the VLPs or capsomeres of the present invention. (See de Villiers et al., *Virology,* 324:17-27, 2004, for a near complete listing of papillomavirus genotypes and their relatedness, incorporated herein by reference).

In various embodiments, the VLP is comprised of a papilloma virus (PV) L1 protein, or a PV L1 and PV L2 protein. Papillomaviruses are small, double-stranded, circular DNA tumor viruses. The papilloma virion shells contain the L1 major capsid protein and the L2 minor capsid proteins. Expression of the L1 protein alone or in combination with the L2 protein in eukaryotic or prokaryotic expression systems is known to result in the assembly of capsomeres and VLPs. As used herein, the term "capsomere" is intended to mean a pentameric assembly of papillomavirus L1 polypeptides, including full-length L1 protein or fragments thereof. Native L1 capsid proteins may self-assemble via intermolecular disulfide bonds to form pentamers (capsomeres).

The papillomavirus virion may contain 72 pentamers (capsomeres) of L1 protein. (See, Trus et al., *Nat. Struct. Biol.,* 4:413-420, 1997). The L1 protein is capable of self-assembly into capsid-like structures that are morphologically indistinguishable from native virions when expressed in eukaryotic cells. (See, Buck et al., *J. Virol.,* 5190-97, 2008; and Roy et al., *Hum. Vaccin.,* 5-12, 2008, both incorporated herein by reference). The L1 monomer contains about 12 strands, 6 loops (BC, CD, DE, EF, FG, HI), and 5 helices (H1-H5). Most of the loops are highly exposed towards the outer surface of the capsid, attachment of a fusion protein to one of these loops, by e.g., disulfide linkage, maleimide linkage, by "click" chemistry or by binding to a polyionic docking site, as described herein, in these areas will result in the fusion protein being displayed on the outer surface of VLPs.

In certain embodiments, the L1 and optionally L2 polypeptides that are used to form the VLPs are from a non-human papillomavirus or a human papillomavirus genotype other than HPV-6, HPV-11, HPV-16, and HPV-18. For example, the L1 and/or L2 proteins may be from HPV 1, 2, 3, 4, 5, 6, 8, 9, 15, 17, 23, 27, 31, 33, 35, 38, 39, 45, 51, 52, 58, 66, 68, 70, 76, or 92.

In various embodiments, the conjugated VLP presented herein bind to one or more cancer cells. This is in part due to the VLP's selectivity for proteins and/or molecules specific to tumor cells. In various embodiments, the VLP binds to heparin sulfate proteoglycan (HSPG), which is preferentially expressed on tumor cells. As used herein, "binding to a cancer cell" refers to the formation of non-covalent interactions between the capsid protein of the conjugated VLP and the tumor cell such that the conjugated VLP may come into close proximity to the tumor cell and the fusion protein may be cleaved from the VLP, and the recall protein may bind to the MHC receptor present on the tumor cell.

Animal Virus-Based VLPs.

In addition to the VLPs described elsewhere herein the VLP may be derived from a hepatitis B virus. The hepatitis B virus is comprised of an internal protein capsid and a lipid envelope containing other proteins. Two different VLPs can be produced from the virus, using either the core antigen that forms the internal capsid or the surface antigen that spontaneously combines with lipids to form nanoparticles (NP)s. The hepatitis B core (HBc) antigen is formed from 240 copies of a single protein. These proteins first form dimers, which then assemble with pentameric or pseudo-hexameric junctions in a T54 icosahedral geometry. The VLP has been produced using multiple technologies including *Escherichia coli* cytosolic accumulation and cell-free protein synthesis. The assembled VLPs are typically purified using size-exclusion chromatography or differential centrifugation. Individual coat proteins have been subsequently obtained by disassembling the VLPs with urea, which allows simultaneous cargo loading and VLP re-assembly.

Bacteriophage Virus-Based VLPs.

In various embodiments, the VLP is derived from a bacteriophage-based VLP. The three bacteriophages, MS2, Qb, and *Salmonella typhimurium* P22, all infect enterobacteria, most notably *E. coli*. Although all three are composed of only a nucleic acid-filled viral capsid, P22 differs greatly from MS2 and Qb. MS2 and Qb are composed of 90 homodimers and require a specific stem-loop hairpin secondary structure in their RNA genome to trigger VLP self-assembly by binding to the coat proteins. P22, on the other hand, is composed of up to 415 coat proteins, 100-300 scaffold proteins, and 12 portal proteins. However, the P22 VLP has been engineered to consist of 420 coat proteins and only the 100-300 scaffold proteins, which can subsequently be removed with guanidine hydrochloride, leaving only the coat proteins. Like the HBV VLP, these VLPs assemble with icosahedral geometry. All three can be produced in *E. coli*, but Qb can also be produced in yeast and both Qb and MS2 can be produced using cell-free protein synthesis. MS2 VLPs have been purified using size-exclusion chromatography, differential centrifugation, or immobilized metal affinity chromatography (for VLPs containing hexahistidine tags). Acids or urea can be used to disassemble the purified MS2 VLPs to obtain the dimers, which can then be reassembled after removal of the disassembly agent and the addition of the stem-loop RNA. Qb VLPs have been purified using size exclusion chromatography and the dimers can be obtained by disassembling the VLPs using acid, which can then be reassembled similar to MS2. P22 VLPs have been purified using size-exclusion chromatography or differential centrifugation and can also be disassembled using acid to obtain the coat proteins. Addition of scaffold proteins is required to reassemble the P22 VLP, but these can subsequently be removed. These bacteriophage-derived VLPs differ from HBc VLPs mainly in the assembly stimulus, using additional biomolecules (RNA or proteins) to initiate self-assembly instead of increasing the salt concentration.

Plant Virus-Based VLPs.

In various embodiments, the VLP is a plant virus-based VLP. In various embodiments, the plant virus-based VLP is derived from the cowpea leaf: CCMV and CPMV. Neither virus has a lipid envelope. Both VLPs assemble with icosahedral geometry. The CCMV VLPs are formed from 90 homodimers and can be produced in *E. coli* or yeast. They have been purified using size exclusion chromatography or immobilized metal affinity chromatography, using coat proteins with hexahistidine extensions. 46,62 Dimers can be obtained by dialyzing the assembled VLPs against 0.5 M $CaCl_2$ or by purifying hexahistidine tagged dimers directly. Combining the dimers with RNA in a 1:6 mass ratio and lowering the pH to 4-5 induces self-assembly. CPMV, on the other hand, is formed from 60 copies of the VP60 protein which must first be proteolyzed into the L and S coat proteins (60 copies of each). Unfortunately, the VLP cannot be produced using *E. coli* or yeast; insect cells or plants must be used. The VLPs have been purified using differential centrifugation, but the coat proteins cannot yet be obtained in usable quantities. The inability to produce the VLP in *E. coli* or obtain purified coat proteins adds another challenge for targeted drug delivery; however, CPMV has been actively evaluated for therapeutic use due to the ability to easily display ligands on its surface and load cargo through association with its genome. In other embodiments, the plant virus-based VLP is a Tobacco Mosaic Virus (TMV).

Tumor Specificity of VLPs.

In various embodiments, the VLP binds preferentially to tumor cells. The VLPs' tumor preference may originate from several sources including the VLP's charge (positive or negative), shape and size (different aspect ratio filaments and diameter spheres), shielding (self-proteins/peptides and polymers of various sizes and densities), and targeting (ligands for receptors or environmental factors displayed on different linkers at various densities).

In terms of charge, in various embodiments, the VLP contains a positive surface charge. Positive charged VLPs stay longer in circulation. Due to the abundant presence of proteoglycan in the cell membrane conferring a negative charge and collagen within the tumor interstitial space conferring a positive charge, positively charged particles are more likely to have enhanced binding to mammalian cells and are better able to avoid aggregation and penetrate tumor tissue. Some examples demonstrating these charge-based effects include polyarginine-decorated CPMV found to be taken up eight times more efficiently than native CPMV in a human cervical cancer.

With regards to shape, the shape and flexibility of the VLP will play an additional role in VLPs ability to diffuse throughout a tumor. E.g. A comparison between the diffusion profiles of a spherical and rod-shaped particle was performed with CPMV and TMV using a spheroid model, and it was shown that whereas CPMV (Sphere) experienced a steady diffusion profile, TMV (rod shape) exhibited a two-phase diffusion behavior that entailed an extremely rapid early loading phase, which could be attributed to its movement axially, acting like a needle. Some other advantageous properties that are conferred by elongated particles include better margination toward the vessel wall and stronger adherence due to greater surface area for interaction, which not only have implications for tumor homing but also for enhanced targeting of cardiovascular disease.

Besides passive tumor homing properties, natural interactions of viruses with certain cells can also be exploited. CPMV (cowpea mosaic virus) in particular exhibits unique specificity in interacting with surface vimentin, which is found on endothelial, cancer, and inflammatory cells. The native affinity of CPMV for surface vimentin allows for high-resolution imaging of microvasculature up to 500 μm in depth, which cannot be achieved through the use of other nanoparticles, as they tend to aggregate and block the vasculature. This interaction can be utilized for a range of applications, such as delivery to a panel of cancer cells including cervical, breast, and colon cancer cell lines, delineation of atherosclerotic lesions, and intravital imaging of tumor vasculature and angiogenesis. Another example of an existing endogenous association is CPV with transferrin receptor (TfR), an important receptor for iron transport into cells and highly upregulated by numerous cancer cell lines. Even after dye labeling, CPV retains its specificity for TfR and was shown to bind to receptors found on HeLa cervical cancer cells, HT-29 colon cancer cells, and MDA-MB-231 breast cancer cells.

In various embodiments, the VLP is capable of targeting a protein expressed preferentially on the tumor cell surface. Such proteins are typically overexpressed on the surface of tumor cells, but some if not all may also be found in the blood, i.e. serum. Non-limiting examples of such surface markers include: CEA (carcinoembryonic antigen), E-cadherin, EMA (epithelial membrane antigen; aka MUC-1), vimentin, fibronectin, Her2/neu (human epidermal growth factor receptor type 2, also called Erb b2), αvβ3 integrin, EpCAM (epithelial cell adhesion molecule), FR-α (folate receptor-alpha), PAR (urokinase-type plasminogen activator receptor), and transferrin receptor (over expressed in tumor cells).

Peptides are often used to label cancerous cells based on recognition of their transmembrane proteins. The most commonly used peptide is arginylglycylaspartic acid (RGD), composed of L-arginine, glycine, and L-aspartic acid. RGD was first isolated from the cell-binding domain of fibronectin, a glycoprotein that binds to integrins, and is involved in cell-cell and cell-extracellular matrix (ECM) attachment and signaling by binding collagen, fibrin, and proteoglycans. RGD peptides have the highest affinity for a type of cell surface integrins, αvβ which are highly expressed in tumoral endothelial cells, but not in normal endothelial cells. In various embodiments such a peptide sequence is incorporated into the conjugated VLP.

Fusion Protein.

In various embodiments the fusion protein comprises a cleavage sequence. The cleavage sequence can be any sequence capable of being preferentially cleaved by or near a tumor cell. The insertion of this cleavage sequence into the fusion protein, allows the protein to remain inactive until it enters the tumor micro-environment. By taking advantage of the elevated activities of particular proteases in cancer tissues, the recall protein is not released from the VLP and able to actively coat MHC receptors until the recall protein enters the tumor microenvironment. Several proteases are known in the art to be active in the tumor microenvironment. For example, several metallo-, cysteine and serine proteases are known. From the standpoint of cancer therapy, an additional attraction is that because the proteases responsible for prodrug cleavage may come not just from cancer cells but also from the stromal components of tumors, release of the active drug direction into the tumor microenvironment does not depend on a target expressed only by the cancer cells. Instead, it is the entire tumor ecosystem that represents the target.

Recall Protein.

In various embodiments, the recall protein is an epitope, which is recognized by a T cell or T cell population, which already exists in a subject. In various embodiments, this existing T cell or T cell population exists because of a prior infection or vaccination. In various embodiments of the invention, the recall protein is an epitope that is capable of being, bound by a T cell. In various embodiments, the recall protein is an epitope capable of being bound by a T cell already present in a subject. In this context, "capable of being bound" means that a "epitope" is presented on the surface of a cell, where it is bound to MHC molecules directly. T cell epitopes presentable by MHC I can be bound by the T cell receptor of cytotoxic CD8 T lymphocytes (CD8 T cells or CTLs). T cell epitopes presentable by MHC I are typically peptides of 9 to 12 amino acids in length. In various embodiments, a conjugated VLP is provided which allows release of a T cell response eliciting peptide, which is directly presentable via MHC class I. As the released recall protein does not require delivery to the antigen processing machinery in the cytosol, the T cell response eliciting peptide are presented on the surface of the target cell in a short amount of time. Hence, in one embodiment of the invention, in less than 8.5 hours after administration the target cell the T cell response eliciting peptide is presented on the surface of the target cell via an MHC class I molecule. In another embodiment of the invention, in less than 23.5 hours after introduction of the conjugated VLP to the target cell the T cell response eliciting peptide is presented on the surface of the target cell via an MHC class I molecule. In another embodiment of the invention, the conjugated VLP is capable of mediating T cell cytotoxicity against the target cell within less than 6 hours after administration of the conjugated VLP to the target cell.

In various embodiments, the fusion protein comprises at least two recall proteins. These recall proteins might be epitopes derived from different proteins, or they may be epitopes of the same protein. In various embodiments, the pathogen is a virus, a bacterium, a fungus, or a parasite.

In various embodiments, the preexisting T cells are specific to a vaccine epitope. In various embodiments the epitope is derived from an early childhood vaccine. In various embodiments the preexisting immunity is the result of prior administration of a human vaccine.

Non-limiting examples of a virus includes, a vaccinia virus, a varicella zoster virus, a Herpes zoster virus, rubella, a hepatitis virus, e.g., hepatitis A virus or hepatitis B virus or hepatitis C virus, influenza, e.g., type A or type B, a measles virus, a mumps virus, a polio virus, a variola (smallpox) virus, a rabies virus, a Dengue virus, an Ebola virus, a West Nile virus, a yellow fever virus, or a zika virus.

Non-limiting examples of a bacterium include, a *Bordetella pertussis, chlamydia, trachomatis, Clostridium tetani,* diphtheria, *Hemophilus influenza, Meningococcus, Pneumococcus, Vibrio cholera, Mycobacterium tuberculosis,* BCG, typhoid, *E. coli, salmonella, Legionella pneumophila, rickettsia, Treponema pallidum pallidum, Streptococcus* group A or group B, *Streptococcus pneumonia, Bacillus anthracis, Clostridium botulinum,* or a *Yersinia* sp bacteria.

Non-limiting examples of a parasite include, *Entamoeba histolytica, Toxoplasma gondii,* a *Trichinella* sp., e.g., *Trichinella spiralis,* a *Trichomonas* sp., e.g., *Trichomonas vaginalis,* a *Trypanosoma* sp., e.g., *Trypanosoma brucei gambiense, Trypanosoma brucei rhodesiense,* or a *Trypanosoma cruzi,* or a *plasmodium,* e.g., *Plasmodium falciparum, Plasmodium vivax,* or *Plasmodium malariae.*

In various embodiments, the recall protein is selected from the list included in Table 1:

TABLE 1

Recall Protein Epitopes

| Epitope Sequence | SEQ ID NO | Virus Type | MHC allele | Viral Protein |
|---|---|---|---|---|
| SLPRSRTPI | 4 | Chicken Pox (VZV) | A*02:01 | 1E62 |
| SAPLPSNRV | 5 | Chicken Pox (VZV) | A*02:01 | 1E62 |
| GSAPLPSNRV | 6 | Chicken Pox (VZV) | A*02:01 | 1E62 |
| ALWALPHAA | 7 | Chicken Pox (VZV) | A*02:01 | 1E62 |
| SLSGLYVFV | 8 | Shingles vaccines | A*02:01 | Glycoprotein E |
| YLGVYIWNM | 9 | Shingles vaccines | A*02:01 | Glycoprotein E |
| KIHEAPFDL | 10 | Shingles vaccines | A*02:01 | Glycoprotein E |
| LLCLVIFLI | 11 | Shingles vaccines | A*02:01 | Glycoprotein E |
| DLLLEWLYV | 12 | Shingles vaccines | A*02:01 | Glycoprotein E |
| SMYYAGLPV | 13 | Shingles vaccines | A*02:01 | Glycoprotein E |
| ILHDGGTTL | 14 | Shingles vaccines | A*02:01 | Glycoprotein E |
| WLYVPIDPT | 15 | Shingles vaccines | A*02:01 | Glycoprotein E |
| VLMGFGIIT | 16 | Shingles vaccines | A*02:01 | Glycoprotein E |
| CLVIFLICT | 17 | Shingles vaccines | A*02:01 | Glycoprotein E |
| KEADQPWIV | 18 | Shingles vaccines | A*02:01 | Glycoprotein E |
| VVSTVDHFV | 19 | Shingles vaccines | A*02:01 | Glycoprotein E |
| FLICTAKRM | 20 | Shingles vaccines | A*02:01 | Glycoprotein E |
| VLRTEKQYL | 21 | Shingles vaccines | A*02:01 | Glycoprotein E |
| HMWNYHSHV | 22 | Shingles vaccines | A*02:01 | Glycoprotein E |
| TVNKPVVGV | 23 | Shingles vaccines | A*02:01 | Glycoprotein E |
| FVVYFNGHV | 24 | Shingles vaccines | A*02:01 | Glycoprotein E |
| WIVVNTSTL | 25 | Shingles vaccines | A*02:01 | Glycoprotein E |
| VAYTVVSTV | 26 | Shingles vaccines | A*02:01 | Glycoprotein E |
| FMYMSLLGV | 27 | measles | A*02:01 | m50 |
| SLWGSLLML | 28 | measles | A*02:01 | C protein |

TABLE 1-continued

Recall Protein Epitopes

| Epitope Sequence | SEQ ID NO | Virus Type | MHC allele | Viral Protein |
|---|---|---|---|---|
| LLAVIFVMFL | 29 | measles | A*02:01 | H38 |
| SMYRVFEVGV | 30 | measles | A*02:01 | H250-259 |
| ILPGQDLQYV | 31 | measles | A*02:01 | H516-525 |
| KLWCRHFCV | 32 | measles | A*02:01 | H576 |
| KLWCRHFCVL | 33 | measles | A*02:01 | H576 |
| RLSDNGYYTV | 34 | measles | A*02:01 | M164 |
| KLLRYYTEI | 35 | measles | A*02:01 | F205 |
| KLWESPQEI | 36 | measles | A*02:01 | C 84 |
| RLLDRLVRL | 37 | measles | A*02:01 | N50 |
| KLMPNITLL | 38 | measles | A*02:01 | F57 |
| TLLNNCTRV | 39 | measles | A*02:01 | F64 |
| EMLTLATWV | 40 | Hep B | A*02:01 | C64-72 |
| FLPSDFFPSV | 41 | Hep B | A*02:01 | Core 18 |
| FLPADFFPSV | 42 | Hep B | A*02:01 | Core 19 |
| FLPSDFFPSI | 43 | Hep B | A*02:01 | Core 20 |
| WLSLLVPF | 44 | Hep B | A*02:01 | ENV335 |
| FLLTRILTI or FLLTRILTL | 45 or 46 | Hep B | A*02:01 | ENV183 |
| GLSPTVWLSV | 47 | Hep B | A*02:01 | ENV348 |
| LLDYQGMLPV | 48 | Hep B | A*02:01 | ENV260 |
| LLCLIFLLV | 49 | Hep B | A*02:01 | ENV251 |
| SIVSPFIPLL | 50 | Hep B | A*02:01 | ENV370 |
| FLLTKILTI | 51 | Hep B | A*02:01 | ENV183 |
| ILSPFLPLL | 52 | Hep B | A*02:01 | ENV371 |
| FLLSLGIHL | 53 | Hep B | A*02:01 | POL 575 |
| GLSRYVARL | 54 | Hep B | A*02:01 | POL 455 |
| SLYADSPSV | 55 | Hep B | A*02:01 | POL 816 |
| YMDDVVLGA | 56 | Hep B | A*02:01 | POL 551 |
| ALMPLYACI | 57 | Hep B | A*02:01 | POL 655 |
| VLHKRTLGL | 58 | Hep B | A*02:01 | HBx 92 |
| CLFKDWEEL | 59 | Hep B | A*02:01 | Hbx115 |
| STLPETTVVRR | 60 | Hep B | A*03, A*11 | Core 141 |
| EYLVSFGVW | 61 | Hep B | A*31, A*68 | core 117 |
| FFPSIRDLL | 62 | Hep B | A*24 | Core 23 |
| SWLSLLVPF | 63 | Hep B | A*24 | Env 334 |
| KYTSFPWLL | 64 | Hep B | A*24 | Pol 756 |
| HLSLRGLFV | 65 | Hep B | A*02:01 | HBx 52-60 |
| CLFKDWEEL | 66 | Hep B | A*02:01 | HBx 115-123 |

TABLE 1-continued

Recall Protein Epitopes

| Epitope Sequence | SEQ ID NO | Virus Type | MHC allele | Viral Protein |
|---|---|---|---|---|
| LPSDFFPSV | 67 | Hep B | B*51 | Core 19 |
| GILGFVFTL | 68 | Influenza | HLA-A2 | M1 |
| ILGFVFTLTVPSERGLQRRRF | 69 | Influenza | | |
| LIRHENRMVLASTTAKA | 70 | Influenza | | |
| LQAYQKRMGVQMQR | 71 | Influenza | | |
| YVYIDIISGEAVK | 72 | | | |
| IVLSLINPFNI | 73 | | | |
| (K)GILGFVFIL(T)(V) | 74 | | | |
| KLSTRGWIASNEN | 75 | | | |
| RGLQRRRFVQNALNGNG | 76 | | | |
| FMYSDFHFI | 77 | | | |
| NLNPMVATV | 3 | | | |
| VAIIEVDNEQPTTRAQKL | 78 | | | |
| Any 9-mer sequence of GACV AIIEVDNEQPITRAQKLF AMWRITYKDTVQLRRKL | 79 | | | |
| SVRDRLARL | 80 | | | |
| LLDRVRFMGV | 81 | | | |
| CLGGLLTMV | 82 | | | |
| GLCTLVAML | 83 | | | |

In various embodiments the epitope is derived from an epitope of a human vaccine. In various embodiments the vaccine is an early childhood vaccine. Certain non-limiting examples of suitable vaccines are listed in Table 2 below:

TABLE 2

Approved Vaccines Containing Recall Protein Epitopes

| Type | Commercial Name | Form | Source | Responsible National Regulatory Authority |
|---|---|---|---|---|
| Diphtheria-Tetanus-Pertussis (whole cell)-Hepatitis B-Hemophilus influenzae type b | Quinvaxem | Liquid: ready to use | Janssen Vaccines Corp. | Ministry of Food and Drug Safety |
| Diphtheria-Tetanus | Adsorbed DT Vaccine | Liquid TABLE 2-continued Approved Vaccines Containing Recall Protein Epitopes

| Type | Commercial Name | Form | Source | Responsible National Regulatory Authority |
|---|---|---|---|---|
| Yellow Fever | Yellow Fever | excipient diluent before use Lyophilized Lyophilized active component to be reconstituted with excipient diluent before use | Bio-Manguinhos/ Fiocruz | Agencia Nacional da Vigilancia Sanitaria |
| Yellow Fever | Yellow Fever | Lyophilized Lyophilized active component to be reconstituted with excipient diluent before use | Bio-Manguinhos/ Fiocruz | Agencia Nacional da Vigilancia Sanitaria |
| Yellow Fever | Yellow Fever | Lyophilized Lyophilized active component to be reconstituted with excipient diluent before use | Bio-Manguinhos/ Fiocruz | Agencia Nacional da Vigilancia Sanitaria |
| Hepatitis B | Heberbiovac HB | Liquid: ready to use | Centro de Ingenieria Genetica y Biotecnologia | Centro para el Control Estatal de la Calidad de los Medicamentos |
| Hepatitis B | Heberbiovac HB | Liquid: ready to use | Centro de Ingenieria Genetica y Biotecnologia | Centro para el Control Estatal de la Calidad de los Medicamentos |
| Rabies | Rabipur | Lyophilized active component to be reconstituted with excipient diluent before use | Chiron Behring Vaccines Private Ltd. | Central Drugs Standard Control Organization |
| Rabies | Rabipur | Lyophilized active component to be reconstituted with excipient diluent before use | GlaxoSmith Kline Vaccines GmbH | Paul-Ehrlich-Institut |
| Haemophilus influenzae type b | Vaxem HIB | Liquid: ready to use | Novartis Vaccines and Diagnostics S.r.l | Agenzia Italiana del Farmaco |
| Hepatitis B | Engerix | Liquid: ready to use | GlaxoSmith Kline Biologicals SA | Federal Agency for Medicines and Health Products |
| Hepatitis B | Engerix | Liquid: ready to use | GlaxoSmith Kline Biologicals SA | Federal Agency for Medicines and Health Products |
| Hepatitis B | Engerix | Liquid: ready to use | GlaxoSmith Kline Biologicals SA | Federal Agency for Medicines and Health Products |
| Polio Vaccine - Oral (OPV) Trivalent | Polio sabin | Liquid: ready to use | GlaxoSmith Kline Biologicals SA | Federal Agency for Medicines and Health Products |
| Polio Vaccine - Oral (OPV) Trivalent | Polio sabin | Liquid: ready to use | GlaxoSmith Kline Biologicals SA | Federal Agency for Medicines and Health Products |
| Measles, Mumps and Rubella | Priorix | Lyophilized active component to be reconstituted with excipient diluent before use | GlaxoSmith Kline Biologicals SA | Federal Agency for Medicines and Health Products |
| Rotavirus | Rotarix | Liquid: ready to use | GlaxoSmith Kline Biologicals SA | Federal Agency for Medicines and Health Products |
| Polio Vaccine - Oral (OPV) Trivalent | Polioviral vaccine | Liquid: ready to use | Haffkine Bio Pharmaceutical Corporation Ltd | Central Drugs Standard Control Organization |
| Yellow Fever | Stabilized Yellow Fever Vaccine | Lyophilized active component to be reconstituted with excipient diluent before use | Institut Pasteur de Dakar | Ministère de la Santé publique |
| Yellow Fever | Stabilized Yellow Fever Vaccine | Lyophilized active component to be reconstituted with excipient diluent before use | Institut Pasteur de Dakar | Ministère de la Santé publique |
| Yellow Fever | Stabilized Yellow Fever Vaccine | Lyophilized active component to be reconstituted with excipient diluent before use | Institut Pasteur de Dakar | Ministère de la Santé publique |

TABLE 2-continued

Approved Vaccines Containing Recall Protein Epitopes

| Type | Commercial Name | Form | Source | Responsible National Regulatory Authority |
|---|---|---|---|---|
| BCG | BCG Freeze Dried Glutamate vaccine | Lyophilized active component to be reconstituted with excipient diluent before use | Japan BCG Laboratory | Chiba Local Government |
| Hepatitis B | Euvax B | Liquid: ready to use | LG Chem Ltd | Ministry of Food and Drug Safety |
| Hepatitis B | Euvax B | Liquid: ready to use | LG Chem Ltd | Ministry of Food and Drug Safety |
| BCG | BCG Vaccine | Lyophilized active component to be reconstituted with excipient diluent before use | Bul Bio - National Center of Infectious and Parasitic Diseases Ltd. | Bulgarian Drug Agency |
| BCG | BCG Vaccine | Lyophilized active component to be reconstituted with excipient diluent before use | Bul Bio - National Center of Infectious and Parasitic Diseases Ltd. | Bulgarian Drug Agency |
| Tetanus Toxoid | Tetatox | Liquid: ready to use | Bul Bio - National Center of Infectious and Parasitic Diseases Ltd. | Bulgarian Drug Agency |
| Tetanus Toxoid | Tetatox | Liquid: ready to use | Bul Bio - National Center of Infectious and Parasitic Diseases Ltd. | Bulgarian Drug Agency |
| Diphtheria-Tetanus | Diftet | Liquid: ready to use | Bul Bio - National Center of Infectious and Parasitic Diseases Ltd. | Bulgarian Drug Agency |
| Diphtheria-Tetanus | Diftet | Liquid: ready to use | Bul Bio - National Center of Infectious and Parasitic Diseases Ltd. | Bulgarian Drug Agency |
| Diphtheria-Tetanus (reduced antigen content) | Tetadif | Liquid: ready to use | Bul Bio - National Center of Infectious and Parasitic Diseases Ltd. | Bulgarian Drug Agency |
| Diphtheria-Tetanus (reduced antigen content) | Tetadif | Liquid: ready to use | Bul Bio - National Center of Infectious and Parasitic Diseases Ltd. | Bulgarian Drug Agency |
| Diphtheria-Tetanus-Pertussis (whole cell)-Hepatitis B-Haemophilus influenzae type b | Easyfive-TT | Liquid: ready to use | Panacea Biotec Ltd. | Central Drugs Standard Control Organization |
| Diphtheria-Tetanus (reduced antigen content) | IMOVAX dT adult | Liquid: ready to use | Sanofi Pasteur SA | Agence nationale de sécurité du médicament et des produits de santé |
| Polio Vaccine - Inactivated (IPV) | IMOVAX POLIO | Liquid: ready to use | Sanofi Pasteur SA | Agence nationale de sécurité du médicament et des produits de santé |
| Polio Vaccine - Oral (OPV) Trivalent | OPVERO | Liquid: ready to use | Sanofi Pasteur SA | Agence nationale de sécurité du médicament et des produits de santé |
| Polio Vaccine - Oral (OPV) Trivalent | OPVERO | Liquid: ready to use | Sanofi Pasteur SA | Agence nationale de sécurité du médicament et des produits de santé |
| Polio Vaccine - Oral (OPV) Trivalent | OPVERO | Liquid: ready to use | Sanofi Pasteur SA | Agence nationale de sécurité du médicament et des produits de santé |
| Tetanus Toxoid | TETAVAX | Liquid: ready to use | Sanofi Pasteur SA | Agence nationale de sécurité du médicament et des produits de santé |

TABLE 2-continued

Approved Vaccines Containing Recall Protein Epitopes

| Type | Commercial Name | Form | Source | Responsible National Regulatory Authority |
| --- | --- | --- | --- | --- |
| Tetanus Toxoid | TETAVAX | Liquid: ready to use | Sanofi Pasteur SA | Agence nationale de sécurité du médicament et des produits de santé |
| Haemophilus influenzae type b | Act-HIB | Lyophilized active component to be reconstituted with excipient diluent before use | Sanofi Pasteur SA | Agence nationale de sécurité du médicament et des produits de santé |
| Rabies | VERORAB | Lyophilized active component to be reconstituted with excipient diluent before use | Sanofi Pasteur SA | Agence nationale de sécurité du médicament et des produits de santé |
| Yellow Fever | STAMARIL | Lyophilized active component to be reconstituted with excipient diluent before use | Sanofi Pasteur SA | Agence nationale de sécurité du médicament et des produits de santé |
| Meningococcal A+C | POLYSACCHARIDE MENINGOCOCCAL A + C VACCINE | Lyophilized active component to be reconstituted with excipient diluent before use | Sanofi Pasteur SA | Agence nationale de sécurité du médicament et des produits de santé |
| Polio Vaccine - Oral (OPV) Monovalent Type 1 | ORAL MONOVALENT TYPE 1 POLIOMYELITIS VACCINE | Liquid: ready to use | Sanofi Pasteur SA | Agence nationale de sécurité du médicament et des produits de santé |
| cholera: inactivated oral | Dukoral | Liquid: ready to use | Valneva Sweden AB | Medical Products Agency |
| BCG | BCG Vaccine | Lyophilized active component to be reconstituted with excipient diluent before use | Serum Institute of India Pvt. Ltd. | Central Drugs Standard Control Organization |
| Diphtheria-Tetanus | Diphtheria and Tetanus Vaccine Adsorbed (Paediatric) | Liquid: ready to use | Serum Institute of India Pvt. Ltd. | Central Drugs Standard Control Organization |
| Diphtheria-Tetanus | Diphtheria and Tetanus Vaccine Adsorbed (Pediatric) | Liquid: ready to use | Serum Institute of India Pvt. Ltd. | Central Drugs Standard Control Organization |
| Diphtheria-Tetanus | Diphtheria and Tetanus Vaccine Adsorbed (Pediatric) | Liquid: ready to use | Serum Institute of India Pvt. Ltd. | Central Drugs Standard Control Organization |
| Diphtheria-Tetanus (reduced antigen content) | Diphtheria and Tetanus Vaccine Adsorbed for Adults and Adolescents | Liquid: ready to use | Serum Institute of India Pvt. Ltd. | Central Drugs Standard Control Organization |
| Diphtheria-Tetanus (reduced antigen content) | Diphtheria and Tetanus Vaccine Adsorbed for Adults and Adolescents | Liquid: ready to use | Serum Institute of India Pvt. Ltd. | Central Drugs Standard Control Organization |
| Diphtheria-Tetanus (reduced antigen content) | Diphtheria and Tetanus Vaccine Adsorbed for Adults and Adolescents | Liquid: ready to use | Serum Institute of India Pvt. Ltd. | Central Drugs Standard Control Organization |
| Diphtheria-Tetanus-Pertussis (whole cell) | Diphtheria-Tetanus-Pertussis Vaccine Adsorbed | Liquid: ready to use | Serum Institute of India Pvt. Ltd. | Central Drugs Standard Control Organization |
| Diphtheria-Tetanus-Pertussis (whole cell) | Diphtheria-Tetanus-Pertussis Vaccine Adsorbed | Liquid: ready to use | Serum Institute of India Pvt. Ltd. | Central Drugs Standard Control Organization |
| Diphtheria-Tetanus-Pertussis (whole cell) | Diphtheria-Tetanus-Pertussis | Liquid: ready to use | Serum Institute of India Pvt. Ltd. | Central Drugs Standard Control Organization |

TABLE 2-continued

Approved Vaccines Containing Recall Protein Epitopes

| Type | Commercial Name | Form | Source | Responsible National Regulatory Authority |
|---|---|---|---|---|
| Diphtheria-Tetanus-Pertussis (whole cell)-Hepatitis B | Diphtheria, Tetanus, Pertussis and Hepatitis B Vaccine Adsorbed | Liquid: ready to use | Serum Institute of India Pvt. Ltd. | Central Drugs Standard Control Organization |
| Diphtheria-Tetanus-Pertussis (whole cell)-Hepatitis B | Diphtheria, Tetanus, Pertussis and Hepatitis B Vaccine Adsorbed | Liquid: ready to use | Serum Institute of India Pvt. Ltd. | Central Drugs Standard Control Organization |
| Diphtheria-Tetanus-Pertussis (whole cell)-Hepatitis B | Diphtheria, Tetanus, Pertussis and Hepatitis B Vaccine Adsorbed | Liquid: ready to use | Serum Institute of India Pvt. Ltd. | Central Drugs Standard Control Organization |
| Hepatitis B | Hepatitis B Vaccine (rDNA) (Adult) | Liquid: ready to use | Serum Institute of India Pvt. Ltd. | Central Drugs Standard Control Organization |
| Hepatitis B | Hepatitis B Vaccine (rDNA) (Adult) | Liquid: ready to use | Serum Institute of India Pvt. Ltd. | Central Drugs Standard Control Organization |
| Hepatitis B | Hepatitis B Vaccine (rDNA) (Paediatric) | Liquid: ready to use | Serum Institute of India Pvt. Ltd. | Central Drugs Standard Control Organization |
| Hepatitis B | Hepatitis B Vaccine (rDNA) (Paedriatic) | Liquid: ready to use | Serum Institute of India Pvt. Ltd. | Central Drugs Standard Control Organization |
| Tetanus Toxoid | Tetanus Toxoid Vaccine Adsorbed | Liquid: ready to use | Serum Institute of India Pvt. Ltd. | Central Drugs Standard Control Organization |
| Tetanus Toxoid | Tetanus Toxoid Vaccine Adsorbed | Liquid: ready to use | Serum Institute of India Pvt. Ltd. | Central Drugs Standard Control Organization |
| Tetanus Toxoid | Tetanus Toxoid Vaccine Adsorbed | Liquid: ready to use | Serum Institute of India Pvt. Ltd. | Central Drugs Standard Control Organization |
| Measles and Rubella | Measles and Rubella Vaccine, Live, Attenuated | Lyophilized active component to be reconstituted with excipient diluent before use | Serum Institute of India Pvt. Ltd. | Central Drugs Standard Control Organization |
| Measles and Rubella | Measles and Rubella Vaccine, Live, Attenuated | Lyophilized active component to be reconstituted with excipient diluent before use | Serum Institute of India Pvt. Ltd. | Central Drugs Standard Control Organization |
| Measles and Rubella | Measles and Rubella Vaccine, Live, Attenuated | Lyophilized active component to be reconstituted with excipient diluent before use | Serum Institute of India Pvt. Ltd. | Central Drugs Standard Control Organization |
| Measles and Rubella | Measles and Rubella Vaccine, | Lyophilized active component | Serum Institute of India Pvt. Ltd. | Central Drugs Standard Control Organization |

TABLE 2-continued

Approved Vaccines Containing Recall Protein Epitopes

| Type | Commercial Name | Form | Source | Responsible National Regulatory Authority |
|---|---|---|---|---|
| | | Live, Attenuated | to be reconstituted with excipient diluent before use | |
| Measles, Mumps and Rubella | Measles, Mumps and Rubella Vaccine, Live, Attenuated | Lyophilized active component to be reconstituted with excipient diluent before use | Serum Institute of India Pvt. Ltd. | Central Drugs Standard Control Organization |
| Measles, Mumps and Rubella | Measles, Mumps and Rubella Vaccine, Live, Attenuated | Lyophilized active component to be reconstituted with excipient diluent before use | Serum Institute of India Pvt. Ltd. | Central Drugs Standard Control Organization |
| Measles, Mumps and Rubella | Measles, Mumps and Rubella Vaccine, Live, Attenuated | Lyophilized active component to be reconstituted with excipient diluent before use | Serum Institute of India Pvt. Ltd. | Central Drugs Standard Control Organization |
| Measles, Mumps and Rubella | Measles, Mumps and Rubella Vaccine, Live, Attenuated | Lyophilized active component to be reconstituted with excipient diluent before use | Serum Institute of India Pvt. Ltd. | Central Drugs Standard Control Organization |
| Measles | Measles Vaccine, Live, Attenuated | Lyophilized active component to be reconstituted with excipient diluent before use | Serum Institute of India Pvt. Ltd. | Central Drugs Standard Control Organization |
| Measles | Measles Vaccine, Live, Attenuated | Lyophilized active component to be reconstituted with excipient diluent before use | Serum Institute of India Pvt. Ltd. | Central Drugs Standard Control Organization |
| Measles | Measles Vaccine, Live, Attenuated | Lyophilized active component to be reconstituted with excipient diluent before use | Serum Institute of India Pvt. Ltd. | Central Drugs Standard Control Organization |
| Measles | Measles Vaccine, Live, Attenuated | Lyophilized active component to be reconstituted with | Serum Institute of India Pvt. Ltd. | Central Drugs Standard Control Organization |

TABLE 2-continued

Approved Vaccines Containing Recall Protein Epitopes

| Type | Commercial Name | Form | Source | Responsible National Regulatory Authority |
| --- | --- | --- | --- | --- |
| | | excipient diluent before use | | |
| Rubella | Rubella Vaccine, Live, Attenuated | Lyophilized active component to be reconstituted with excipient diluent before use | Serum Institute of India Pvt. Ltd. | Central Drugs Standard Control Organization |
| Rubella | Rubella Vaccine, Live, Attenuated | Lyophilized active component to be reconstituted with excipient diluent before use | Serum Institute of India Pvt. Ltd. | Central Drugs Standard Control Organization |
| Rubella | Rubella Vaccine, Live, Attenuated | Lyophilized active component to be reconstituted with excipient diluent before use | Serum Institute of India Pvt. Ltd. | Central Drugs Standard Control Organization |
| Rubella | Rubella Vaccine, Live, Attenuated | Lyophilized active component to be reconstituted with excipient diluent before use | Serum Institute of India Pvt. Ltd. | Central Drugs Standard Control Organization |
| Tetanus Toxoid | ShanTT | Liquid: ready to use | Shantha Biotechnics Private Limited (A Sanofi Company) | Central Drugs Standard Control Organization |
| Tetanus Toxoid | ShanTT | Liquid: ready to use | Shantha Biotechnics Private Limited (A Sanofi Company) | Central Drugs Standard Control Organization |
| Diphtheria-Tetanus-Pertussis (whole cell)-Hepatitis B-Haemophilus influenzae type b | Shan-5 | Liquid: ready to use | Shantha Biotechnics Private Limited (A Sanofi Company) | Central Drugs Standard Control Organization |
| Diphtheria-Tetanus-Pertussis (whole cell)-Hepatitis B-Haemophilus influenzae type b | Shan-5 | Liquid: ready to use | Shantha Biotechnics Private Limited (A Sanofi Company) | Central Drugs Standard Control Organization |
| BCG | BCG Vaccine SSI | Lyophilized active component to be reconstituted with excipient diluent before use | AJ Vaccines A/S | Danish Medicines Agency |
| Rotavirus | Rotateq | Liquid: ready to use | Merck Vaccines | CBER/FDA |
| Measles, Mumps and Rubella | rHA M-M-R II | Lyophilized active component to be reconstituted with excipient diluent before use | Merck Vaccines | European Medicines Agency |
| Rotavirus | Rotarix | Liquid: ready to use | GlaxoSmith Kline Biologicals SA | Federal Agency for Medicines and Health Products |
| Yellow Fever | — | Lyophilized active component to be reconstituted with excipient diluent before use | Federal State Budgetary Scientific Institution «Chumakov Federal Scientific Center for Reserch & Development of Immune- | Federal Service on Surveillance in Healthcare (ROSZDRAVNADZOR) of the Russian Federation |

TABLE 2-continued

Approved Vaccines Containing Recall Protein Epitopes

| Type | Commercial Name | Form | Source | Responsible National Regulatory Authority |
| --- | --- | --- | --- | --- |
| | | | And Biological Products», Russian Academy of Sciences | |
| Yellow Fever | — | Lyophilized active component to be reconstituted with excipient diluent before use | Federal State Budgetary Scientific Institution «Chumakov Federal Scientific Center for Reserch & Development of Immune- And Biological Products», Russian Academy of Sciences | Federal Service on Surveillance in Healthcare (ROSZDRAVNADZOR) of the Russian Federation |
| Yellow Fever | — | Lyophilized active component to be reconstituted with excipient diluent before use | Federal State Budgetary Scientific Institution «Chumakov Federal Scientific Center for Reserch & Development of Immune- And Biological Products», Russian Academy of Sciences | Federal Service on Surveillance in Healthcare (ROSZDRAVNADZOR) of the Russian Federation |
| Human Papillomavirus (Quadrivalent) | Gardasil | Liquid: ready to use | Merck Vaccines | European Medicines Agency |
| Human Papillomavirus (Bivalent) | Cervarix | Liquid: ready to use | GlaxoSmith Kline Biologicals SA | Federal Agency for Medicines and Health Products |
| Human Papillomavirus (Bivalent) | Cervarix | Liquid: ready to use | GlaxoSmith Kline Biologicals SA | Federal Agency for Medicines and Health Products |
| Polio Vaccine - Oral (OPV) Monovalent Type 1 | Polio Sabin Mono T1 | Liquid: ready to use | GlaxoSmith Kline Biologicals SA | Federal Agency for Medicines and Health Products |
| Polio Vaccine - Oral (OPV) Monovalent Type 1 | Polio Sabin Mono T1 | Liquid: ready to use | GlaxoSmith Kline Biologicals SA | Federal Agency for Medicines and Health Products |
| Polio Vaccine - Oral (OPV) Bivalent Types 1 and 3 | Polio Sabin One and Three | Liquid: ready to use | GlaxoSmith Kline Biologicals SA | Federal Agency for Medicines and Health Products |
| Polio Vaccine - Oral (OPV) Bivalent Types 1 and 3 | Polio Sabin One and Three | Liquid: ready to use | GlaxoSmith Kline Biologicals SA | Federal Agency for Medicines and Health Products |
| Haemophilus influenzae type b | Haemophilus influenzae type b Conjugate Vaccine | Lyophilized active component to be reconstituted with excipient diluent before use | Serum Institute of India Pvt. Ltd. | Central Drugs Standard Control Organization |
| Polio Vaccine - Oral (OPV) Monovalent Type 1 | Monovalent type 1 Oral Poliomyelitis vaccine, IP (mOPV1) | Liquid: ready to use | Haffkine Bio Pharmaceutical Corporation Ltd | Central Drugs Standard Control Organization |
| Polio Vaccine - Oral (OPV) Monovalent Type 1 | Monovalent Oral Poliomyelitis Vaccine Type 1 (mOPV1) | Liquid: ready to use | PT Bio Farma (Persero) | National Agency of Drug and Food Control Indonesia |
| Tetanus Toxoid | None used on labelling for supply through UN agencies. Also marketed with labelled commercial name BEtt. | Liquid: ready to use | Biological E. Limited | Central Drugs Standard Control Organization |
| Pneumococcal (conjugate) | Synflorix | Liquid: ready to use | GlaxoSmith Kline Biologicals SA | European Medicines Agency |
| Diphtheria-Tetanus- Pertussis (whole cell)- Hepatitis B- Haemophilus influenzae type b | Diphtheria, Tetanus, Pertussis, Hepatitis B and Haemophilus influenzae type b Conjugate Vaccine | Lyophilized active component to be reconstituted with liquid active component before use | Serum Institute of India Pvt. Ltd. | Central Drugs Standard Control Organization |
| Polio Vaccine - Oral (OPV) Bivalent Types | Bivalent Oral Poliomyelitis | Liquid: ready to use | PT Bio Farma (Persero) | National Agency of Drug and Food Control Indonesia |

TABLE 2-continued

Approved Vaccines Containing Recall Protein Epitopes

| Type | Commercial Name | Form | Source | Responsible National Regulatory Authority |
|---|---|---|---|---|
| 1 and 3 | Vaccine Type 1&3 (bOPV 1&3) | | | |
| Meningococcal A Conjugate 10 µg | Meningococcal A Conjugate MenAfriVac | Lyophilized active component to be reconstituted with excipient diluent before use | Serum Institute of India Pvt. Ltd. | Central Drugs Standard Control Organization |
| Haemophilus influenzae type b | Quimi-Hib | Liquid: ready to use | Centro de Ingenieria Genetica y Biotecnologia | Centro para el Control Estatal de la Calidad de los Medicamentos |
| Pneumococcal (conjugate) | Synflorix | Liquid: ready to use | GlaxoSmith Kline Biologicals SA | European Medicines Agency |
| Influenza, seasonal | Fluvirin | Liquid: ready to use | Seqirus Vaccines Limited | CBER/FDA |
| Polio Vaccine - Oral (OPV) Bivalent Types 1 and 3 | Bivalent type 1&3 Oral Poliomyelitis vaccine, IP (bOPV1&3) | Liquid: ready to use | Haffkine Bio Pharmaceutical Corporation Ltd | Central Drugs Standard Control Organization |
| Influenza, seasonal | Fluzone | Liquid: ready to use | Sanofi Pasteur- USA | CBER/FDA |
| Influenza, seasonal | Fluzone | Liquid: ready to use | Sanofi Pasteur- USA | CBER/FDA |
| Diphtheria-Tetanus-Pertussis (whole cell)-Hepatitis B-Haemophilus influenzae type b | Diphtheria, Tetanus, Pertussis, Hepatitis B and Haemophilus influenzae type b Conjugate Vaccine | Lyophilized active component to be reconstituted with liquid active component before use | Serum Institute of India Pvt. Ltd. | Central Drugs Standard Control Organization |
| Influenza, seasonal | GCFLU Multi inj. | Liquid: ready to use | Green Cross Corporation | Ministry of Food and Drug Safety |
| Diphtheria-Tetanus-Pertussis (whole cell)-Hepatitis B-Haemophilus influenzae type b | Diphtheria, Tetanus, Pertussis, Hepatitis B and Haemophilus influenzae type b Conjugate Vaccine | Lyophilized active component to be reconstituted with liquid active component before use | Serum Institute of India Pvt. Ltd. | Central Drugs Standard Control Organization |
| Influenza, pandemic H1N1 | Panvax | Liquid: ready to use | Seqirus Limited | Therapeutic Goods Administration |
| Influenza, pandemic H1N1 | Green Flu-S | Liquid: ready to use | Green Cross Corporation | Ministry of Food and Drug Safety |
| Influenza, pandemic H1N1 | Influenza A (H1N1) 2009 monovalent vaccine | Liquid: ready to use | MedImmune | CBER/FDA |
| Influenza, pandemic H1N1 | Celtura | Liquid: ready to use | Seqirus GmbH | Paul-Ehrlich-Institut |
| Influenza, pandemic H1N1 | Focetria | Liquid: ready to use | Seqirus Vaccines Limited | |
| Influenza, pandemic H1N1 | Fluvirin-H1N1 | Liquid: ready to use | Seqirus Vaccines Limited | CBER/FDA |
| Influenza, pandemic H1N1 | Panenza | Liquid: ready to use | Sanofi Pasteur SA | Agence nationale de sécurité du médicament et des produits de santé |
| Influenza, pandemic H1N1 | Influenza A (H1N1) 2009 monovalent vaccine | Liquid: ready to use | Sanofi Pasteur- USA | CBER/FDA |
| Influenza, pandemic H1N1 | Influenza A (H1N1) 2009 monovalent vaccine | Liquid: ready to use | Sanofi Pasteur- USA | CBER/FDA |
| Diphtheria-Tetanus-Pertussis (whole cell)-Haemophilus influenzae type b | Diphtheria, Tetanus, Pertussis and Haemophilus influenzae type b Conjugate Vaccine | Lyophilized active component to be reconstituted with liquid active component before use | Serum Institute of India Pvt. Ltd. | Central Drugs Standard Control Organization |

TABLE 2-continued

Approved Vaccines Containing Recall Protein Epitopes

| Type | Commercial Name | Form | Source | Responsible National Regulatory Authority |
|---|---|---|---|---|
| Polio Vaccine - Inactivated (IPV) | Poliorix | Liquid: ready to use | GlaxoSmith Kline Biologicals SA | Federal Agency for Medicines and Health Products |
| Polio Vaccine - Inactivated (IPV) | Poliorix | Liquid: ready to use | GlaxoSmith Kline Biologicals SA | Federal Agency for Medicines and Health Products |
| Pneumococcal (conjugate) | Prevenar 13 | Liquid: ready to use | Pfizer | European Medicines Agency |
| Diphtheria-Tetanus-Pertussis (whole cell)-Hepatitis B-Haemophilus influenzae type b | Diphtheria, Tetanus, Pertussis, Hepatitis B and Haemophilus influenzae type b Conjugate Vaccine Adsorbed | Liquid: ready to use | Serum Institute of India Pvt. Ltd. | Central Drugs Standard Control Organization |
| Diphtheria-Tetanus-Pertussis (whole cell)-Hepatitis B-Haemophilus influenzae type b | Diphtheria, Tetanus, Pertussis, Hepatitis B and Haemophilus influenzae type b Conjugate Vaccine Adsorbed | Liquid: ready to use | Serum Institute of India Pvt. Ltd. | Central Drugs Standard Control Organization |
| Diphtheria-Tetanus-Pertussis (whole cell)-Hepatitis B-Haemophilus influenzae type b | Diphtheria, Tetanus, Pertussis, Hepatitis B and Haemophilus influenzae type b Conjugate Vaccine Adsorbed | Liquid: ready to use | Serum Institute of India Pvt. Ltd. | Central Drugs Standard Control Organization |
| Polio Vaccine - Oral (OPV) Monovalent Type 3 | Polio Sabin Mono Three (oral) | Liquid: ready to use | GlaxoSmith Kline Biologicals SA | Federal Agency for Medicines and Health Products |
| Polio Vaccine - Oral (OPV) Monovalent Type 3 | Polio Sabin Mono Three (oral) | Liquid: ready to use | GlaxoSmith Kline Biologicals SA | Federal Agency for Medicines and Health Products |
| Polio Vaccine - Inactivated (IPV) | Poliomyelitis vaccine | Liquid: ready to use | Bilthoven Biologicals | Medicines Evaluation Board (MEB) |
| Polio Vaccine - Inactivated (IPV) | IPV Vaccine SSI | Liquid: ready to use | AJ Vaccines A/S | Danish Medicines Agency |
| Influenza, seasonal | GC FLU inj | Liquid: ready to use | Green Cross Corporation | Ministry of Food and Drug Safety |
| Polio Vaccine - Oral (OPV) Monovalent Type 2 | Polio Sabin Mono Two (oral) | Liquid: ready to use | GlaxoSmith Kline Biologicals SA | Federal Agency for Medicines and Health Products |
| Polio Vaccine - Oral (OPV) Monovalent Type 2 | Polio Sabin Mono Two (oral) | Liquid: ready to use | GlaxoSmith Kline Biologicals SA | Federal Agency for Medicines and Health Products |
| Typhoid (Polysaccharide) | Typhim-Vi | Liquid: ready to use | Sanofi Pasteur SA | Agence nationale de sécurité du médicament et des produits de santé |
| Influenza, seasonal | Vaxigrip | Liquid: ready to use | Sanofi Pasteur SA | Agence nationale de sécurité du médicament et des produits de santé |
| Polio Vaccine - Oral (OPV) Bivalent Types 1 and 3 | BIOPOLIO B1/3 | Liquid: ready to use | Bharat Biotech International Limited | Central Drugs Standard Control Organization |
| Diphtheria-Tetanus (reduced antigen content) | none | Liquid: ready to use | PT Bio Farma (Persero) | National Agency of Drug and Food Control Indonesia |
| Polio Vaccine - Oral (OPV) Bivalent Types 1 and 3 | none | Liquid: ready to use | Sanofi Pasteur SA | Agence nationale de sécurité du médicament et des produits de santé |
| Diphtheria-Tetanus-Pertussis (whole cell)-Hepatitis B-Haemophilus influenzae type b | None used on labelling for supply through UN agencies. Also marketed with labelled | Lyophilized active component to be reconstituted with liquid active component before use | Biological E. Limited | Central Drugs Standard Control Organization |

TABLE 2-continued

Approved Vaccines Containing Recall Protein Epitopes

| Type | Commercial Name | Form | Source | Responsible National Regulatory Authority |
|---|---|---|---|---|
| Diphtheria-Tetanus-Pertussis (whole cell)-Hepatitis B-Haemophilus influenzae type b | commercial name ComBE Five (Reconstituted). None used on labelling for supply through UN agencies. Also marketed with labelled commercial name ComBE Five (Reconstituted). | Lyophilized active component to be reconstituted with liquid active component before use | Biological E. Limited | Central Drugs Standard Control Organization |
| cholera: inactivated oral | Shanchol | Liquid: ready to use | Shantha Biotechnics Private Limited (A Sanofi Company) | Central Drugs Standard Control Organization |
| Measles, Mumps and Rubella | Priorix | Lyophilized active component to be reconstituted with excipient diluent before use | GlaxoSmith Kline Biologicals SA | Federal Agency for Medicines and Health Products |
| Measles | Measles vaccine | Lyophilized active component to be reconstituted with excipient diluent before use | PT Bio Farma (Persero) | National Agency of Drug and Food Control Indonesia |
| Polio Vaccine - Oral (OPV) Bivalent Types 1 and 3 | Poliomyelitis Vaccine (Oral), Bivalent types 1 and 3 | Liquid: ready to use | Serum Institute of India Pvt. Ltd. | Central Drugs Standard Control Organization |
| Influenza, pandemic H1N1 | NASOVAC Influenza Vaccine, Live Attenuated (Human) Freeze-Dried | Lyophilized active component to be reconstituted with excipient diluent before use | Serum Institute of India Pvt. Ltd. | Central Drugs Standard Control Organization |
| Influenza, pandemic H1N1 | NASOVAC Influenza Vaccine, Live Attenuated (Human) Freeze-Dried | Lyophilized active component to be reconstituted with excipient diluent before use | Serum Institute of India Pvt. Ltd. | Central Drugs Standard Control Organization |
| Tetanus Toxoid | None used on labelling for supply through UN agencies. Also marketed with labelled commercial name BEtt. | Liquid: ready to use | Biological E. Limited | Central Drugs Standard Control Organization |
| Tetanus Toxoid | None used on labelling for supply through UN agencies. Also marketed with labelled commercial name BEtt. | Liquid: ready to use | Biological E. Limited | Central Drugs Standard Control Organization |
| Japanese Encephalitis Vaccine (Inactivated) 6 µg | JEEV ® | Liquid: ready to use | Biological E. Limited | Central Drugs Standard Control Organization |
| Hepatitis A (Human Diploid Cell), Inactivated (Adult) | Havrix 1440 Adult | Liquid: ready to use | GlaxoSmith Kline Biologicals SA | Federal Agency for Medicines and Health Products |
| Hepatitis A (Human Diploid Cell), Inactivated (Paediatric) | Havrix 720 Junior | Liquid: ready to use | GlaxoSmith Kline Biologicals SA | Federal Agency for Medicines and Health Products |
| Diphtheria-Tetanus-Pertussis (acellular) | Boostrix | Liquid: ready to use | GlaxoSmith Kline Biologicals SA | Federal Agency for Medicines and Health Products |
| Meningococcal ACYW-135 (conjugate vaccine) | Menveo | Lyophilized active component to be reconstituted with liquid active component before use | GlaxoSmith Kline Vaccines S.r.l. | European Medicines Agency |

TABLE 2-continued

Approved Vaccines Containing Recall Protein Epitopes

| Type | Commercial Name | Form | Source | Responsible National Regulatory Authority |
|---|---|---|---|---|
| Meningococcal ACYW-135 (conjugate vaccine) | Menactra | Liquid: ready to use | Sanofi Pasteur-USA | CBER/FDA |
| Diphtheria-Tetanus-Pertussis (whole cell)-Hepatitis B-Haemophilus influenzae type b | Easyfive-TT | Liquid: ready to use | Panacea Biotec Ltd. | Central Drugs Standard Control Organization |
| Japanese Encephalitis Vaccine (live, attenuated) | Japanese Encephalitis Vaccine Live (SA14-14-2) | Lyophilized active component to be reconstituted with excipient diluent before use | Chengdu Institute of Biological Products Co., Ltd | National Medical Products Administration |
| Japanese Encephalitis Vaccine (live, attenuated) | Japanese Encephalitis Vaccine Live (SA14-14-2) | Lyophilized active component to be reconstituted with excipient diluent before use | Chengdu Institute of Biological Products Co., Ltd | National Medical Products Administration |
| Diphtheria-Tetanus-Pertussis (whole cell)-Hepatitis B-Haemophilus influenzae type b | None used on labelling for supply through UN agencies. Also marketed with labelled commercial name ComBE Five (Liquid). | Liquid: ready to use | Biological E. Limited | Central Drugs Standard Control Organization |
| Diphtheria-Tetanus-Pertussis (whole cell)-Hepatitis B-Haemophilus influenzae type b | None used on labelling for supply through UN agencies. Also marketed with labelled commercial name ComBE Five (Liquid). | Liquid: ready to use | Biological E. Limited | Central Drugs Standard Control Organization |
| Japanese Encephalitis Vaccine (live, attenuated) | IMOJEV MD | Lyophilized active component to be reconstituted with excipient diluent before use | GPO-MBP Co., Ltd. | Thai Food and Drug Administration |
| Diphtheria-Tetanus-Pertussis (whole cell) | None used on labelling for supply through UN agencies. Also marketed with labelled commercial name TRIPVAC | Liquid: ready to use | Biological E. Limited | Central Drugs Standard Control Organization |
| Diphtheria-Tetanus-Pertussis (whole cell) | None used on labelling for supply through UN agencies. Also marketed with labelled commercial name TRIPVAC | Liquid: ready to use | Biological E. Limited | Central Drugs Standard Control Organization |
| Diphtheria-Tetanus (reduced antigen content) | None used on labelling for supply through UN agencies. Also marketed with labelled commercial name BE Td | Liquid: ready to use | Biological E. Limited | Central Drugs Standard Control Organization |
| Diphtheria-Tetanus (reduced antigen content) | None used on labelling for supply through UN agencies. Also marketed with labelled commercial name BE Td | Liquid: ready to use | Biological E. Limited | Central Drugs Standard Control Organization |
| Polio Vaccine - Oral (OPV) Bivalent Types | Poliomyelitis Vaccine (Oral), | Liquid: ready to use | Serum Institute of India Pvt. | Central Drugs Standard Control Organization |

TABLE 2-continued

Approved Vaccines Containing Recall Protein Epitopes

| Type | Commercial Name | Form | Source | Responsible National Regulatory Authority |
|---|---|---|---|---|
| 1 and 3 | Bivalent types 1 and 3 | | Ltd. | |
| Polio Vaccine - Inactivated (IPV) | Poliomyelitis vaccine multidose, suspension for injection 2.5 mL | Liquid: ready to use | Bilthoven Biologicals | Medicines Evaluation Board (MEB) |
| Influenza, seasonal | Nasovac-S Influenza Vaccine, Live, Attenuated (Human) | Lyophilized active component to be reconstituted with excipient diluent before use | Serum Institute of India Pvt. Ltd. | Central Drugs Standard Control Organization |
| Diphtheria-Tetanus-Pertussis (acellular)-Hepatitis B-Haemophilus influenzae type b-Polio (Inactivated) | Hexaxim | Liquid: ready to use | Sanofi Pasteur SA | European Medicines Agency |
| Meningococcal A Conjugate 5 μg | Meningococcal A Conjugate 5 micrograms MenAfriVac 5 μg | Lyophilized active component to be reconstituted with excipient diluent before use | Serum Institute of India Pvt. Ltd. | Central Drugs Standard Control Organization |
| Diphtheria-Tetanus-Pertussis (whole cell)-Hepatitis B-Haemophilus influenzae type b | None used on labelling for supply through UN agencies. Also marketed with labelled commercial name ComBE Five (Liquid). | Liquid: ready to use | Biological E. Limited | Central Drugs Standard Control Organization |
| Diphtheria-Tetanus-Pertussis (whole cell)-Hepatitis B-Haemophilus influenzae type b | None used on labelling for supply through UN agencies. Also marketed with labelled commercial name ComBE Five (Liquid). | Liquid: ready to use | Biological E. Limited | Central Drugs Standard Control Organization |
| Polio Vaccine - Inactivated (IPV) | Poliomyelitis Vaccine (Inactivated) | Liquid: ready to use | Serum Institute of India Pvt. Ltd. | Central Drugs Standard Control Organization |
| Polio Vaccine - Oral (OPV) Trivalent | BIOPOLIO | Liquid: ready to use | Bharat Biotech International Limited | Central Drugs Standard Control Organization |
| Polio Vaccine - Oral (OPV) Trivalent | BIOPOLIO | Liquid: ready to use | Bharat Biotech International Limited | Central Drugs Standard Control Organization |
| Influenza, seasonal | Influenza Vaccine (Split virion, inactivated) | Liquid: ready to use | Hualan Biological Bacterin Co., Ltd | National Medical Products Administration |
| Influenza, seasonal | IL-YANG FLU Vaccine INJ. | Liquid: ready to use | IL-YANG PHARMACEUTICAL CO., LTD. | Ministry of Food and Drug Safety |
| BCG | BCG vaccine (Freeze Dried) - Intradermal | Lyophilized active component to be reconstituted with excipient diluent before use | GreenSignal Bio Pharma Limited | Central Drugs Standard Control Organization |
| Influenza, seasonal Quadrivalent | Fluzone Quadrivalent | Liquid: ready to use | Sanofi Pasteur-USA | CBER/FDA |
| Influenza, seasonal Quadrivalent | Fluzone Quadrivalent | Liquid: ready to use | Sanofi Pasteur-USA | CBER/FDA |
| Polio Vaccine - Oral (OPV) Bivalent Types 1 and 3 | Bivalent Oral Poliomyelitis Vaccine Type 1&3 (bOPV 1&3) | Liquid: ready to use | PT Bio Farma (Persero) | National Agency of Drug and Food Control Indonesia |
| cholera: inactivated oral | Euvichol | Liquid: ready to use | EuBiologics Co., Ltd. | Ministry of Food and Drug Safety |
| Polio Vaccine - Oral (OPV) Monovalent Type 2 | ORAL MONOVALENT TYPE 2 POLIOMYELITIS | Liquid: ready to use | Sanofi Pasteur SA | Agence nationale de sécurité du médicament et des |

TABLE 2-continued

Approved Vaccines Containing Recall Protein Epitopes

| Type | Commercial Name | Form | Source | Responsible National Regulatory Authority |
|---|---|---|---|---|
| | VACCINE (mOPV2) | | | produits de santé |
| Polio Vaccine - Oral (OPV) Monovalent Type 3 | ORAL MONOVALENT TYPE 3 POLIOMYELITIS VACCINE | Liquid: ready to use | Sanofi Pasteur SA | Agence nationale de sécurité du médicament et des produits de santé |
| Meningococcal ACYW-135 (conjugate vaccine) | Nimenrix | Lyophilized active component to be reconstituted with excipient diluent before use | Pfizer | European Medicines Agency |
| Diphtheria-Tetanus-Pertussis (whole cell)-Hepatitis B-Haemophilus influenzae type b | Eupenta | Liquid: ready to use | LG Chem Ltd | Ministry of Food and Drug Safety |
| Diphtheria-Tetanus-Pertussis (whole cell)-Hepatitis B-Haemophilus influenzae type b | Eupenta | Liquid: ready to use | LG Chem Ltd | Ministry of Food and Drug Safety |
| Human Papillomavirus (Ninevalent) | Gardasil 9 | Liquid: ready to use | Merck Vaccines | European Medicines Agency |
| Influenza, seasonal Quadrivalent | GCFLU Quadrivalent inj. | Liquid: ready to use | Green Cross Corporation | Ministry of Food and Drug Safety |
| Diphtheria-Tetanus-Pertussis (whole cell)-Hepatitis B-Haemophilus influenzae type b | Pentabio | Liquid: ready to use | PT Bio Farma (Persero) | National Agency of Drug and Food Control Indonesia |
| Diphtheria-Tetanus-Pertussis (whole cell)-Hepatitis B-Haemophilus influenzae type b | Pentabio | Liquid: ready to use | PT Bio Farma (Persero) | National Agency of Drug and Food Control Indonesia |
| Hepatitis A (Human Diploid Cell), Inactivated (Adult) | HEALIVE | Liquid: ready to use | Sinovac Biotech Co. Ltd | National Medical Products Administration |
| Varicella | Varivax | Lyophilized active component to be reconstituted with excipient diluent before use | Merck Vaccines | CBER/FDA |
| Rotavirus (live, attenuated) | Rotavac | Liquid: ready to use | Bharat Biotech International Limited | Central Drugs Standard Control Organization |
| Diphtheria-Tetanus-Pertussis (acellular) | Adacel | Liquid: ready to use | Sanofi Pasteur Limited | Health Canada - Sante Canada |
| Influenza, seasonal | AGRIFLU | Liquid: ready to use | Seqirus Vaccines Limited | Health Canada - Sante Canada |
| Pneumococcal (conjugate) | Prevenar 13 Multidose Vial | Liquid: ready to use | Pfizer | European Medicines Agency |
| Typhoid (Conjugate) | Typbar-TVC | Liquid: ready to use | Bharat Biotech International Limited | Central Drugs Standard Control Organization |
| Polio Vaccine - Oral (OPV) Bivalent Types 1 and 3 | Poliomyelitis Vaccine (live, oral attenuated, human Diploid Cell), type 1 and 3 | Liquid: ready to use | Beijing Bio-Institute Biological Products Co., Ltd | National Medical Products Administration |
| Japanese Encephalitis Vaccine (Inactivated) (3 µg Pediatric) | JEEV ® | Liquid: ready to use | Biological E. Limited | Central Drugs Standard Control Organization |
| Rotavirus (live, attenuated) | ROTASIIL | Lyophilized active component to be reconstituted with excipient diluent before use | Serum Institute of India Pvt. Ltd. | Central Drugs Standard Control Organization |
| Polio Vaccine - Inactivated (IPV) | Poliomyelitis Vaccine (Inactivated) | Liquid: ready to use | Serum Institute of India Pvt. Ltd. | Central Drugs Standard Control Organization |

TABLE 2-continued

Approved Vaccines Containing Recall Protein Epitopes

| Type | Commercial Name | Form | Source | Responsible National Regulatory Authority |
|---|---|---|---|---|
| Polio Vaccine - Inactivated (IPV) | Poliomyelitis Vaccine (Inactivated) | Liquid: ready to use | Serum Institute of India Pvt. Ltd. | Central Drugs Standard Control Organization |
| Influenza, seasonal Quadrivalent | GCFLU Quadrivalent Multi inj. | Liquid: ready to use | Green Cross Corporation | Ministry of Food and Drug Safety |
| Influenza, seasonal | Serinflu | Liquid: ready to use | Abbott Biologicals BV | Medicines Evaluation Board (MEB) |
| Polio Vaccine - Inactivated (IPV) | ShanIPV | Liquid: ready to use | Shantha Biotechnics Private Limited (A Sanofi Company) | Central Drugs Standard Control Organization |
| Polio Vaccine - Oral (OPV) Bivalent Types 1 and 3 | Bivalent OPV Type 1 and 3 Poliomyelitis Vaccine, Live (Oral) | Liquid: ready to use | Panacea Biotec Ltd. | Central Drugs Standard Control Organization |
| cholera: inactivated oral | Euvichol - Plus | Liquid: ready to use | EuBiologics Co., Ltd. | Ministry of Food and Drug Safety |
| Polio Vaccine - Oral (OPV) Bivalent Types 1 and 3 | BIOPOLIO B1/3 | Liquid: ready to use | Bharat Biotech International Limited | Central Drugs Standard Control Organization |
| BCG | BCG Freeze Dried Glutamate vaccine | Lyophilized active component to be reconstituted with excipient diluent before use | Japan BCG Laboratory | Chiba Local Government |
| Pneumococcal (conjugate) | Synflorix | Liquid: ready to use | GlaxoSmith Kline Biologicals SA | European Medicines Agency |
| Rotavirus (live, attenuated) | Rotavac | Liquid: ready to use | Bharat Biotech International Limited | Central Drugs Standard Control Organization |
| Hepatitis A (Human Diploid Cell), Inactivated (Paediatric) | HEALIVE | Liquid: ready to use | Sinovac Biotech Co. Ltd | National Medical Products Administration |
| Typhoid (Conjugate) | Typbar-TVC | Liquid: ready to use | Bharat Biotech International Limited | Central Drugs Standard Control Organization |
| Rotavirus (live, attenuated) | ROTASIIL | Lyophilized active component to be reconstituted with excipient diluent before use | Serum Institute of India Pvt. Ltd. | Central Drugs Standard Control Organization |
| Japanese Encephalitis Vaccine (Inactivated) 6 µg | JEEV ® | Liquid: ready to use | Biological E. Limited | Central Drugs Standard Control Organization |
| Japanese Encephalitis Vaccine (Inactivated) (3 µg Pediatric) | JEEV ® | Liquid: ready to use | Biological E. Limited | Central Drugs Standard Control Organization |

In various embodiments, the recall protein epitope is released following proteolytic cleavage and the epitope binds to an MHC class I molecule. The MHC class I molecule may be from the HLA-A, B, and/or C families. The specific epitope that binds to the MHC class I molecule may be any of those recited in Table 1 or Table 2. The MHC class I molecule itself may be, one or more of the following non-limiting examples: HLA-A*02:01, HLA-A*03:01, HLA-A*11:01, HLA-A*201, HLA-A*020101, HLA-A*0203, HLA-A*0206, HLA-A2, HLA-A2.1, or HLA-A*02.

In an aspect of the invention the recall protein is about 8 amino acid to about 50 amino acids in length, or about 8 amino acid to about 45 amino acids in length, or about 8 amino acid to about 40 amino acids in length, about 8 amino acid to about 35 amino acids in length, or about 8 amino acid to about 30 amino acids in length, about 8 amino acid to about 25 amino acids in length, about 8 amino acid to about 20 amino acids in length, or is about 8 amino acid to about 15 amino acids in length. In an aspect of the invention the fusion protein is about 13 amino acid to about 50 amino acids in length, or about 13 amino acid to about 45 amino acids in length, or about 13 amino acid to about 40 amino acids in length, about 13 amino acid to about 35 amino acids in length, or about 13 amino acid to about 30 amino acids in length, about 13 amino acid to about 25 amino acids in length, about 13 amino acid to about 20 amino acids in length, or is about 13 amino acid to about 15 amino acids in length. In an aspect of the invention the CD8+ T cell epitope may be, e.g., 8, 9, 10, 11, 12, 13, 14, 15, 16, or 17 amino acids in length.

Cleavage Sequence.

In various embodiments, a cleavage sequence is provided that allows the recall protein to be released from the VLP so that the recall protein can bind to the MHC on the tumor cell surface. In various embodiments, the VLP must escape the endosome, disassemble, and release their therapeutic cargo to the cytosol in a functional form. In various embodiments the conjugated VLP and/or fusion protein of the conjugated VLP is susceptible to cleavage by a proteolytic enzyme within the tumor cell and the position of the target cleavage sequence in the VLP or fusion protein is such that the cleave of the target site releases all or a portion of the recall protein comprising the CD8+ T cell epitope from the conjugated VLP, which complexes with an MHC class 1 molecule of the tumor cell. Sufficient amounts of conjugated VLP are readily determined by the skilled artisan and it will be appreciated that the amount will depend on, e.g., the characteristics of the subject, e.g., age, weight, gender, and/or medical condition of the subject, and the characteristics of the tumor, e.g., type, volume, and developmental status.

The cleavage sequence may be recognized by any protease present in a cell. At least 569 known proteases have been described (see, Lopez-Otin, et al., *Nature Reviews Cancer*, 7(10):800-808, 2007). All identified human proteolytic enzymes are classified into five catalytic classes: metalloproteinases, serine, threonine, cysteine and aspartic proteases. A non-limiting list of potential proteases that could be targeted is demonstrated in Table 3, which is a table summarizing the most well studied proteases distributed into five broad classes (in order from greatest to least number): metalloproteinases, serine, cysteine, threonine, and aspartic proteases. Several of these proteases have been found to be over-expressed in cancer cells relative to health cells.

In various embodiments, the cleavage sequence is recognized by the protease furin, a matrix metalloproteinases (MMPs), e.g., MMP, 1, 2, 3, 7, 8, 9, 11, 13, 14, or 19, an ADAM (a disintegrin and metalloproteinase), e.g., ADAMS 8, 9, 10, 15, 17, or 28, a cathepsin, e.g., cathepsin D, G, H, or N. Elastase, proteinase-3, azurocidin, or ADAMTS-1. In various embodiments, the cleavage sequence is recognized by a furin protease. In various embodiments, the cleavage sequence comprises at least 4 amino acid residues, at least three of which are arginine residues. In various embodiments, the cleavage sequence comprises at least 4 amino acid residues, at least three of which are arginine residues and one of which is either a lysine residue or an arginine residue. In various embodiments, the cleavage sequence is R-X-R/K-R. In various embodiments, the cleavage sequence comprises additional residues. In various embodiments, the cleavage sequence further comprises 1, 2, 3, 4, 5, 6, 7, 8, or 9 additional arginine residues. It is known that arginines are positively charged, and a longer chain of positive charged Arginine residues will bring the peptides closer to the surface of the VLP which is more negatively charged.

TABLE 3

Proteases and cancers associated with overexpressed proteases

| Family | Protease | Location | Cancer | Ref. | Other Diseases | Ref. |
|---|---|---|---|---|---|---|
| Cysteine Cathepsins | General | Intracellular, lysosomes | Most | Table in [121] | | |
| | Cathepsin K | Extracellular, bone | Breast | [178] | Artherosclerosis, osteoporosis | [179-182] |
| | Cathepsin B | Extracellular and pericellular under pathological conditions | Breast, cervix, colon, colorectal, gastric, head and neck, liver, lung, melanoma, ovarian, pancreatic, prostate, thyroid | [31, 38, 81, 183-196] | | |
| | Cathepsin L | | Breast, colorectal | [28] | AD | [197] |
| Aspartic Cathepsins | Cathepsin E | Endosomal structures, ER, Golgi | Cervical, gastric, lung, pancreas adenocarcinomas | [51-55] | | |
| | Cathepsin D | Lysosome | Breast, colorectal, ovarian | [47-49, 198-200] | Atherosclerosis | [121] |
| | General | Intracellular, secreted | Most | Table in [15, 58] | | |
| Kallikreins (hK) | hK1 | | | | Hypertension, inflammation | [24] |
| | PSA (hK 3) | | Prostate, ovarian | [201-202] | | |
| | hK10 | | Colon, ovarian, pancreatic, head and neck | [203-206] | | |
| | hK15 | | Ovarian, prostate | [207-208] | | |
| Serine Proteases | uPA, uPAR | Membrane, Pericellular | Cervical, colorectal, gastric, prostate | [86, 116, 209-210] | | |
| Caspases | | Intracellular | | | Neurodegenerative disorders | [82] |
| | General | Extracellular | Most | Table in [211] | | |
| MMPs | MMP-1, -8, -13 | | Breast | [85, 102-104, 211-212] | Artherosclerosis, RA | [213-214] |
| | MMP-2, -9 | | Breast, colorectal, lung, malignant gliomas, ovarian | [91-94][95-98] | Bronchiectasis, chronic asthma, COPD, cystic fibrosis, HIV associated dementia, hypertension, stroke | [87, 113-117] |
| | MMP-14 | Membrane | Breast | [212] | | |
| ADAM | | Extracellular | | | AD | [105, 107, 112] |

*Abbreviations:
AD: Alzheimer's disease;
ADAM: a disintegrin and metalloproteinase domain protease;
COPD: chronic obstructive pulmonary disease;
ER: endoplasmic reticulum;
RA: rheumatoid arthritis In various embodiments, the fusion protein must be bound to the capsid proteins of the VLP. There are multiple methods of binding the fusion protein to the capsid protein. In various embodiments of the present invention the cleavage sequence is conjugated through a maleimide linkage or an amide linkage (discussed below). The fusion protein may be linked to any residue on the capsid protein of the VLP; however, disulfide linkages, maleimide linkages, and amide linkages are formed by conjugating the recall protein to cysteine, lysine, or arginine residues.

Surface Functionalization of the VLP

The VLPs described herein must be functionalized to deliver a recall protein, which must be presented on the surface of the conjugated VLP. In various embodiments, recall proteins may be conjugated to the VLP through cysteine residues on the capsid protein. Such cysteine molecule can be presented naturally, or by mutation on the surface of the VLP. In various embodiments, the VLP is subjected to reducing conditions sufficient to reduce the sulfhydryl groups of cysteine residues on the surface of the VLP while maintaining the capsid-like icosahedron structures of the VLP. Because of its free sulfhydryl group, cysteine will readily and spontaneously form disulfide bonds with other sulfhydryl-containing ligands under oxidative conditions. Alternatively, a series of compounds add on maleimide readily and irreversibly form thioester linkages with cysteine residues at a pH between 6.5 and 7.5.

In various embodiments, the fusion protein may also be conjugated to a lysine residue on the VLP. Lysine residues are easily modified because of its primary amine. Using reactions termed n-hydroxysuccinimide (NHS) ester reactions (because NHS is released as part of the reaction), amide bonds are formed at surface-exposed lysine residues. The reaction occurs spontaneously between pH 7.2 and pH 9. This attachment chemistry has been used to display transferrin on MS2, which may allow the VLP to transcytose the blood-brain barrier that could open up a new library of therapies for neurological disorders.

In various embodiments, the fusion protein may also be conjugated to an aspartate- or glutamate residue. Unlike strategies involving cysteine and lysine, coupling to these residues requires multiple steps. First, the carboxylic acid must be activated using 1-ethyl-3-(3-dimethylaminopropyl) carbodiimide hydrochloride (EDC). Once activated, it will react with NHS to form an NHS ester. Now that the carboxylic acid side-chain has essentially become an NHS ester, a ligand with an exposed primary amine can be used to from a stable amide bond.

In various embodiments, the VLP comprises a region of negatively charged amino acids on a surface exposed area that is capable of binding to the fusion protein comprising a region of positively charged amino acids. In various embodiments, the region of negatively charged amino acids may be flanked, on one or on both sides, by one or more cysteine residues, referred to as polyanionic: cysteine or more specifically, polyglutamic acid:cysteine or polyaspartic acid: cysteine. In such cases, the conjugation of the VLP and the fusion protein would result from non-covalent binding between the complementary amino acid charges of the VLP and the fusion protein and a disulfide bond between the cysteines. In various embodiments, the cysteine(s) are one or more amino acids away from the region of charged amino acids such that any secondary/tertiary structure would bring the charged amino acid region in close proximity to the cysteine(s). In various embodiments of the invention the fusion protein comprises at least one recall protein and a polyionic:cysteine for attaching the fusion protein to the VLP comprising a complementary polyionic:cysteine sequence and an enzyme cleavage site positioned between the terminal cysteine and the CD8+ T cell epitope. In various embodiments, the fusion protein comprises, a terminal cysteine, at least one recall protein, and an enzyme cleavage sequence positioned between the terminal cysteine and the recall protein(s).

Negatively charged amino acids that can be used in producing the conjugated VLP include, e.g., glutamic acid and aspartic acid. These amino acids can be used singly, e.g., polyglutamic acid, or in combination. In a specific embodiment, the region comprises glutamic acid. The number of negatively charged amino acids can vary, and can include about 4 to about 20 amino acids, about 6 to about 18 amino acids, or about 8 to about 16 amino acids, and the like. In a specific embodiment, the region comprises about 8 negatively charged amino acids. In a more specific embodiment, the region comprises EEEEEEEEC (E8C) (SEQ ID NO: 84). In another embodiment, the region comprises CEEEEEEEEC (SEQ ID NO: 85). Methods for conjugating fusion proteins to a VLPs via disulfide bonding are known. For instance, the presence of a polyargininecysteine moiety on the fusion protein allows docking of the peptide to the polyanionic site (EEEEEEEEC, E8C, SEQ ID NO: 84) present in the various loops of the L1 particles. Covalent cross-linking between the two cysteine residues should render this association irreversible under oxidizing conditions. For the conjugation reactions, purified HPV particles are dialyzed in conjugation buffer (20 mM Tris/HCl pH=7.5, 150 mM NaCl, 5% glycerol, 0.5 mM $CaCl_2$) and then the peptide and the oxidizing reagents are added, allowing the reaction to proceed for 16 hrs at 4° C. At the end of the incubation, the reaction mixtures are applied to a size-exclusion column (SEPHADEX® G-100, Pharmacia, New Jersey, US, volume 20 ml, flow rate 1 ml/min, 10 mM Tris/HCl (pH=7.4), 150 mM NaCl, 0.5 mM $CaCl_2$) to remove unconjugated peptide and exchange buffer. Conjugated particles that elute in the void volume are identified by the presence of the L1 protein on SDS-PAGE. The conjugated particles are analyzed by electron microscopy. One of ordinary skill in the art can, through routine experimentation, create a VLP that includes a polyionic region in a surface exposed area, e.g., one or more loops, and that is VLP assembly competent.

In various embodiments, the fusion protein is genetically fused to the coat protein. In various embodiments, the fusion protein may be either covalently or non-covalently linked to the VLP. Rather than attaching the recall protein to the VLP via, e.g., binding of negatively and positively charged amino acids, or via maleimide based conjugation, a nucleic acid sequence encoding the fusion protein may be inserted into the nucleic acid encoding the capsid protein such that upon expression, a fusion protein is produced wherein the recall protein is inserted into a loop of the capsid protein and displayed on the surface of the VLP.

In various embodiments, non-natural amino acids may be used to conjugate the fusion protein to the VLP. Beyond the 20 natural amino acids, many non-natural amino acids have been used for site-specific protein conjugation reactions. For example, an azidohomoalanine (AHA) or a p-amino-phenylalanine (pAF) may be incorporated into the VLP coat protein for conjugation. These amino acids are incorporated into proteins in two ways: global methionine replacement and amber stop codon suppression. Because AHA is very similar to methionine, AHA will be incorporated at each AUG codon if the methionine supply is rate limiting, this is termed global methionine replacement. Bacteria auxotrophic for methionine or cell-free protein synthesis can be used to limit-methionine availability. Amber stop codon suppression will incorporate pAF. Amber stop codon suppression uses nonnative synthetases and tRNAs that do not react with the natural amino acids to incorporate the non-natural amino acid at the amber stop codon UAG. AHA, displaying an azide, will participate in in copper(I)-catalyzed azide-alkyne cycloaddition ("click" reaction) and form covalent triazole rings with alkyne-containing ligands.

In various embodiments, the conjugated VLP comprises, at least one-tenth of the viral coat proteins may display a recall protein. In various embodiments, at least one-fifth of the viral coat proteins may display a recall protein. In various embodiments, about half of the viral coat proteins may display a recall protein. In various embodiments, about two-thirds of the viral coat proteins may display a recall peptide. In various embodiments, nearly all of the viral coat proteins may display a recall protein.

Methods of Treatment

In various embodiments of the invention, a method for treating a cancer in a subject in need thereof by administering a conjugated VLP to patient in need thereof. The methods of this invention comprise administering the conjugated VLPs of this invention to a subject in need thereof in an amount sufficient to inhibit tumor growth, progression or metastasis. In various embodiments of the invention, the conjugated VLP is administered to a subject in need thereof in amount sufficient to stimulate cytokine production and/or cellular immunity, particularly innate immunity, including stimulating the cytotoxic activity of macrophages and natural killer cells. In various embodiments of this invention a subject in need thereof is a subject who has been previously treated for a tumor and is currently deemed cancer-free or disease free in accordance with medical standards.

Briefly, the mechanism of action of the described conjugated VLPs is depicted in FIG. 1. The VLPs specifically bind to a tumor cell. (FIG. 1, left side, tumor cells). The recall protein epitope on the VLP is then proteolytically cleaved by furin, which is over-expressed in the tumor microenvironment. This in turn leads to release of the epitope from the conjugated VLP and the loading of the epitopes onto the tumor MHC class 1 molecules ("epitope coating"). (FIG. 1, middle exploded view showing block MHI molecule loading with epitope from VLP). The epitope-coated tumor cell is then recognized as a pathogen-infected cell by one or more childhood vaccine T-cells and pre-existing CD8 T cells, yielding a triggered immune redirection response. (FIG. 1, far right side of diagram). That is, this recognition event leads to the host's pre-existing immune memory against pathogens and childhood vaccines activating against the tumor in the tumor microenvironment, attacking and destroying the tumors. Destruction of tumor cells can result in components of the preexisting immune response being exposed to cancer cell antigens. Thus, antigens released from the killed tumor cells will initiate an immune response to recruit additional tumor-specific CD8 T cells, or a "second wave" of T cells that then proceed to attack additional tumor cells in the area. This can result in elicitation of an endogenous immune response against the cancer cell antigens (commonly known as "epitope spreading"), and leads to anti-tumor immune memory.

Thus, the methods disclosed herein are methods of treating cancer in an individual by utilizing the individual's own pre-existing adaptive memory immune system to attack cancer cells. The methods described herein make use of the fact that individuals possess preexisting immune responses that were not originally elicited in response to a cancer, but that were elicited instead by routine vaccination scheduling or via microorganisms and pathogens present in the natural environment. Because the cancer cells would not normally express the microbial antigens that elicited the preexisting immune response, it would not be expected that such an immune response would attack a cancer. However, by way of the present methods, such preexisting immune responses can be recruited to attack, kill, and clear a cancer in a subject. This is achieved by introducing into or onto the surface of the cancer one or more antigens known to be recognized by the preexisting immune response in the subject, resulting in cells of the immune response attacking antigen-displaying cancer cells. Further, destruction of cancer cells can result in components of the preexisting immune response being exposed to additional cancer cell antigens. Thus, a general method of the invention can be practiced by recruiting a preexisting microbial or vaccine immune response in an individual to the site of a cancer, such that the preexisting immune response attacks the cancer. Thus, there are generally four steps involved in the method, including: 1) binding VLPs to the tumor cells, cleavage of the epitope from the VLP leading to MHC binding of the epitopes for display on the tumor cell surface, recognition of the loaded MHC by the subject's pre-existing recalled immunity against the epitope, and triggering of a second wave and longer-term anti-tumoral immunity thereafter.

Data obtained from cell culture assays and animal studies may be used in formulating a range of dosages for use in humans. The dosages of such compositions lie preferably within a range of circulating concentrations that include the $ED_{50}$ with little or no toxicity. The dosage may vary within this range depending upon the dosage form employed and the route of administration utilized. For any composition used in the methods of the invention, the therapeutically effective dose may be estimated initially from cell culture assays. A dose may be formulated in animal models to achieve a circulating plasma concentration range that includes the $IC_{50}$ (the concentration of the test composition that achieves a half-maximal inhibition of symptoms) as determined in cell culture. Such information may be used to accurately determine useful doses in humans. Levels in plasma may be measured, for example, by high performance liquid chromatography.

In many instances, it will be desirable to have multiple administrations of the VLP-containing composition, usually at most, at least, or not exceeding 1, 2, 3, 4, 5, 6, 7, 8, 9, 10, 11, 12, 13, 14, 15, or more vaccinations including all ranges there between. The vaccinations will normally be at 1, 2, 3, 4, 5, 6, to 5, 6, 7, 8, 9, 10, 11, to 12 week/month/year intervals, including all values and ranges there between, more usually from three to five week intervals.

In various embodiments, a method is provided for stimulating the cytotoxic activity of macrophages and natural killer cells by administering to a subject in need thereof an effective amount of a conjugated VLP of this invention. The macrophages and natural killer cells may be those present in the tumor microenvironment. In an aspect of this invention, the conjugated VLPs are administered to the subject in an amount effective to stimulate the cytotoxic activity of macrophages and natural killer cells already present in the tumor microenvironment. In various embodiments of this invention, the conjugated VLPs are administered to the subject in an amount effective to attract macrophages and natural killer cells to the tumor microenvironment.

In various embodiments of the invention, the conjugated VLPs are administered to the subject in an amount effective to bind sufficient numbers of antibodies to the recall protein to attract and stimulate macrophages, neutrophils and natural killer cells.

In various embodiments of the invention, a method is provided for redirecting the cytotoxic activity of an existing memory CD8+ T cell to a tumor cell or tumor microenvironment by administering to a subject in need thereof an effective amount of the conjugated VLP of this invention. Preferably, the T cell epitope of the recall protein of the conjugated VLP is from a pathogen for which the subject has been actively vaccinated or from a pathogen that has previously infected the subject and the subject has memory CD8+ T cells that recognize the T cell epitope in complex with an MHC class I molecule on the tumor cells. In an aspect of this invention the effective amount of the conjugated VLP is an amount sufficient to attract the memory CD8+ T cell to the tumor microenvironment. In an aspect of this invention the effective amount of the conjugated VLP is an amount sufficient to stimulate the memory CD8+ T cell present in the tumor microenvironment.

In various embodiments, the tumor is a small lung cell cancer, hepatocellular carcinoma, liver cancer, hepatocellular carcinoma, melanoma, metastatic melanoma, adrenal cancer, anal cancer, aplastic anemia, bile duct cancer, bladder cancer, bone cancer, brain/CNS cancer, breast cancer, cancer of unknown primary origin, Castleman disease, cervical cancer, colon/rectum cancer, endometrial cancer, esophagus cancer, Ewing family of tumors, eye cancer, gallbladder cancer, gastrointestinal carcinoid tumors, gastrointestinal stromal tumor (gist), gestational trophoblastic disease, Hodgkin disease, Kaposi sarcoma, kidney cancer, laryngeal and hypopharyngeal cancer, leukemia, liver cancer, lung cancer, lymphoma, malignant mesothelioma, multiple myeloma, myelodysplastic syndrome, nasal cavity and paranasal sinus cancer, nasopharyngeal cancer. neuroblastoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma, skin cancer, stomach cancer, testicular cancer, thymus cancer, thyroid cancer, uterine sarcoma, vaginal cancer, vulvar cancer, Waldenstrom macroglobulinemia, Wilms tumor, non-Hodgkin lymphoma, Hodgkin lymphoma, Burkitt's lymphoma, lymphoblastic lymphomas, mantle cell lymphoma (MCL), multiple myeloma (MM), small lymphocytic lymphoma (SLL), splenic marginal zone lymphoma, marginal zone lymphoma (extra-nodal or nodal), mixed cell type diffuse aggressive lymphomas of adults, large cell type diffuse aggressive lymphomas of adults, large cell immunoblastic diffuse aggressive lymphomas of adults, small non-cleaved cell diffuse aggressive lymphomas of adults, or follicular lymphoma, head and neck cancer, endometrial or uterine carcinoma, non-small cell lung cancer, osteosarcoma, glioblastoma, or metastatic cancer. In a preferred embodiment, the cancer is a breast cancer, a cervical cancer, an ovarian cancer, a pancreatic cancer or melanoma, The term "cancer" as used herein refers to proliferative diseases, such as lymphomas, lymphocytic leukemias, lung cancer, non-small cell lung (NSCL) cancer, bronchioloalveolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewing's sarcoma, including refractory versions of any of the above cancers, or a combination of one or more of the above cancers.

An aspect of the invention is a method for treating a cancer in a subject in need thereof by administering a conjugated VLP of this invention to the subject wherein the CD8+ epitope of the recall protein is of a failed therapeutic cancer vaccine against a Viral-induced cancer e.g. HPV cervical cancer, HPV+ oral cancer, EBV nasopharyngeal cancer (the "therapeutic vaccine"). The method comprises determining if the subject has been actively vaccinated against the vaccine but did not respond with an anti-tumor effect to the treatment. The patient is then administering to the subject an effective amount of a conjugated VLP of this invention wherein the CD8+ epitope of the recall protein is of the antigenic determinant in the vaccine previously administered to the subject that infected the subject.

In various embodiments, a method is provided for treating a cancer in a subject in need thereof by administering a conjugated VLP of this invention to the subject wherein the CD8+ epitope of the recall protein is of a failed CAR-T cell therapy against a Viral-induced cancer e.g. HPV cervical cancer, HPV+ oral cancer, EBV nasopharyngeal cancer (the "CAR-T"). The method comprises determining if the subject has been actively treated with the CAR-T but did not respond with an anti-tumor effect to the treatment. The patient is then administering to the subject an effective amount of a conjugated VLP of this invention wherein the CD8+ epitope of the recall protein is of the antigenic determinant in the CAR-T previously administered to the subject that infected the subject.

In various embodiments, a method is provided for treating a cancer in a subject in need thereof by administering a conjugated VLP of this invention to the subject wherein the CD8+ epitope of the recall protein is of a failed Vaccine or CAR-T cell therapy against a cancer (the "CAR-T"). The method comprises determining if the subject has been actively treated with the CAR-T but did not respond with an anti-tumor effect to the treatment. The patient is then administered an effective amount of a conjugated VLP of this invention wherein the CD8+ epitope of the recall protein is of the antigenic determinant in the CAR-T previously administered to the subject that infected the subject.

VLPs have adjuvant properties. In some embodiments, the immunogenicity of the conjugated VLP compositions of this invention can be enhanced by the use of additional nonspecific stimulators of the immune response, known as adjuvants. Suitable adjuvants include all acceptable immunostimulatory compounds, such as cytokines, toxins, or synthetic compositions such as alum.

Adjuvants include, but are not limited to, oil-in-water emulsions, water-in-oil emulsions, mineral salts, polynucleotides, and natural substances. Specific adjuvants that may be used include IL-1, IL-2, IL-4, IL-7, IL-12, γ-interferon, GM-CSF, BCG, aluminum salts, such as aluminum hydroxide or other aluminum compound, MDP compounds, such as thur-MDP and nor-MOP, CGP (MTP-PE), lipid A, and monophosphoryl lipid A (MPL), or inactivated microbial agents. RIBI, which contains three components extracted from bacteria, MPL, trehalose dimycolate (TOM), and cell wall skeleton (CWS) in a 2% squalene/Tween 80 emulsion. MHC antigens may even be used.

Various methods of achieving adjuvant affect for the conjugated VLP compositions includes use of agents such as aluminum hydroxide or phosphate (alum), commonly used as about 0.05 to about 0.1% solution in phosphate buffered saline, admixture with synthetic polymers of sugars (CARBOPOL®) used as an about 0.25% solution, aggregation of a protein in the composition by heat treatment with temperatures ranging between about 70° C. to about 101° C. for a 30-second to 2-minute period, respectively Aggregation by reactivating with pepsin-treated (Fab) antibodies to albumin; mixture with bacterial cells, e.g., *C. parvum*, endotoxins or lipopolysaccharide components of Gram-negative bacteria; emulsion in physiologically acceptable oil vehicles, e.g., mannide monooleate (Aracel ATM), or emulsion with a 20% solution of a perfluorocarbon (FLUOSOL-DA®) used as a block substitute may also be employed to produce an adjuvant effect. A typical adjuvant is complete Freund's adjuvant (containing killed *Mycobacterium tuberculosis*), incomplete Freund's adjuvants, and aluminum hydroxide.

For administration to humans, a variety of suitable adjuvants will be evident to a skilled worker. These include, e.g., Alum-MPL as adjuvant, or the comparable formulation, ASO4, which is used in the approved HPV vaccine CERVARIX®, AS03, AS02, MF59, montanide, saponin-based adjuvants such as GPI-0100, CpG-based adjuvants, or imiquimod. In embodiments of the invention, an adjuvant is physically coupled to the VLP, or encapsulated by the VLP, rather than simply mixed with them. In addition to adjuvants, it may be desirable to co-administer biologic response modifiers (BRM) to enhance immune responses. BRMs have been shown to upregulate T cell immunity or down-regulate suppresser cell activity. Such BRMs include, but are not limited to, Cimetidine (CIM; 1200 mg/d) (Smith/Kline, PA, US); or low-dose Cyclophosphamide (CYP; 300 mg/ml) (Johnson/Mead, NJ, US) and cytokines such as γ-interferon, IL-2, or IL-12 or genes encoding proteins involved in immune helper functions, such as B-7. In embodiments of the invention, these genes are encapsulated by the VLP to facilitate their delivery into a subject.

The preparation of compositions that contain polypeptide or peptide sequence(s) as active ingredients is generally well understood in the art. Typically, such compositions are prepared as injectables either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the compositions may contain amounts of auxiliary substances such as wetting or emulsifying agents, pH buffering agents, or adjuvants that enhance the effectiveness of the vaccines. In specific embodiments, vaccines are formulated with a combination of substances.

The compositions comprising the conjugated VLPs of the present invention are in biologically compatible form suitable for administration in vivo to subjects. The pharmaceutical compositions further comprise a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, excipient, or vehicle with which the VLP is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water may be a carrier when the pharmaceutical composition is administered orally. Saline and aqueous dextrose may be carriers when the pharmaceutical composition is administered intravenously. Saline solutions and aqueous dextrose and glycerol solutions may be employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried slim milk, glycerol, propylene, glycol, water, ethanol and the like. The pharmaceutical composition may also contain minor amounts of wetting or emulsifying agents, or pH buffering agents.

The pharmaceutical compositions comprising the conjugated VLPs of the present invention can take the form of solutions, suspensions, emulsions, tablets, pills, capsules, powders, sustained-release formulations and the like. Oral formulation may include standard carriers such as pharmaceutical grades of mannitol, lactose, starch, magnesium stearate, sodium saccharine, cellulose, magnesium carbonate, etc. In a specific embodiment, a pharmaceutical composition comprises an effective amount of a conjugated VLP of the present invention together with a suitable amount of a pharmaceutically acceptable carrier so as to provide the form for proper administration to the patient. The formulation should suit the mode of administration.

The pharmaceutical compositions of the present invention may be administered by any particular route of administration including, but not limited to intravenous, intramuscular, intraarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intraosseous, intrapelvic, intrapericardial, intraperitoneal, intrapleural, intraprostatic, intrapulmonary, intrarectal, intrarenal, intraretinal, intraspinal, intrasynovial, intrathoracic, intrauterine, intravesical, bolus, oral, parenteral, subcutaneous, vaginal, rectal, buccal, sublingual, intranasal, iontophoretic means, or transdermal means. Most suitable routes are intravenous injection or oral administration. In particular embodiments, the compositions are administered at or near the target area, e.g., intratumoral injection.

For parenteral administration in an aqueous solution, for example, the solution should be suitably buffered, if necessary, and the liquid diluent first rendered isotonic with sufficient saline or glucose. These particular aqueous solutions are especially suitable for intravenous, intramuscular, intratumoral, subcutaneous, and intraperitoneal administration. In this connection, sterile aqueous media which can be employed will be known to those of skill in the art in light of the present disclosure. For example, one dosage could be dissolved in isotonic NaCl solution and either added to hypodermoclysis fluid or injected at the proposed site of infusion (see for example, Remington's Pharmaceutical Sciences, 1990). Some variation in dosage will necessarily occur depending on the condition of the subject. The person responsible for administration will, in any event, determine the appropriate dose for the individual subject.

The conjugated VLP-containing compositions of this invention may be administered by inhalation. In certain embodiments a composition can be administered as an aerosol. As used herein the term "aerosol" or "aerosolized composition" refers to a suspension of solid or liquid particles in a gas. The terms may be used generally to refer to a composition that has been vaporized, nebulized, or otherwise converted from a solid or liquid form to an inhalable form including suspended solid or liquid drug particles. Such aerosols can be used to deliver a composition via the respiratory system. As used herein, "respiratory system" refers to the system of organs in the body responsible for the intake of oxygen and the expiration of carbon dioxide. The system generally includes all the air passages from the nose to the pulmonary alveoli. In mammals it is generally considered to include the lungs, bronchi, bronchioles, trachea, nasal passages, and diaphragm. For purposes of the present disclosure, delivery of a composition to the respiratory system indicates that a drug is delivered to one or more of the air passages of the respiratory system, in particular to the lungs.

Additional formulations which are suitable for other modes of administration include suppositories (for anal or vaginal application) and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations, or powders and contain about 10% to about 95% of active ingredient, preferably about 25% to about 70%.

The conjugated VLP compositions may be formulated into a vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The pharmaceutical compositions of the present invention can also include an effective amount of an additional adjuvant. As noted herein, papillomavirus VLPs have adjuvant properties. Suitable additional adjuvants include, but are not limited to, Freund's complete or incomplete, mineral gels such as aluminum hydroxide, surface active substances such as lysolecithin, pluronic polyols, polyanions, peptides, oil emulsions, dinitrophenol, and potentially useful human adjuvants such as Bacille Calmette-Guerin (BCG), *Corynebacterium parvum*, and non-toxic cholera toxin.

Under ordinary conditions of storage and use, these preparations contain a preservative to prevent the growth of microorganisms. In all cases the pharmaceutical form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the conjugated VLPs in the required amount in the appropriate solvent with various ingredients enumerated above, as required may be followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Different aspects of the present invention involve administering an effective amount of a composition comprising the conjugated VLPs to a subject in need thereof. In some embodiments of the present invention, a conjugated VLP comprising a target peptide comprising a CD8+ T cell epitope is administered to the patient to treat a tumor or prevent the recurrence of such tumor. Such compositions will generally be dissolved or dispersed in a pharmaceutically acceptable carrier or aqueous medium.

Methods of Providing an Appropriate VLP

In various embodiments, a method for providing a conjugated VLP to a patient in need thereof is provided comprising: (1) measuring the preexisting immunity in a patient, and (2) selecting the appropriate conjugated VLP for administration of a patient in need. The appropriate conjugated VLP to administer to the patient will depend upon the patients T cell profile. The appropriate conjugated VLP will be one that is capable of eliciting a T cell response that is at least twice the baseline total of CD8+ cells. In various embodiments, the appropriate conjugated VLP will be one that is capable of eliciting a T cell response that is twice the baseline total of CD8+ or total CD8+ CD69+ T cells. The goal is to choose the appropriate conjugated VLP based on the patient's vaccination history or prior exposure to a pathogen. Determining which conjugated VLP is appropriate can be achieved through: (1) patient interviews; (2) review of a patient's medical records; and/or (3) assessing the patient's T cell profile.

In various embodiments, more than one recall protein might be suitable for eliciting an immune response directed at a tumor. In various embodiments, a conjugated VLP carrying either recall protein will be appropriate. In various embodiments, more than one recall protein is expressed and bound to the VLP. In various embodiments, a single fusion protein will comprise more than one recall protein. In various embodiments, multiple fusion proteins comprising different recall proteins will be conjugated to the VLP. In various embodiments, the invention comprises a population of conjugated VLPs as described herein and a pharmaceutically acceptable excipient. In various embodiments, the conjugated VLPs administered to the subject are identical. In various embodiments, conjugated VLPs carrying different recall protein(s) are administered to a subject.

Selection Based on Prior Vaccination.

In various embodiments of the invention, a method of selecting an appropriate conjugated VLP is provided in order to administer to a subject in need thereof. In various embodiments this involves ascertaining if the subject has been actively vaccinated against a given pathogen, e.g., a parasite, a bacterium, or virus, e.g., measles or polio, and then selecting and administering to the subject a conjugated VLP as disclosed herein wherein the CD8+ T cell epitope of the recall protein is from the pathogen against which the subject has been immunized. In various embodiments, a subject's vaccination history is obtained by reviewing the subject's medical record. In various embodiments, a subject's vaccination history is obtained by interviewing the subject.

Selection Based on Prior Infection.

In various embodiments, the method of selecting an appropriate conjugated VLP for administration to a subject in need thereof involves ascertaining if a subject has been previously infected with a given pathogen, e.g., a parasite, a bacterium, or virus, e.g., measles or polio, and resolved the infection. In various embodiments, the subject is then administered a conjugated VLP comprising a recall protein which comprises said pathogen for which the subject has been previously infected.

One may ascertain if a subject has been infected with a particular pathogen by reviewing the subjects' medical records or interviewing the subject. Non-limiting examples of CD8+ T cell epitopes that bind to particular MHC class I molecules are set forth in Table 1. The method may also comprise determining which MHC class I determinant(s) the subject's cells express and then administering a conjugated VLP of this invention wherein the CD8+ T cell epitope of the recall protein is a CD8+ T cell epitope of the antigenic component of the pathogen in the vaccine or of the pathogen that previously infected the subject that forms a complex with the subject's MHC class I determinant(s).

Measuring T Cell Responses.

In various embodiments, a patient's T cell profile is assessed in order to select an appropriate conjugated VLP using various techniques known in the art. This profile is then used to select the appropriate conjugated VLP to administer. Such techniques including measuring interferon-γ levels, using flow cytometry to isolate Ag-specific CD8+ T cells, and/or cytotoxicity assays. To measure interferon-γ (a marker of T cell activation), intracellular staining of isolated T cells. Alternatively, an enzyme-linked immunosorbent spot (ELISPOT) assay for interferon-γ may be conducted. This technique allows for a high throughput assessment of a patient's T cell profile. This method can potentially detect one in 100,000-300,000 cells. Briefly, a monoclonal antibody for a specific cytokine is pre-coated onto a polyvinylidene difluoride (PVDF)-backed microplate. CD8+ T cells are pipetted into the wells along with dendritic cells and individual peptides and the microplate is placed into a humidified 37° C. $CO_2$ incubator for a period ranging from 24 to 48 h. During incubation, the immobilized antibody binds the cytokine secreted from the cells. After washing a detection antibody specific for the chosen analyte is added to the wells. Following the washes, enzyme conjugated to streptavidin is added and a substrate is added. A colored precipitate forms, according to the substrate utilized and appears as spot at the sites of cytokine secretion, with each individual spot representing a single producing cell.

In various embodiments, the invention described here in provides a method of determining the appropriate conjugated VLP to administer to a patient in need thereof, by assessing the patients T cell profile, comprising: (1) collecting PBMCs from patients/participants (pre-vaccination sample), (2) preparing the ELISPOT plates by coating with anti-IFN-γ antibody (incubate overnight), (3) Incubating PBMCs with one of the pool of peptides of interest, ones expected to elicit a T cell response (incubate for 1-2 days), (4) washing the plates, adding a biotinylated secondary antibody (incubating for a few hours), (5) washing the plates, adding avidin conjugated horseradish peroxidase and incubating, (6) washing plates, adding aminoethyl carbazole (AEC) for a few minutes, (7) stopping the reaction (water), and (8) visualizing on an ELISPOT reader. The disclosed method can detect up to one in 100,000-300,000 cells. A two-fold increase in the frequency of antigen-specific T cells should be considered as a signal.

In various embodiments T cell proliferation can be measured by 3H (tritiated)-thymidine. Such methods are sensitive and can be used for high throughput assays. Such techniques may also include carboxyfluorescein succinimidyl ester (CFSE) and Ki64 intracellular staining.

Selecting Recall Proteins Based on Tropism.

It is known in the art that some viruses display a tropism for particular type of tissue. For example: viruses that display a tropism for brain tissue include without limitation, JC virus, measles, LCM virus, arbovirus and rabies; viruses that display a tropism for eye tissue include without limitation herpes simplex virus, adenovirus, and cytomegalovirus; viruses that display a tropism for nasal tissue include without limitation, rhinoviruses, parainfluenza viruses, and respiratory syncytial virus; viruses that display a tropism for oral tissue, e.g., oral mucosa, gingiva, salivary glands, pharynx, include without limitation, herpes simplex virus type I and type II, mumps virus, Epstein Barr virus, and cytomegalovirus; viruses that display a tropism for lung tissue include without limitation, influenza virus type A and type B, parainfluenza virus, respiratory syncytial virus, adenovirus, and SARS coronavirus; viruses that display a tropism for nerve tissue, e.g., the spinal cord, include without limitation poliovirus and HTLV-1; viruses that display a tropism for heart tissue, include without limitation, Coxsackie B virus; viruses that display a tropism for liver tissue, include without limitation, hepatitis viruses types A, B, and C; viruses that display a tropism for gastrointestinal tissue, e.g., stomach, and large and small intestine, include without limitation, adenovirus, rotavirus, norovirus, astrovirus, and coronavirus; viruses that display a tropism for pancreatic tissue, include without limitation, coxsackie B virus; viruses that display a tropism for skin tissue, include without limitation, varicella zoster virus, herpes simplex virus 6, smallpox virus, molluscum contagiosum, papilloma viruses, parvovirus B19, rubella, measles and coxsackie A virus; and viruses that display a tropism for genital tissue, include without limitation, herpes simplex type 2, papillomaviruses, human immunodeficiency virus (HIV).

In various embodiments, a method for treating a cancer in a subject in need thereof is provided by administering a conjugated VLP of this invention to the subject wherein the recall protein is a CD8+ epitope of a pathogen that has a tropism for the tissue that is the source of the cancer (the "source tissue"). In various embodiments, the appropriate conjugated VLP is selected by first determining the source tissue of the tumor cell and then selecting a recall protein:

(1) to which the patient already has existing CD8+ T cells, and (2) that has a tropism for the source tissue of the tumor. The selected conjugated VLP(s) are then administered to the patient in need thereof.

In various embodiments, a method for treating a lung cancer comprising determining if a subject has been actively vaccinated against a pathogen that infects lung cells, e.g., an influenza virus, e.g., influenza virus type A or type B, then administering an effective amount of a conjugated VLP of this invention wherein the CD8+ T cell epitope of the recall protein is of the antigenic determinants of the pathogen contained in the vaccine and which T cell epitope forms a complex with an MHC molecule class I of the subject. In an aspect of a method of this invention for treating a lung cancer includes determining if a subject has been infected with pathogen that infects lung cells, e.g., an influenza virus, e.g., influenza virus type A or type B, then administering an effective amount of a conjugated VLP of this invention wherein the CD8+ T cell epitope of the recall protein is of that pathogen and which T cell epitope forms a complex with an MHC class I molecule of the subject.

An aspect of the invention is a method for treating an oral cancer, which are part of the group of cancers commonly referred to as head and neck cancers, by administering a conjugated VLP of this invention wherein the CD8+ epitope of the recall protein is of a pathogen that has a tropism for oral tissue, e.g., a mumps virus, Epstein Barr virus, cytomegalovirus, or a herpes simplex virus type 1. The method comprises determining if a subject in need thereof has been actively vaccinated against, or infected with, e.g., a mumps virus, Epstein Barr virus, cytomegalovirus, or a herpes simplex virus type 1, and if the subject has been vaccinated or infected previously then administering to the subject a conjugated VLP of this invention wherein the CD8+ epitope of the recall protein is of a mumps virus or a measles virus or of the antigenic component of the vaccine the subject had received, or of the pathogen, i.e., mumps, measles, Epstein Barr virus, cytomegalovirus, or a herpes simplex virus type 1, that had previously infected the subject.

Combination Therapy

In various embodiments, the conjugated VLP may be co-administered with other cancer therapeutics. Furthermore, in some embodiments, the conjugated VLPs described herein are administered in conjunction with other cancer treatment therapies, e.g., radiotherapy, chemotherapy, surgery, and/or immunotherapy. In some aspects of this invention, the conjugated VLPs described herein are administered in conjunction with checkpoint inhibitors. In various embodiments the chimer VLP may be administered in conjunction with an immune agonist. In various embodiments, the conjugated VLP may be administered in conjunction with treatment with a therapeutic vaccine. In various embodiments, the conjugated VLP may be administered in conjunction with treatment with a conjugated antigen receptor expressing T cell (CAR-T cell). In various embodiments, the conjugated VLP may be administered in conjunction with treatment with another immuno-oncology product. The conjugated VLPs of the present invention and other therapies or therapeutic agents can be administered simultaneously or sequentially by the same or different routes of administration. The determination of the identity and amount of therapeutic agent(s) for use in the methods of the present invention can be readily made by ordinarily skilled medical practitioners using standard techniques known in the art.

EXAMPLES

Example 1

Conjugated VLPs Bind to Mouse Tumors In Vivo

The ability of the described conjugated VLPs to bind to tumors is an important first step for the proposed mechanism of action (see FIG. 1). Binding of VLP in vivo was assessed using a murine cervical cancer model, TC-1. Briefly, unconjugated VLPs are produced in Expi293F™ human cells (ThermoFisher Scientific, Waltham, Mass., US) using the Expi293F™ Expression system. In this protocol, $360 \times 10^6$ cells in 120 mL of cultured media is prepared in a 250 mL shake flask. Following this, to express the HPV16 L1 VLP, cells were transfected with the HPV16 L1 gene expression vector (Cat #89910, Addgene, Cambridge, Mass., US) via the manufacturer's protocols (ThermoFisher Scientific, Waltham, Mass., US). Transfected cells were maintained for 72 hrs and were then harvested. HPV particles were released from Expi293F cells by detergent lysis and the lysate was incubated overnight at 37° C. with a mild detergent, e.g. Brij58 or Triton X-100. The VLP from the overnight incubated lysates were then solubilized by addition of sodium chloride. The lysate was then clarified by low-speed centrifugation. Capsids were separated from cell debris and detergent by high salt extraction followed by ultracentrifugation through an OPTIPREP™ (iodixanol) step gradient according to manufacturer's instructions (Sigma-Aldrich, St Louis, Mich., US). Purity of the VLP preparation was determined by SDS-PAGE Coomassie stained gel (4-20% CRITERION™ gel) staining as per manufacturer's protocol (Biorad Laboratories, Hercules, Calif., US) and morphology of particles assessed by electron microscopy (EM). (See also, WO 2018/237115).

The HPV16 L1 wild type protein sequence as reported elsewhere is as follows (SEQ ID NO: 86):

```
Met Ser Leu Trp Leu Pro Ser Glu Ala Thr Val Tyr Leu Pro Pro Val

Pro Val Ser Lys Val Val Ser Thr Asp Glu Tyr Val Ala Arg Thr Asn

Ile Tyr Tyr His Ala Gly Thr Ser Arg Leu Leu Ala Val Gly His Pro

Tyr Phe Pro Ile Lys Lys Pro Asn Asn Asn Lys Ile Leu Val Pro Lys

Val Ser Gly Leu Gln Tyr Arg Val Phe Arg Ile His Leu Pro Asp Pro

Asn Lys Phe Gly Phe Pro Asp Thr Ser Phe Tyr Asn Pro Asp Thr Gln

Arg Leu Val Trp Ala Cys Val Gly Val Glu Val Gly Arg Gly Gln Pro

Leu Gly Val Gly Ile Ser Gly His Pro Leu Leu Asn Lys Leu Asp Asp

Thr Glu Asn Ala Ser Ala Tyr Ala Ala Asn Ala Gly Val Asp Asn Arg
```

-continued

```
Glu Cys Ile Ser Met Asp Tyr Lys Gln Thr Gln Leu Cys Leu Ile Gly
Cys Lys Pro Pro Ile Gly Glu His Trp Gly Lys Gly Ser Pro Cys Thr
Asn Val Ala Val Asn Pro Gly Asp Cys Pro Pro Leu Glu Leu Ile Asn
Thr Val Ile Gln Asp Gly Asp Met Val Asp Thr Gly Phe Gly Ala Met
Asp Phe Thr Thr Leu Gln Ala Asn Lys Ser Glu Val Pro Leu Asp Ile
Cys Thr Ser Ile Cys Lys Tyr Pro Asp Tyr Ile Lys Met Val Ser Glu
Pro Tyr Gly Asp Ser Leu Phe Phe Tyr Leu Arg Arg Glu Gln Met Phe
Val Arg His Leu Phe Asn Arg Ala Gly Thr Val Gly Glu Asn Val Pro
Asp Asp Leu Tyr Ile Lys Gly Ser Gly Ser Thr Ala Asn Leu Ala Ser
Ser Asn Tyr Phe Pro Thr Pro Ser Gly Ser Met Val Thr Ser Asp Ala
Gln Ile Phe Asn Lys Pro Tyr Trp Leu Gln Arg Ala Gln Gly His Asn
Asn Gly Ile Cys Trp Gly Asn Gln Leu Phe Val Thr Val Val Asp Thr
Thr Arg Ser Thr Asn Met Ser Leu Cys Ala Ala Ile Ser Thr Ser Glu
Thr Thr Tyr Lys Asn Thr Asn Phe Lys Glu Tyr Leu Arg His Gly Glu
Glu Tyr Asp Leu Gln Phe Ile Phe Gln Leu Cys Lys Ile Thr Leu Thr
Ala Asp Val Met Thr Tyr Ile His Ser Met Asn Ser Thr Ile Leu Glu
Asp Trp Asn Phe Gly Leu Gln Pro Pro Pro Gly Gly Thr Leu Glu Asp
Thr Tyr Arg Phe Val Thr Ser Gln Ala Ile Ala Cys Gln Lys His Thr
Pro Pro Ala Pro Lys Glu Asp Pro Leu Lys Lys Tyr Thr Phe Trp Glu
Val Asn Leu Lys Glu Lys Phe Ser Ala Asp Leu Asp Gln Phe Pro Leu
Gly Arg Lys Phe Leu Leu Gln Ala Gly Leu Lys Ala Lys Pro Lys Phe
Thr Leu Gly Lys Arg Lys Ala Thr Pro Thr Thr Ser Ser Thr Ser Thr
Thr Ala Lys Arg Lys Lys Arg Lys Leu
```

Figure 2A:
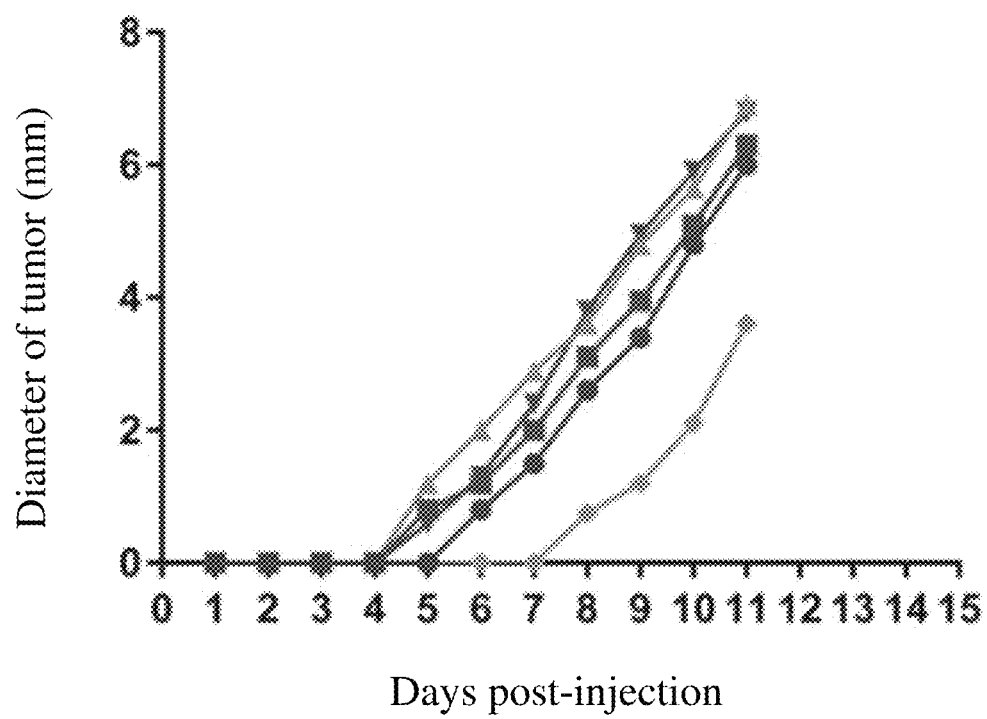
FIG. 2A shows mouse TC-1 tumor growth over time for C57BL/6 mice where the TC-1 tumors express both green fluorescent protein (GFP) and luciferase.
Figure 2B:
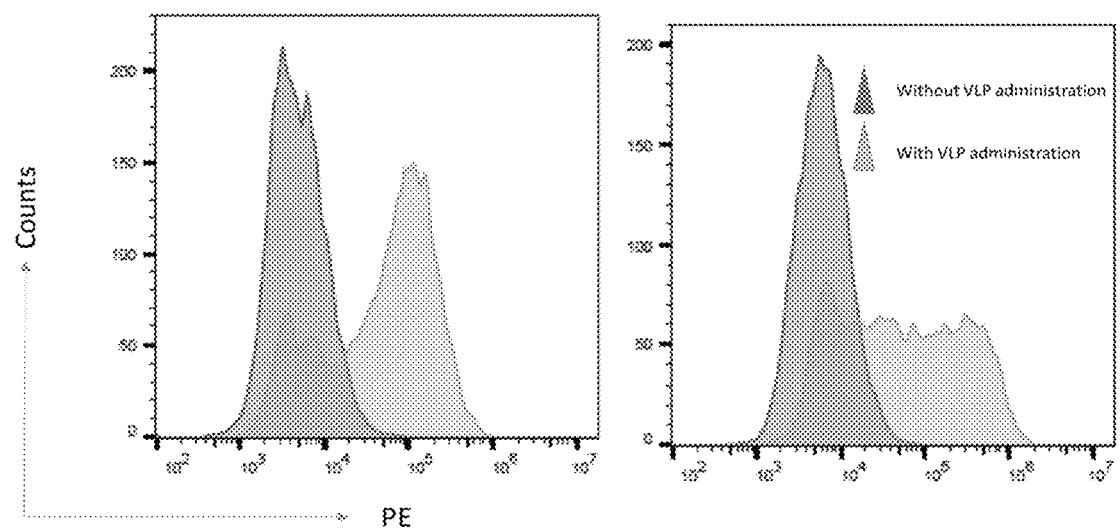
FIG. 2B shows a graphical representation of fluorescence activated flow cell sorting cytometry (FACS) data generated from analysis of the TC-1 tumors excited from the C57BL/6 mice either treated with VLP (lighter shaded peak) or not treated with VLP (darker shaded peak). Left panel is gated for GFP the right panel is gated to VLP detected by way of an phycoerythrin (PE)-conjugated anti-mouse antibody specific for VLP.

For functional assays, live C57BL/6 mice (n=5, The Jackson Laboratory, Bar Harbor, Mass., US) were subcutaneously injected with luciferase/green fluorescent protein (GFP)-expressing TC-1 tumor cells ($2\times10^5$ cells). Mice were monitored for approximately 2 weeks to ensure consistency in tumor growth and also until palpable tumors were observed (about 7 mm in diameter). (See, FIG. 2A). Three mice were injected intravenously with 50 µg of VLP. Two mice served as untreated controls. After 16-24 hours post injection of the VLP, all 5 mice were sacrificed and the tumors were excised. Tumors were then digested with collagenase before being treated at a dilution of 1:100 at 4° C. in fluorescence activated cell sorting (FACs) staining buffer (phosphate buffered saline (PBS) with 1% bovine serum albumin (BSA)), first with HPV16 anti-V5 anti-mouse antibody specific for VLP (Abcam, Burlingham, Calif., US). After one hour, cells were then washed twice with FACs staining buffer and stained for another hour at a dilution of 1:100 at 4° C. with goat phycoerythrin (PE)-conjugated anti-mouse antibody specific for VLP (R&D systems, Minneapolis, Minn., US). Cells were then washed twice again with FACs staining buffer before being analyzed by fluorescence activated cell sorting (FACS) cytometry: (1) first, gated for GFP to sort for only tumor cells; and (2) second, to assess the sorted tumor cells for the presence of the VLP (anti-L1 VLP antibody). (See FIG. 2B, right panel and left panel are data each generated from a different mice). FIG. 2B demonstrates that the conjugated VLPs were able to bind to the tumor, as indicated by rightward shift on the histogram plot of both the left and right panels.

Example 2

Conjugated VLP Bind to Human Tumors In Vitro

To test for the ability of conjugated VLPs to bind to human tumors in vitro, five human tumor cells lines are to be assessed: OVCAR3, MDA-MB231, HCT116, PC-3, and SKOV3 (ATCC, Manassas, Va., US). The respective cell lines will be first seeded in one well within a 6 well plate. After 16 to 24 hours, cells will be dissociated using 0.05% trypsin. Cells will then be counted to achieve $1\times10^6$ cells, centrifuged, and the supernatant removed before being re-suspended in 100 µL of FACS buffer (1% FBS in PBS). Next, 0.3 µg/ml of conjugated VLP will be added to the respective cultures in vitro and the cultures incubated for 24 hours under optimal growth conditions. To show that the binding is HSPG-specific, conjugated VLPs will be either pre-incubated with or without heparin (final concentration of 0.1 mg/ml) and incubated at 4° C. (to prevent endocytosis) for 1 hr. After 1 hr of binding, cells will be washed twice with 1 mL of FACS buffer before being resuspended in 100 µL of FACS buffer again. The samples will then be incubated with PE-conjugated anti-mouse antibody specific for VLP at 4° C. for 1 hour. After 1 hour, cells will be washed and re-suspended in FACS buffer for analysis by flow cytometry. Binding is then assessed either as a percent positive of total PE+ cells, or of the geometric mean fluorescence, as indicated by a rightward shift on the histogram plot, as in Example 1 and FIGS. 2A and 2B.

Example 3

Conjugated VLP Bind to Human Tumors In Vivo

The described conjugated VLPs will be further tested to assess their ability to bind in vivo to human tumors. In a first experiment, mice will be injected with OVCAR3 tumor cells ($3 \times 10^6$ cells), a human ovarian cancer cell line. At approximately two weeks after injection, the average tumor volume is expected to be approximately 10 mm$^3$ in volume. Three weeks post injection, the tumor bearing mice will be administered a $Cu^{2+}$ or $Zn^{2+}$ radiolabeled VLPs. Biodistribution and tumor specificity of the VLP is to be assessed at 4, 12, 24, and 48 hours. The tumors are then removed for weighing, radioactive counting, viral micro distribution and cellular colocalization. In addition to tumors, various major organs such as the liver, spleen, kidneys will be assessed for VLPs presence using imaging methods as well as histology to assess the efficacy of VLP homing to the tumor. In further experiments, mice are to be injected with other tumor cell lines such as HCT116, PC-3, or SKOV3 and the same experimental protocol followed.

Example 4

VLP-Induced T Cell-Mediated Killing of Tumor Cells In Vitro in a Time-Dependent Manner The ability of conjugated VLPs to deliver epitopes to MHC proteins on a tumor cell surface and subsequently redirect existing T cells to subject tumor cells leading to cytotoxic killing of tumor cells was tested in vitro. We chose to demonstrate proof-of-concept efficacy using pre-existing murine memory responses to the human papillomavirus HPV16 E7 antigen in a murine tumor model as this would be more clinically relevant. HPV16 E7 is a true human viral antigen, as opposed to often used artificial antigens such as ovalbumin (OVA). It is known that several different E7 antigen-specific CD8$^+$ T-cells are found in the peripheral blood of healthy human donors with different HLA-I (MHC-I) genes. Therefore, the use of E7 is relevant, provides proof-of-concept showing the redirection of pre-existing CD8$^+$ T-cell responses to target a non-virally associated malignancy (tumor), and acts as a solid base from which to extend this system to other human viral antigens.

Conjugation of VLPs.

To produce conjugated VLPs, recall proteins were synthesized to greater than 85% purity as polycationic 18-mer to 20-mer peptides comprising a maleimide molecule at the N-terminus, followed by a protease cleavage site and ending with a CD8+ recall epitope, i.e. N-terminal maleimide-RRRRRVKR-epitope (Genscript, New Jersey, US). Samples were sent as lyophilized materials and diluted to a concentration of 1 to 20 mM with dimethyl sulfoxide (DMSO). Conjugated VLP was prepared for conjugation via the following protocol. First, VLPs at a concentration of at least 1 mg/mL were dialyzed into conjugation reaction buffer (50 mM sodium phosphate, pH 6.5, 500 mM NaCl, 2 mM EDTA, 0.05% Tween 80) with buffer exchanged 3 times (3+1 h, 3+1 h, and overnight 16+3 h at 2 to 8° C.). The next day, VLPs were then treated with TCEP for 1 hour without shaking at room temperature at a TCEP:L1 (monomer) ratio of 10:1 molar ratio, where the concentration of L1 monomer was 0.77 mg/mL. Subsequently, conjugation was performed by adding the 18- to 20-mer peptide at a molar ratio of peptide:L1 monomer of 5:1, bringing the final concentration of L1 monomer to 0.58 mg/mL. The reaction was shaken at 200 rpm for 1 hour. Following conjugation, contents from the reaction were subjected to dialysis (PBS, pH 7.0+0.1, 500 mM NaCl, 0.05% Tween 80) using a dialysis cassette (MWCO=1000 kDa) for about 3+1 hours in a cold room (2 to 8° C.). Next, the contents were subjected to density gradient ultracentrifugation (UC) OPTIPREP™ gradient (in DPBS, 0.8M NaCl) at 40,000 rpm, for 16 hours at 16° C. Fractions (1-3) starting from the interface between 33-39% OPTIPREP™ were collected and then subjected to a final dialysis (MWCO=1000 kDa) for 3+1, 3+1, and 16+3 hours in a cold room. Following purification, samples were analyzed under gel electrophoresis/Coomassie staining to determine % conjugation via the shift in L1 band beyond about 55 kDa.

Quantification of Conjugated VLPs.

Product concentrations, as well as % fusion protein conjugation, was determined by reducing SDS-PAGE (4-20% CRITERION™ TGX Stain-Free™ Precast Gels, 18 Well Comb, 30 μL, 1.0 mm, Bio-Rad, Hercules, Calif., US). In addition, an unconjugated VLP control as well as five known BSA standards (Sigma Life Science, St. Louis, Mo., US) of quantities between 5 μg to 2.5 μg will always be included as controls. Gels were run per manufacturer's protocols and then subsequently subjected to Coomassie gel stain as per manufacturer's protocols (Coomassie Brilliant Blue R-250 dye, Bio-Rad, Hercules, Calif., US). Amount and/or percent conjugation was determined via densitometry analysis utilizing BioRad software imaging analysis as per the manufacturer's protocols.

Design of Peptides.

Peptides are designed to include an N-terminal maleimide-RRRRRVKR-epitope, as described above. The peptides therefore contain a maleimide molecule at the N-terminus of the recall protein followed by a furin cleavage sequence: R X R/K R (SEQ ID NO: 89) upstream of the recall protein sequence. Exemplary furin cleavage sequence: ARG VAL LYS ARG (SEQ ID NO: 90).

For functional assays, murine B16 (melanoma/skin), and ID8 (ovarian) tumor cells overexpressing luciferase gene (B16-luc and ID8-luc) were grown in culture. Under normal circumstances, these two murine tumor cell lines B16 and ID8 will not be killed by murine HPV16 E7-specific CD8+ T cells since these cell lines do not express the HPV16 E7 antigen. Cells were grown in culture and seeded overnight. The next day, cells were then treated with either: (1) 3 different concentrations of HPV16 E7 peptide, RAHYNIVTF (SEQ ID NO: 1) (1 μg/ml, 100 pg/ml, 1 pg/mL), (2) HPV16 E7-conjugated VLP (2.5 μg/mL), (3) an unconjugated (control) VLP (2.5 μg/mL), or (4) were left untreated. The cells were then washed and co-cultured with murine CD8+ HPV16 E7-specific T cells at varying E:T ratios (Effector:Target ratio). The total final volume after co-culture was 200 μL. The cell viability was measured after a certain time of co-culturing by measuring the expression of luciferase, which is used as a surrogate marker for cell viability since these cells over-express luciferase. Reduced luciferase activity indicated more cell death suggesting greater immune redirection and hence greater cytotoxicity.

Figures 3A, 3B:
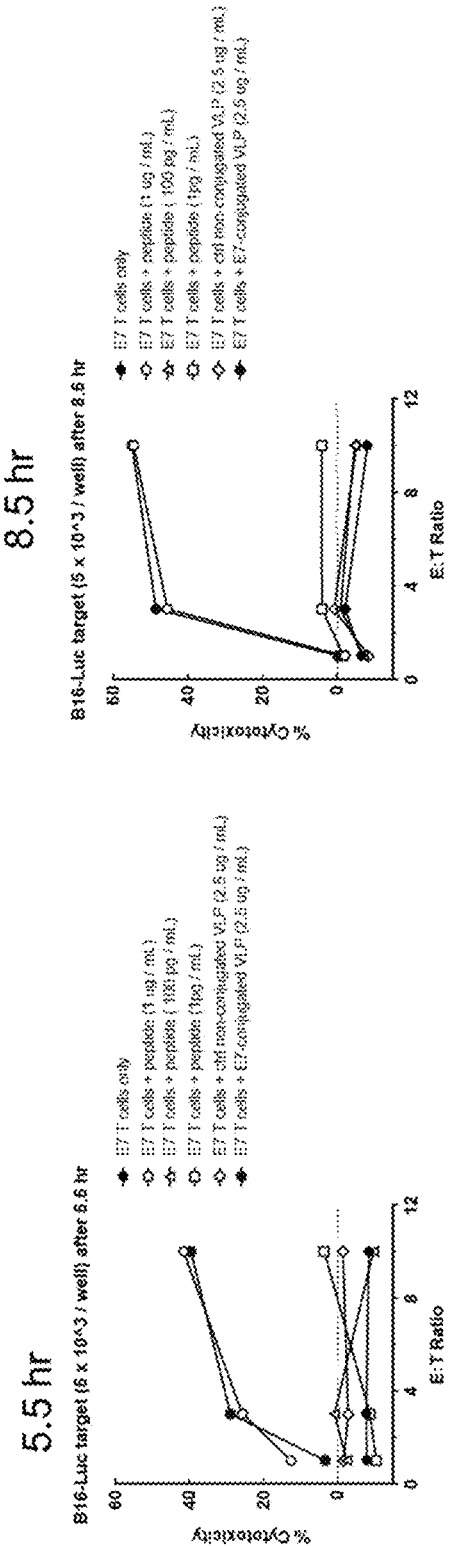
FIG. 3A and FIG. 3B show B16-LUC cells incubated with varying concentrations of E7 peptide alone or E7 peptide conjugated to VLP at 5.5 hrs and 8.5 hrs, respectively. Likewise.
Figures 3C, 3D:
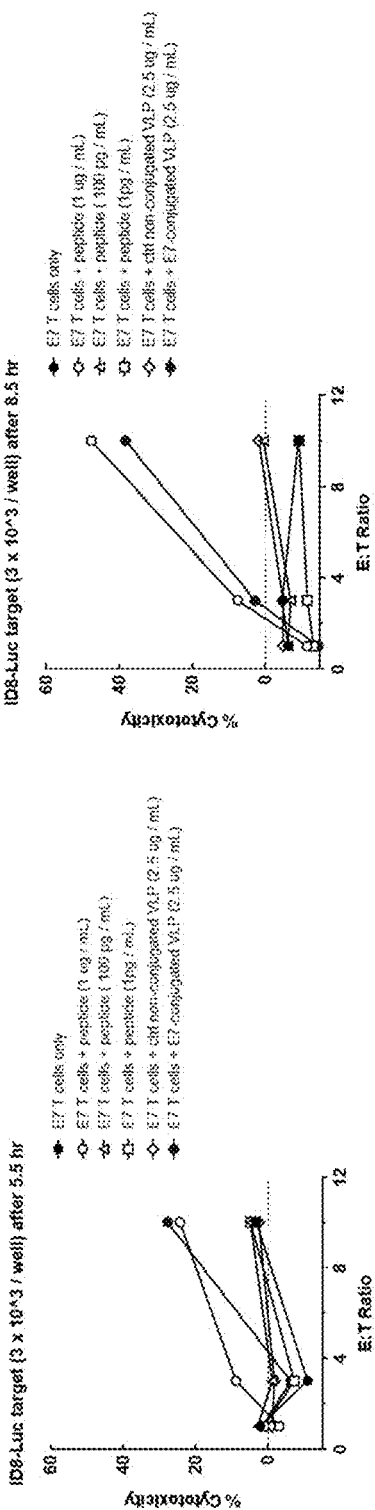
FIG. 3C and FIG. 3D show ID8 cells incubated with E7 peptide alone or E7 peptide conjugated to VLP at 5.5 hrs and 8.5 hrs, respectively.
Figures 4A, 4B:
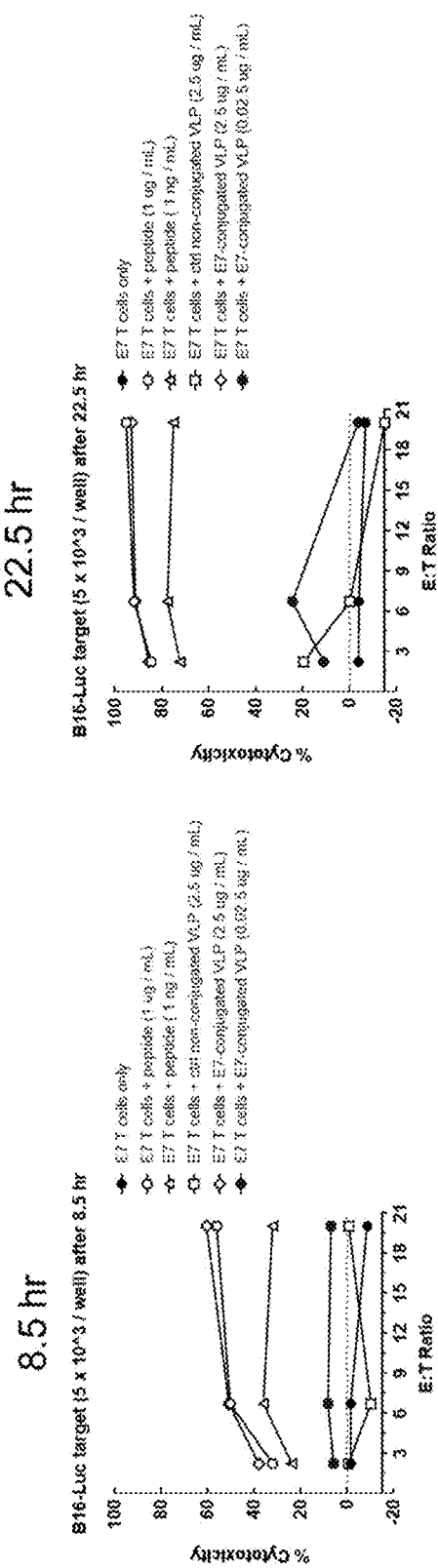
FIGS. 4A and 4B show that cytotoxicity is improved between 8.5 hrs and 22.5 hrs, respectively, for E7-conjugated VLP incubated with B16-LUC cells and murine CD8+ HPV16 E7-specific T cells. Similarly.
Figures 4C, 4D:
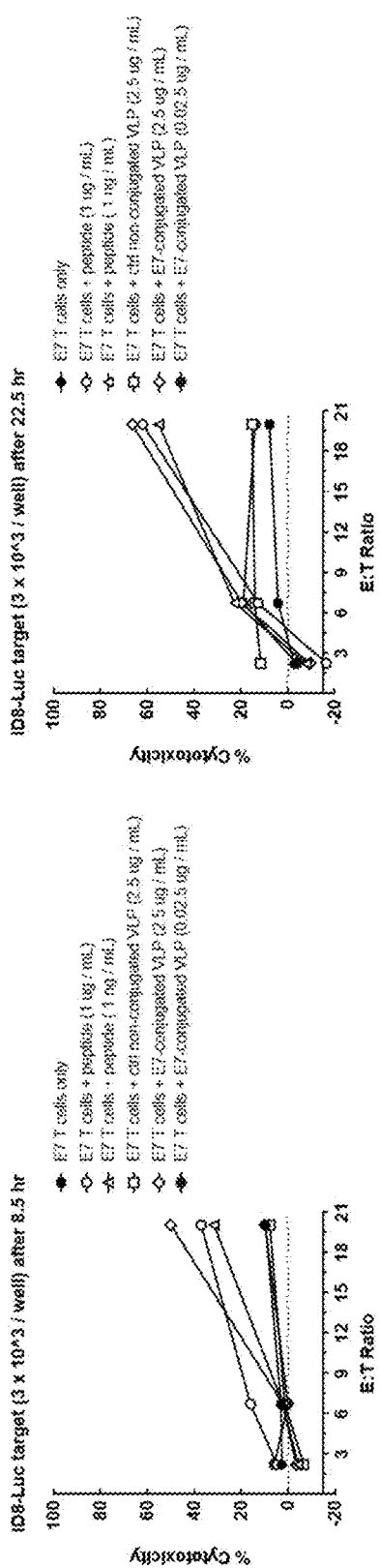
FIGS. 4C and 4D show that cytotoxicity is improved between 8.5 hrs and 22.5 hrs, respectively, for E7-conjugated VLP incubated with ID8 cells and murine CD8+ HPV16 E7-specific T cells.

Responses to the HPV16 E7-conjugated VLP and HPV16 E7 peptide were time-dependent and concentration-dependent in both cancer cell lines. After 5.5 hrs of co-culturing, both the E7 peptide only (1 μg/mL) and the conjugated VLP (2.5 μg/mL) demonstrated significant levels of T cell mediated cytotoxicity in the B16-luc. (See, FIG. 3A, B16-LUC, and FIG. 3C, ID8). Additional cytotoxicity was seen if co-culturing occurred for 8.5 hours, with cytotoxicity levels of approximately 50% in B16-LUC cells (FIG. 4B) and 38-58% in ID8-LUC cells (FIG. 4D) at E:T ratios of 10. Likewise, FIG. 4 shows similar results achieved over an even longer period of time, 22.5 hrs. Specifically, FIGS. 4A and 4B show that cytotoxicity is improved between 8.5 hrs and 22.5 hrs, respectively, for E7-conjugated VLP incubated with B16-LUC cells and murine CD8+ HPV16 E7-specific T cells. Similarly, FIGS. 4C and 4D show that cytotoxicity is improved between 8.5 hrs and 22.5 hrs, respectively, for E7-conjugated VLP incubated with ID8 cells and murine CD8+ HPV16 E7-specific T cells.

These results suggest that both an E7 peptide at higher concentrations (1 µg/mL) and an E7-conjugated conjugated VLP exhibit time dependent tumor cell killing. This further suggests that the E7-conjugated conjugated VLPs undergo furin cleavage and epitope coating of MHC receptors on the tumor cells in order to achieve tumor cell killing.

Example 5

VLP-Induced E7 T Cell-Mediated Killing of Tumor Cells in a Concentration-Dependent Manner E7 T cell-mediated killing was also shown to be E7-conjugated VLP concentration dependent. Murine B16 (Melanoma/Skin) and ID8 (ovarian) tumor cells overexpressing luciferase gene (B16-luc and ID8-luc) were seeded. 24 hours later, the cells were then treated with: (1) an HPV16 E7 peptide RAHYNIVTF (SEQ ID NO: 1) (1 µg/ml, 1 ng/ml); (2) HPV16 E7 conjugated VLP (2.5 µg/ml, 0.025 µg/ml); (3) an unconjugated (control, 2.5 µg/ml) VLP; or (4) were left untreated. The cells were then washed and co-cultured with CD8+ HPV16 E7 specific T cells at varying E:T ratios (Effector:Target ratio). The total final volume after co-culture was 200 µL. The cell viability was measured after a certain time of co-culturing by measuring the expression of luciferase, which is used as a surrogate marker for cell viability since these cells over-express luciferase. Reduced luciferase activity indicated greater immune redirection and hence greater cytotoxicity.

Responses to the HPV16 E7-conjugated VLP and HPV16 E7 peptide were concentration-dependent and in both cancer cell lines. Both the E7 peptide alone (1 µg/mL) and the E7 conjugated to VLP (2.5 µg/mL) demonstrated significant levels of T cell mediated cytotoxicity in both cell lines. (See, FIGS. 3A and 3B, B16-LUC, and FIGS. 3C and 3D, ID8). FIG. 3 shows particularly that E7 peptide alone at 1 pg/mL exhibit little if any tumor cell killing, regardless of time point, whereas E7 peptide at 100 pg/mL and 1 µg/mL exhibited significant tumor cell cytotoxicity, regardless of time point. Similarly, concentration dependence of cytotoxicity was observed for E7-conjugated VLP in FIG. 4. (See, FIGS. 4A and 4B, B16-LUC, and FIGS. 4C and 4D, ID8). In FIG. 4, significant increases in cytotoxicity are observed between 0.025 µg/mL conjugated VLP vs. 2.5 µg/mL conjugated VLP for both cell lines regardless of time point (8.5 hr or 22.5 hr). Thus, FIGS. 3 and 4 show that cytotoxicity is improved as concentration increases for both E7 peptide and E7-conjugated VLP incubated with B16-LUC cells and murine CD8+ HPV16 E7-specific T cells.

Example 6

Batch Consistency of VLP Preparations.

Figures 5A, 5B:
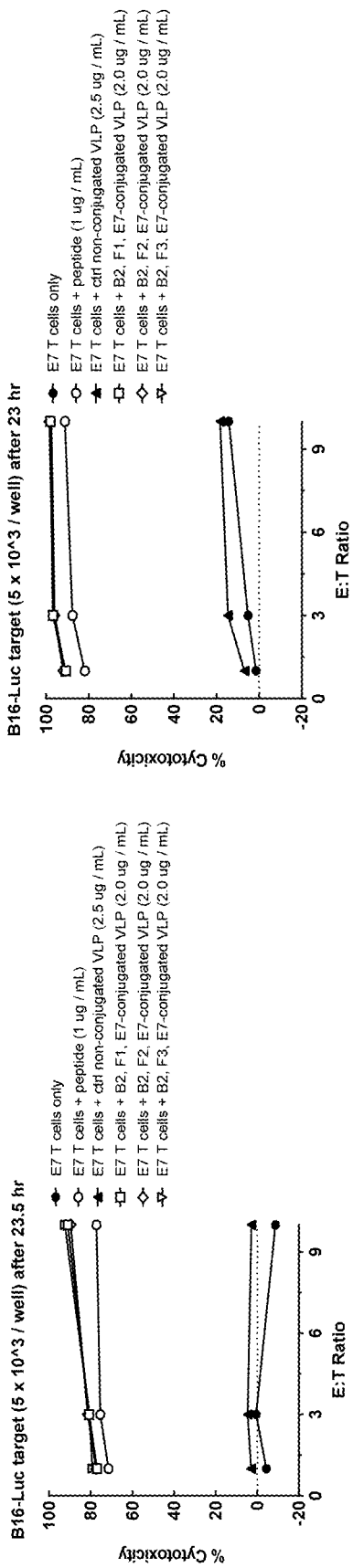
FIG. 5A and FIG. 5B show two separate studies ending at time points, 23 hrs and 23.5 hrs, respectively, of E7 T-cell-mediated cytotoxic effects of three independently created batches of conjugated VLP conjugated to E7 peptide in B16-LUC cells.
Figures 5C, 5D:
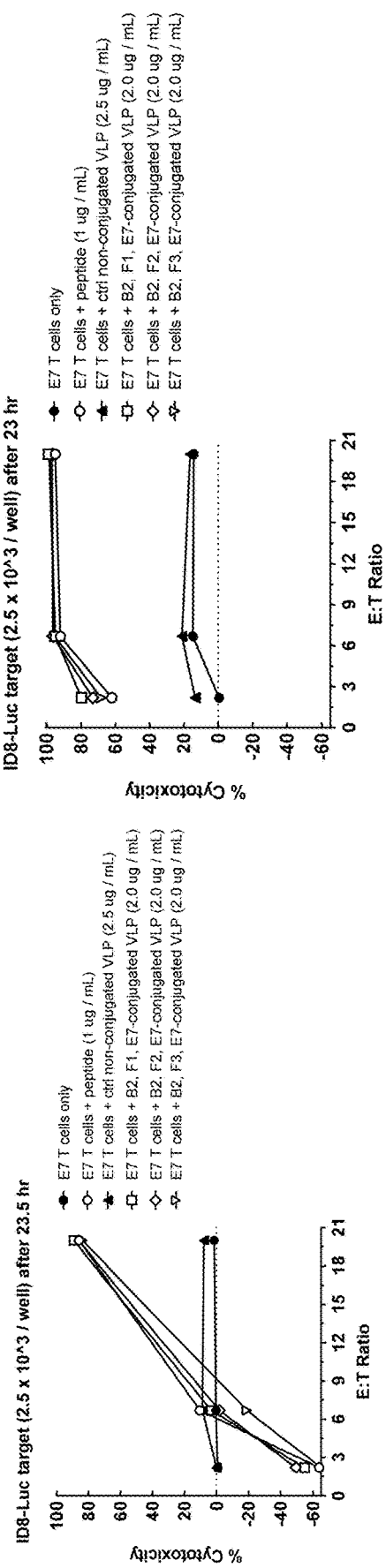
FIG. 5C and FIG. 5D show two separate studies ending at time points, 23 hrs and 23.5 hrs, respectively, of E7 T-cell-mediated cytotoxic effects of three independently created batches of conjugated VLP conjugated to E7 peptide in ID8 cells.

To ensure that the described process of creating conjugated VLPs that could perform immune redirection was consistent, several separately created batches of E7 peptide-conjugated VLP termed "F1, F2, and F3" were examined. Murine B16 (Melanoma/Skin) and ID8 (ovarian) tumor cells overexpressing luciferase gene (B16-luc and ID8-luc) were seeded. 24 hours later the cells were incubated with: (1) an HPV16 E7 peptide RAHYNIVTF (SEQ ID NO: 1) (1 µg/ml); (2) HPV16 E7-conjugated VLP batch F1, F2, or F3 (2.5 µg/ml); (3) an unconjugated (control, 2.5 µg/ml) VLP; or (4) were left untreated. All batches F1-F3 were consistent and were able to activate E7 T cells, and showed killing of B16-luc and ID8-luc cells after 23 or 23.5 hr time points in two separate experiments respectively. (See, FIGS. 5A and 5B, respectively, for B16-luc cells; FIGS. 5C and 5D, respectively, for ID8-luc cells).

Figure 6A:
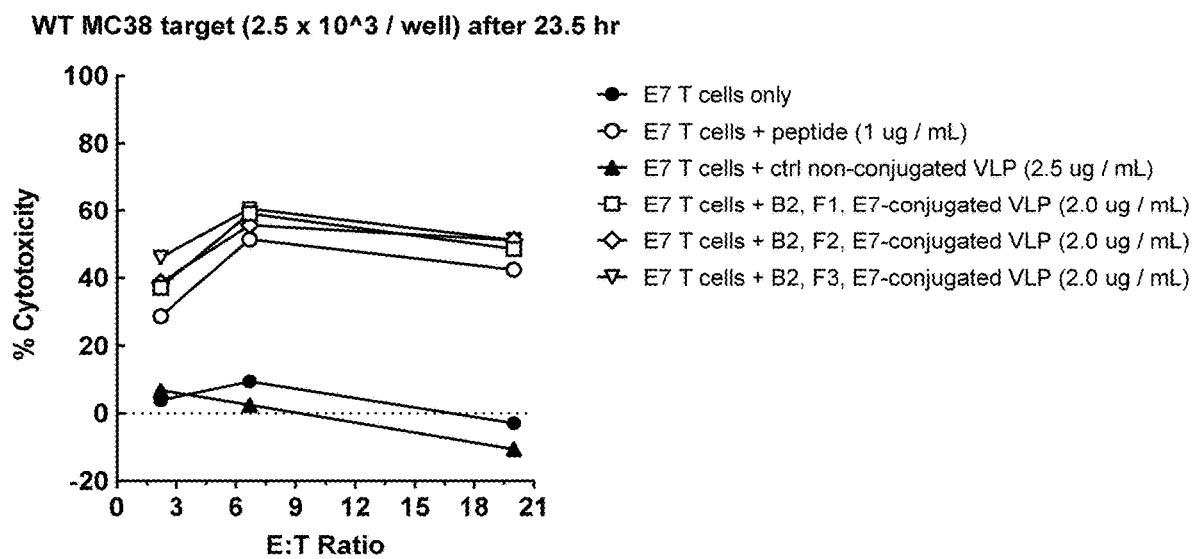
FIG. 6A represents results from the 23 hr timepoint study and FIG. 6B represents results from the 23.5 hr timepoint study.
Figure 6B:
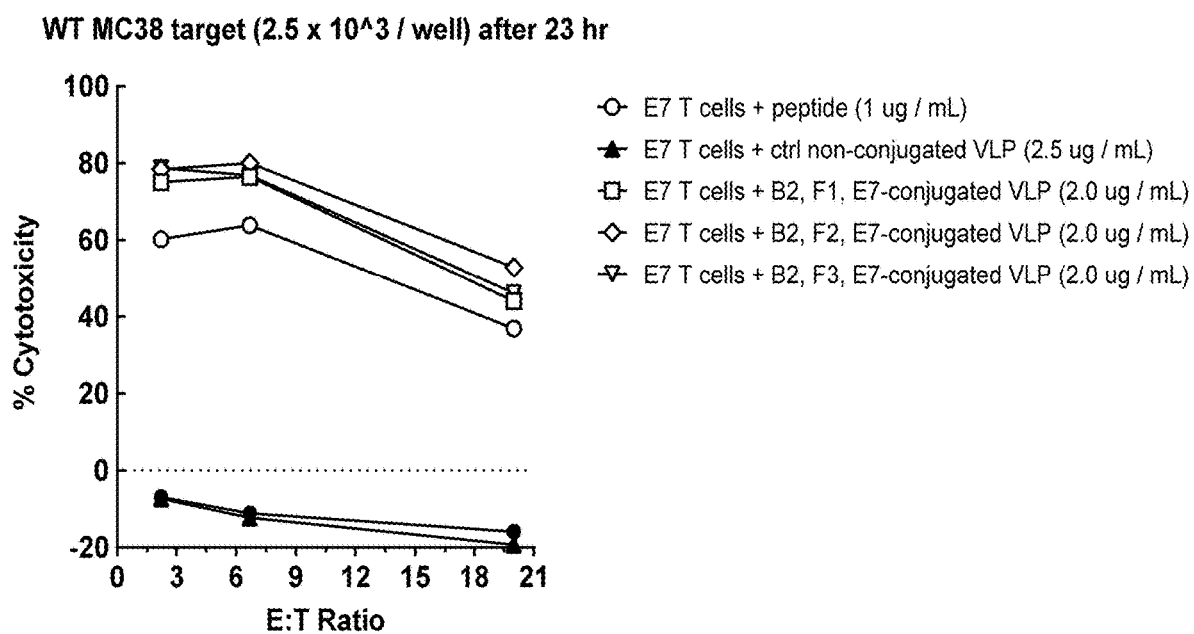
Figure 7A:
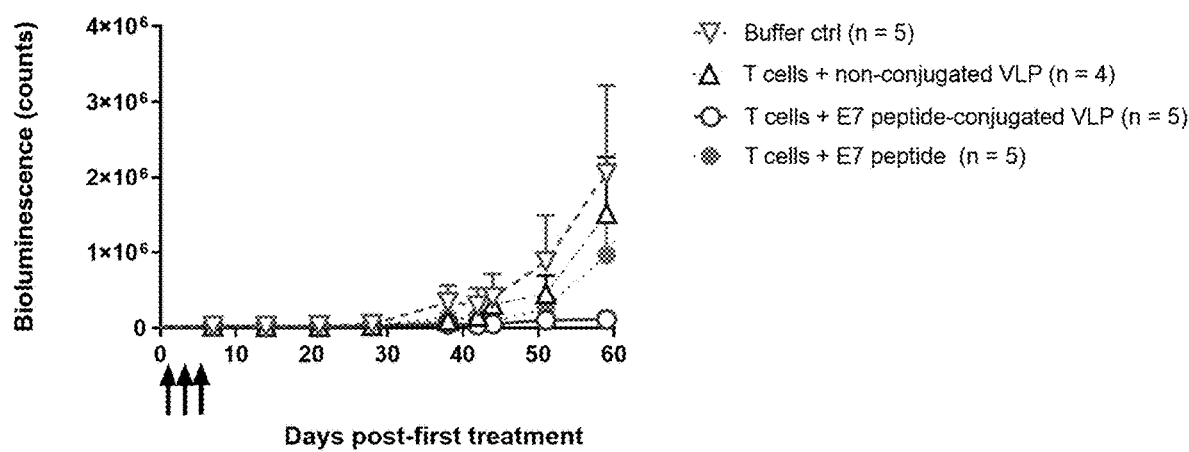
FIG. 7A shows results for all controls and test mice. Individual lines in FIG. 7A represent average tumor growth for all control and test mice respectively FIG. 7B provides buffer control results.
Figure 7B:
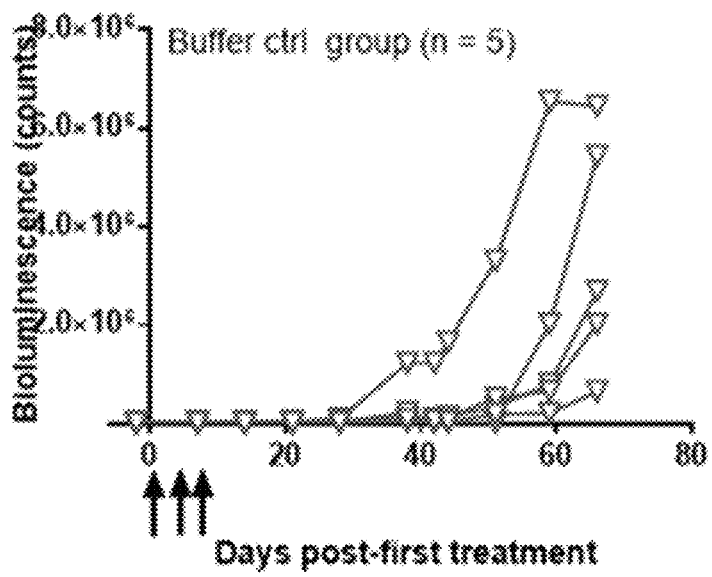
FIG. 7 provides in vivo efficacy data as measured by bioluminescence in a C57BL/6 mouse model injected with either MHC-restricted H-2D$^b$ HPV16 E7 peptide, buffer control, VLP-conjugated to the E7, or unconjugated VLP alone. In each instance the mice were thereafter injected with murine specific H-2D$^b$ HPV16 E7 T cells.
FIG. 7C provides results for unconjugated VLP.
FIG. 7D provides results for E7-conjugated VLP.
FIG. 7E provides results for E7 peptide alone. Individual lines in FIG. 7B represent separate mice in each group.
Figure 7C:
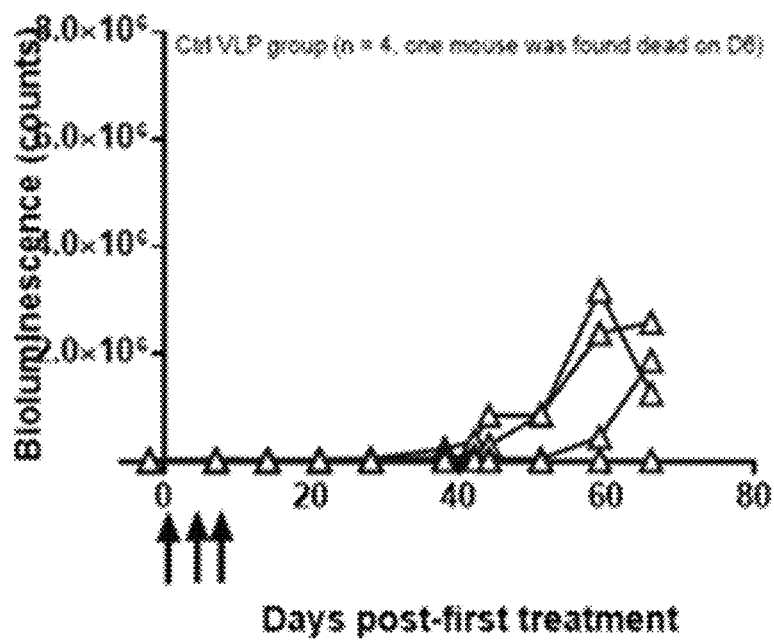
Figure 7D:
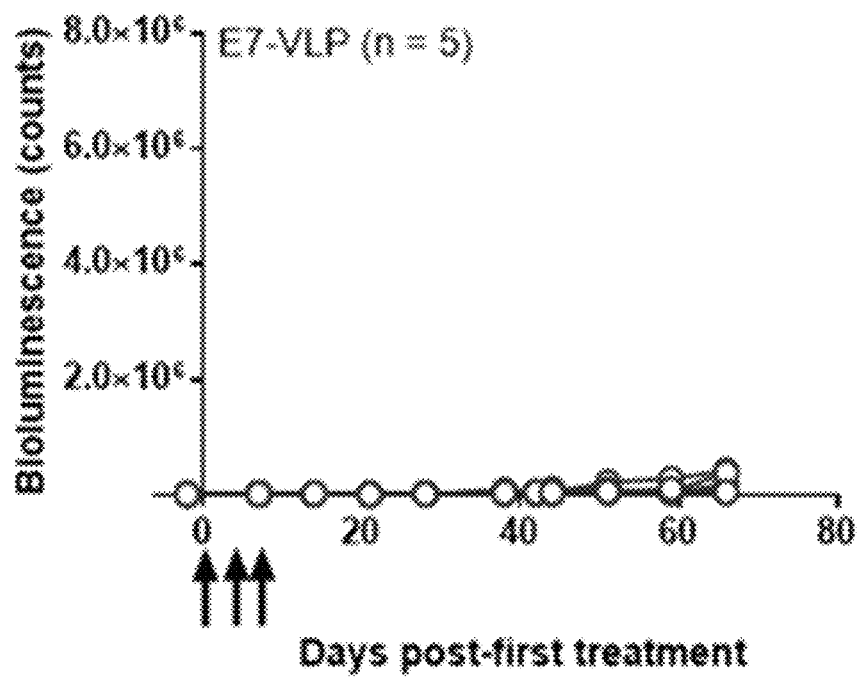
Figure 7E:
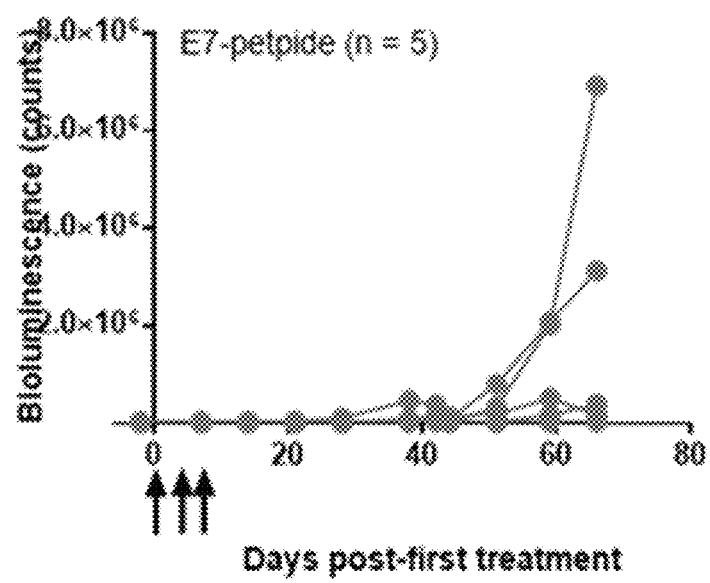

To further demonstrate batch consistency in another tumor cell line, MC38 murine colon tumor line, cells were grown in culture per manufacturer suggested conditions. Under normal circumstances, this cell line will not be killed by murine HPV16 E7-specific T cells since the MC38 cell line does not express the murine E7 antigen. MC38 cells were then treated with: (1) an E7 peptide RAHYNIVTF (SEQ ID NO: 1) (1 µg/ml; (2) HPV16 E7-conjugated VLP, from batch F1, F2, or F3 (2.5 µg/ml); (3) an unconjugated (control, 2.5 µg/ml) VLP; or (4) were left untreated. The cells were then washed and co-cultured with CD8+ HPV16 E7-specific T cells at varying E:T ratios (Effector:Target ratio). The total final volume after co-culture was 200 µL. The cell viability was measured after a certain time of co-culturing. In this example, because MC38 does not express luciferase, the cell viability was measured using an establish cell viability assay reagent: CELLTITER-GLO® (PROMEGA, WI, US). This assay provides a luciferase-expressing chemical probe that detects and binds to ATP, a marker of cell viability. Reduced luciferase activity hence indicates more MC38 cell death suggesting greater immune redirection and hence greater cytotoxicity. All batches F1-F3 were consistent in their functional activity and were able to activate E7 T cells, and showed killing of MC38 cells after 23 and 23.5 hr time points in two separate experiments respectively. (See, FIGS. 6A and 6B, respectively).

Example 7

In Vivo Anti-Tumor Immune Redirection in C57BL/6 Mice with E7-Conjugated VLP

Efficacy of HPV16 E7-conjugated VLPs (conjugated-VLPs conjugated to murine MHC-restricted H-2D$^b$ HPV16 E7 peptide) was assessed in vivo. A total of 20 C57BL/6 mice were injected intra-peritoneally (I.P.) with ID8-luciferase cells ($0.015 \times 10^6$ cells/mouse). On Day 6, mice were checked for tumor growth and establishment via luciferase luminescent imaging. (IVIS® Spectrum in vivo imaging system, Perkin Elmer, Waltham, Mass., US). At day 5, mice are separated into treatment groups and then treated with: (1) buffer only, (2) non-conjugated VLP (100 µg), (3) murine CD8+ HPV16 E7 specific T cells plus E7 peptide conjugated-VLP (n=5, 100 µg), and (4) E7 peptide only (30 Gig, n=5). After 1 hr all mice were injected with approximately $1 \times 10^6$ Day 4 post-stimulated CD8+ HPV16 E7 specific T cells (200 µL per mouse). On day 6 and day 7 treatments were administered a second time for each mouse, but no additional stimulated T cells were added. Mice are then monitored and imaged. Efficacy of treatment is monitored by luminescence imaging which acts as a surrogate for tumor growth and metastasis.

Results are provided in FIG. 7 and show that E7 conjugated VLP therapy was able to redirect E7 specific T-cells to the ID8 murine tumor and control tumor formation even after 60 days post-treatment. (FIG. 7A and FIG. 7D). In contrast, controls such as non-conjugated VLP (FIG. 7C) or buffer only (FIG. 7B) failed to show any tumor protection or control. Although some protection was afforded by peptide only (FIG. 7E), it is important to recount that the overall molarity of peptides on E7 conjugated VLP versus peptide alone was less compared to peptide alone. Further, peptide provided incomplete protection, suggesting that the tumor specific targeting of the VLP is important compared to injection of exogenous peptide alone.

Example 8

In Vivo Anti-Tumor Immune Redirection in B16.F10 Mice with E7-Conjugated VLP

Figure 8A:
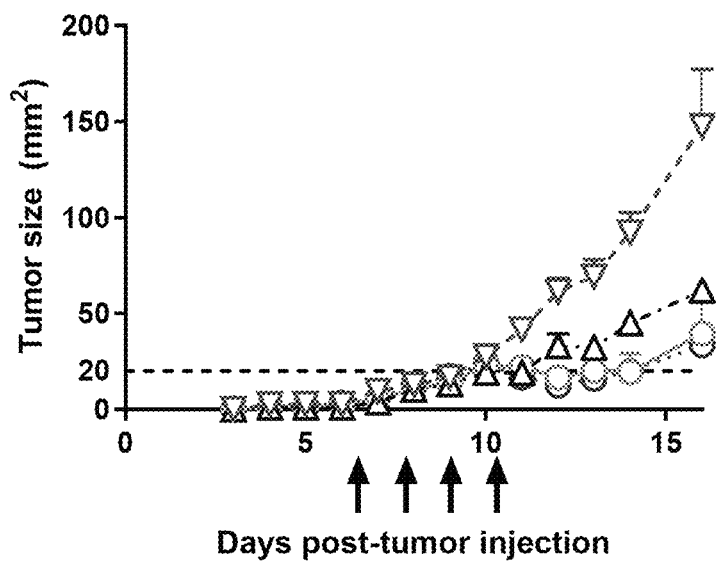
FIG. 8A provides a graphical representation of tumor size data vs. days post-injection of various samples including control VLP, i.e. unconjugated VLP, and E7-conjugated VLP.
Figure 8B:
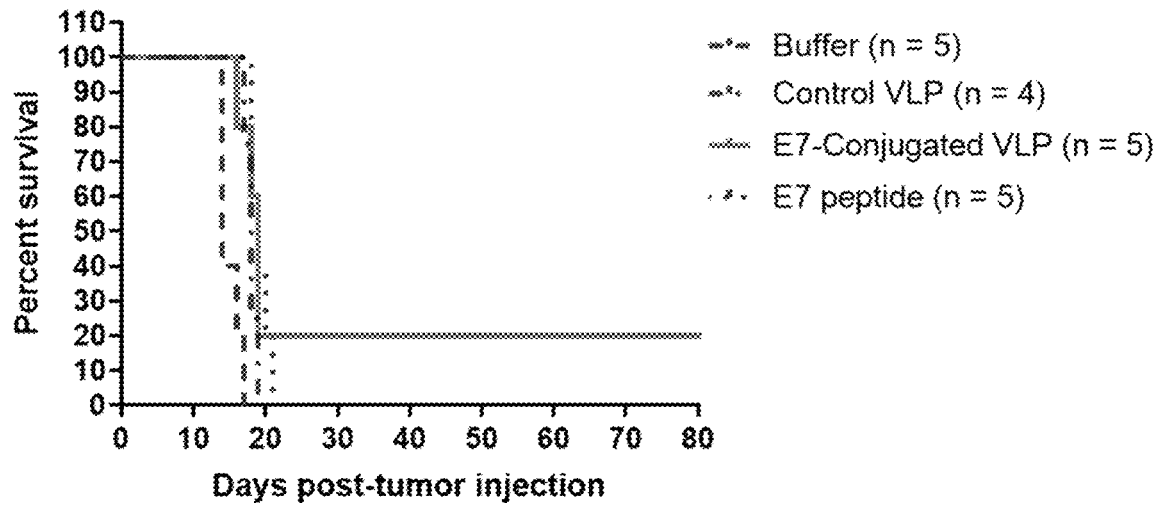
FIG. 8B provides graphical representation of mouse survival rate post B16.F10 tumor cell injection for various samples, including control VLP, i.e. unconjugated VLP alone, and E7-conjugated VLP.

Efficacy of HPV16 E7 VLPs was assessed in another murine tumor model (B16.F10, ATCC, Old Town Manassas, Va., USA). Unlike the ID8 ovarian murine model in which tumors are grown intraperitoneally, the BL16.F10 mouse tumor model is a subcutaneous tumor model. In this experiment, 20 mice were first vaccinated with HPV16 E7 peptide RAHYNIVTF (SEQ ID NO: 1). After 2 weeks, the mice were verified to have an immune response specific to the HPV 16 E7 peptide via HPV16 E7 tetramer (H-2D$^b$/HPV16 E7 (RAHYNIVTF)(SEQ ID NO: 1) MHC Tetramer staining). Briefly, whole blood (2-3 drops) was collected from the tail vein from the mice and checked for antigen specific CD8$^+$ T cell responses by flow cytometry using E7 tetramer (H-2D$^b$/HPV16 E7 (RAHYNIVTF)(SEQ ID NO: 1) MHC Tetramer, MBL International, Woburn Mass., US). Mice were then injected subcutaneously with B16.F10-luciferase cells (0.5×10$^6$ cells/mouse) at the left flank of the thigh. Tumor growth volume was measured using Vernier calipers and volume was calculated using the formula (W$^2$×L)/2, where W (width) is the shorter of the two orthogonal measurements and L (length) is the longer of the two. Mice were monitored every 2 days until palpable tumors (~7 mm in diameter) were observed. Subsequently, mice were divided into various treatment groups, as follows: (1) buffer only (n=5); (2) non-conjugated VLP ("Control" VLP) (n=5); (3) E7-conjugated VLP (n=5); and (4) peptide alone. All treatment groups received 5 µg indicated component per dose. A total of four treatments were administered to the mice, every other day. Mice were then monitored to assess tumor volume. Efficacy of treatment was monitored via tumor volume growth and survival in which the endpoint survival is when tumor growth volume reaches 1500 mm$^3$. Results showed that a delayed effect in tumor growth was observed in control VLP, E7 conjugated VLP, and E7 peptide groups. (See, FIG. 8A and FIG. 8B). However, eventually all tumors reached the end point size of 1500 mm$^2$ (FIG. 8A). All control mice reached their survival endpoint by day 17 (FIG. 8B). Treated mice survived up to day 19 to 22. One mouse from the E7 conjugated VLP-treated group had all tumors regressed, completely, and remained tumor free for over 80 days. (See, FIG. 8B).

To further test the importance of specific viral memory T-cells and whether their increased presence would lead to an improved therapeutic outcome, the mice were also separated into groups of "high" and "low" T-cell frequencies (see below for explanation), i.e. those mice that had a higher frequency of peripheral HPV16 E7 T cells in their PBMCs, vs. those that did not. Mice were first vaccinated with HPV16 E7 peptide RAHYNIVTF (SEQ ID NO: 1) to generate the anti-viral immune memory response. The vaccinated mice were left alone for approximately 6 weeks to establish immune memory to HPV16 E7. To check for immunogenicity, mice were separated into "high" and "low" T-cell frequencies. Briefly, whole blood (2-3 drops) was collected from the tail vein from the mice and checked for antigen specific CD8$^+$ T cell responses by flow cytometry using E7 tetramer (H-2D$^b$/HPV16 E7 (RAHYNIVTF) (SEQ ID NO: 1) MHC Tetramer, MBL International, Woburn Mass., USA). The frequency of HPV16 E7 Tetramer-specific T cell response was between 1-50%. Mice that had a T cell frequency ranging between 1-14% were considered "low" and mice that had a T cell frequency ranging between "15%-50%" were considered "high." All mice were then injected subcutaneously with B16.F10 melanoma tumor cells (0.5×10$^6$ cells/mouse) at the left flank of the thigh. Tumor growth volume was measured using Vernier calipers and volume was calculated using the formula (W$^2$×L)/2, where W (width) is the shorter of the two orthogonal measurements, and L (length) is the longer of the two. Tumor volumes were allowed to reach 50 to 100 mm$^3$ before starting treatments with E7 conjugated VLPs or control VLPs (non-conjugated VLP).

Figure 8C:
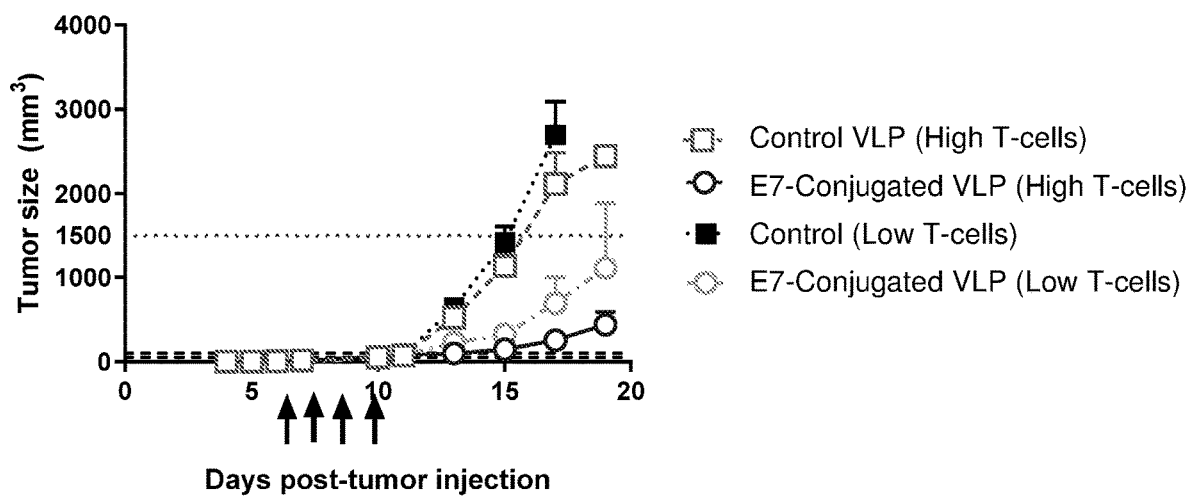
FIG. 8C and FIG. 8D are similar to FIGS. 8A and 8B, except that the HPV16 E7 immune response was in memory phase, i.e. mice were treated 6 weeks post peptide RAHYNIVTF (SEQ ID NO: 1) vaccination; and that the tumor volumes prior to treatment was between 50-100 mm$^3$. The mice were then challenged with tumors and E7-conjugated VLP injected into the mice and survival rates quantitated.
Figure 8D:
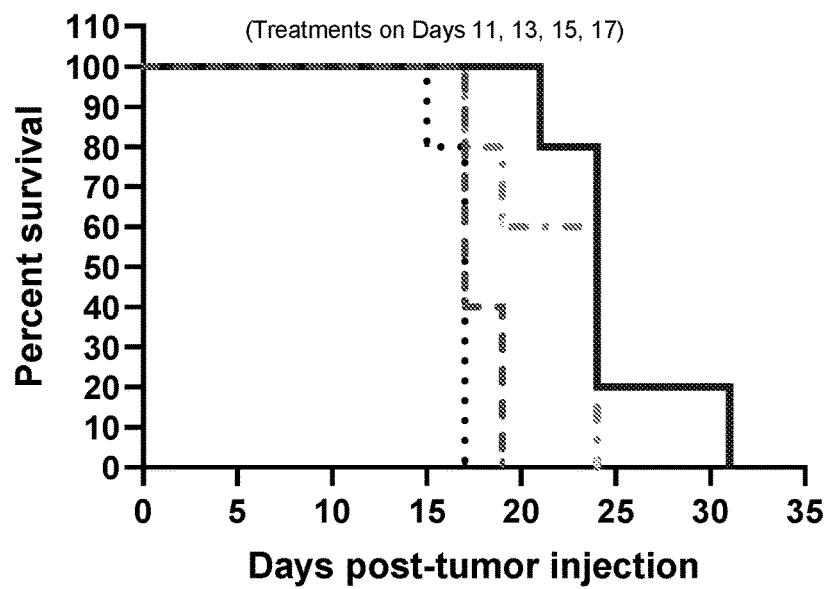

Results are depicted in FIG. 8C and FIG. 8D and show that a delayed effect in tumor growth was observed in mice treated with E7 conjugated VLP but not in control groups treated with VLP alone. (See, FIG. 8C). However, eventually all tumors reached the end point of 1500 mm$^2$ by day 32 (FIG. 8D). All control mice reached their survival endpoint by day 17. (See, FIG. 8B). Treated mice survived up to day 24 for mice with "low" T-cell frequency, or up to day 32 for mice with "High" T-cell frequency. (FIG. 8D). In the absence of treatment, there was no difference in B16.F10 tumor growth between mice that had higher or lower frequency of E7 specific memory T-cells. (FIG. 8C). In contrast, tumor growth in the treatment groups seemed to suggest that the mice with higher E7 T-frequencies responded better to E7 conjugated VLP treatment, as the tumor growth was better controlled (FIG. 8D). However, further study of the data revealed no obvious trend when individual mice were scrutinized. This could be due to the "variable" tumor size as treatment was administered once all mice had tumors between 50 to 100 mm$^3$. In general, it was observed that mice who had smaller tumors (closer to 50 mm$^3$) responded better to the conjugated VLP treatment, but this did not necessarily correlate with a higher pre-existing T-cell PBMC frequency. This suggests that the immune redirection effect could be due to other potential E7-specific T cells, i.e. tissue resident memory T-cells. Nonetheless, these data suggest that immune redirection is possible even in a difficult B16.F10 mouse model that is known to be checkpoint refractory.

Example 9

Detection of VLP-Peptide Loading onto MHC-I Receptors on Mouse Tumor Cells In Vitro An assay system was developed to directly detect peptide-loading from conjugated-VLP onto MHC I receptors on tumor cells. This assay involves the use of OVA-conjugated VLPs ("OVA-VLPs") and an antibody (fluorophore-conjugated anti-OVA (SIINFEKL)/K$^b$ (SEQ ID NO: 2) antibody, MBL International, Woburn, Mass., US) that specifically recognizes the OVA (SIINFEKL)/$K^b$ (SEQ ID NO: 2) complex, but not any other peptide/MHC-I complexes.

To this end, target cells (B16-LUC, ID8-LUC, and MC38) were plated at $0.02 \times 10^6$ cells/well on a 96-well plate. The next day, OVA-conjugated VLPs (2.5 µg/ml) were incubated with target tumor cells for 1 hr at 37° C., followed by extensive washing to remove any unbound materials. Next, fluorophore-conjugated anti-OVA (SIINFEKL)/$K^b$ (SEQ ID NO: 2) antibody was added directly to the cells at a dilution of 1:100 (total volume of 100 µL, i.e. 1 µL) for 30 minutes at 4° C. Following this incubation, excess antibodies were washed off and the cells were analyzed for the presence of the OVA (SIINFEKL)/$K^b$ (SEQ ID NO: 2) complex by FACS flow cytometry. As expected, the OVA (SIINFEKL)/$K^b$ (SEQ ID NO: 2) complex was detected in three different mouse tumor cells after incubation with OVA-conjugated VLPs. (See, FIG. 9).

Figure 9A:
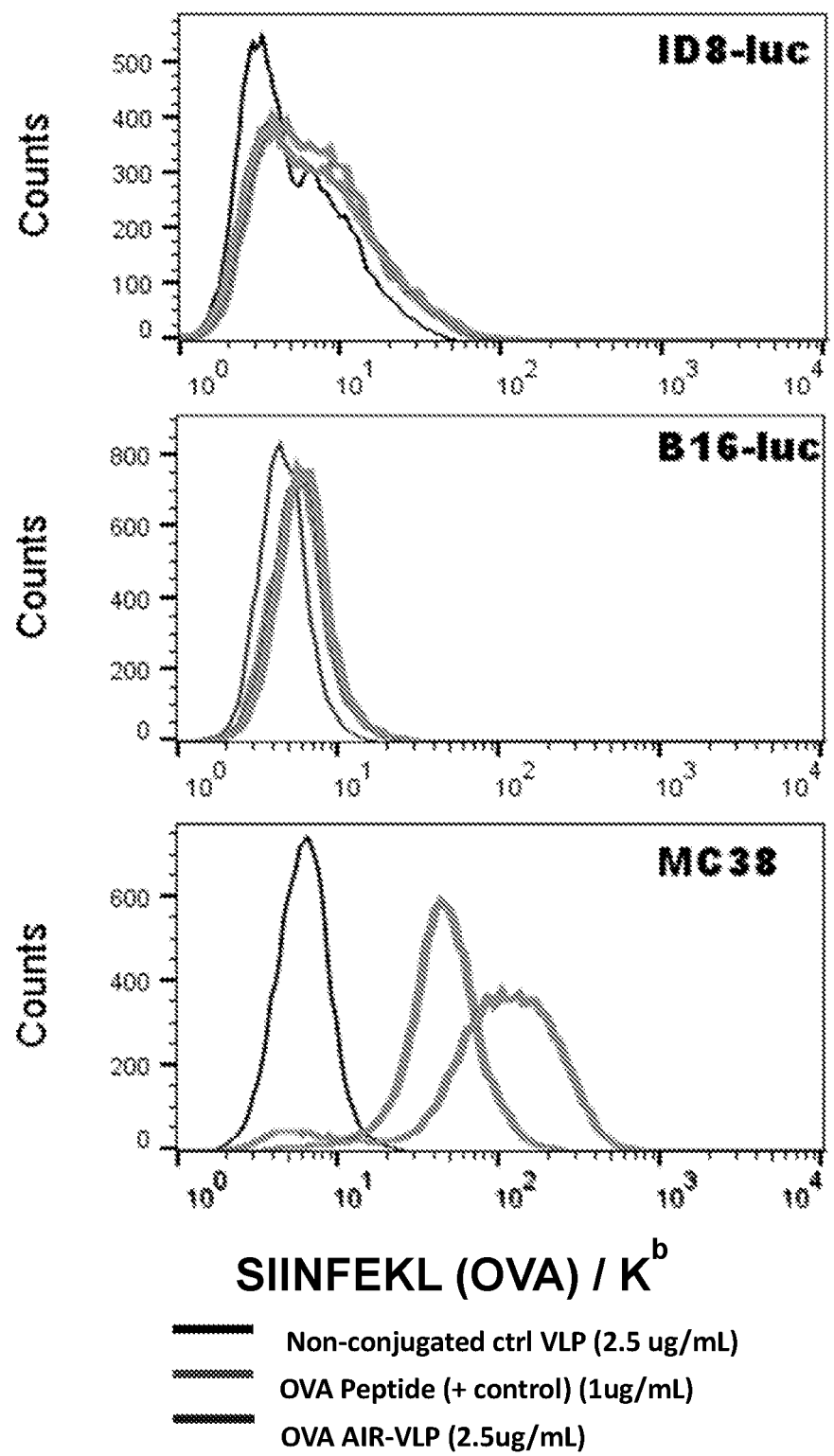
FIG. 9A shows FACS data resulting from incubation of ID8-LUC (top panel), B16-LUC (middle panel), and MC38 (lower panel) cells with OVA peptide alone or OVA-conjugated VLP.
Figure 9B:
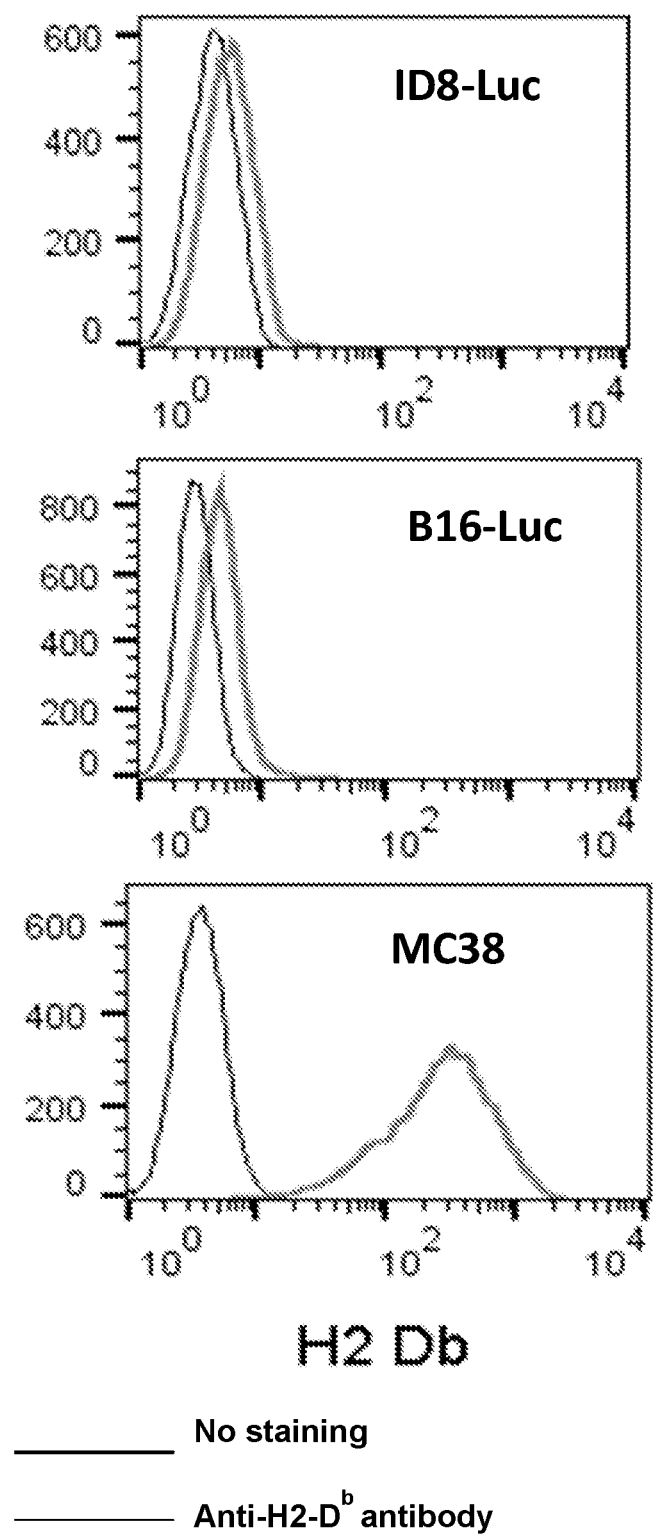
FIG. 9B shows the same cells, ID8-LUC (top panel), B16-LUC (middle panel), and MC38 (lower panel), stained by binding of an H-2D$^b$ antibody specific for MHC-I complexed with OVA peptide.

FIG. 9A shows FACS data resulting from incubation of ID8-LUC (top panel), B16-LUC (middle panel), and MC38 (lower panel) cells with OVA peptide alone or OVA-conjugated VLP. This indicates that OVA-conjugated VLPs bind to these tumor cells and their peptides were cleaved, followed by binding of the cleaved peptide to the tumor MHC-I molecules. Therefore, the design of the VLPs is verified to perform the intended functions, i.e. the epitope peptide is cleaved by furin and the peptide is bound by MHC I molecules on the tumor cell surface. These findings should be applicable to other viral peptides, other than OVA. It is also important to note that differential OVA (SIINFEKL)/$K^b$ (SEQ ID NO: 2) complex was detected across the murine tumors and further studies suggest that loading might be dependent on availability of surface MHC Class 1 on tumor surfaces (not shown). FIG. 9B shows the same cells, ID8-LUC (top panel), B16-LUC (middle panel), and MC38 (lower panel), stained by binding of an $H2-D^b$ antibody (PE anti-mouse H-2D b antibody, anti-$H-2D^b$, Biolegend, San Diego, Calif., US) specific for MHC-I complex.

Example 10

Redirection of Human CD8+ T Cell Viral Immunity Against Human Immortalized Tumor Cell Lines Using VLP Conjugated to HCMV Pp65 Antigen The ability of the described conjugated VLP system to trigger immune redirection using other antigens or epitopes was further explored by investigating the ability of human cytomegalovirus (HCMV) pp65 antigen-conjugated VLP to redirect immunity. The conjugated VLPs were generated as described above. The rationale to choose HCMV was based on knowledge that HCMV is highly prevalent (infecting 50-90% of the human population) and mostly asymptomatic in healthy individuals. (See, Longmate et al., *Immunogenetics*, 52(3-4):165-73, 2001; Pardieck et al., *F1000Res*, 7, 2018; and van den Berg et al., *Med. Microbiol. Immunol*, 208(3-4):365-373, 2019). Importantly, HCMV establishes a life-long persistent infection that requires long-lived cellular immunity to prevent disease. Hence, it is rational to hypothesize that a complex adaptive cell-mediated anti-viral immunity developed over many years to strongly control a viral infection in an aging person can be repurposed and harnessed to treat cancer.

In Vitro Cytotoxicity Assays.

Figures 10A, 10B, 10C:
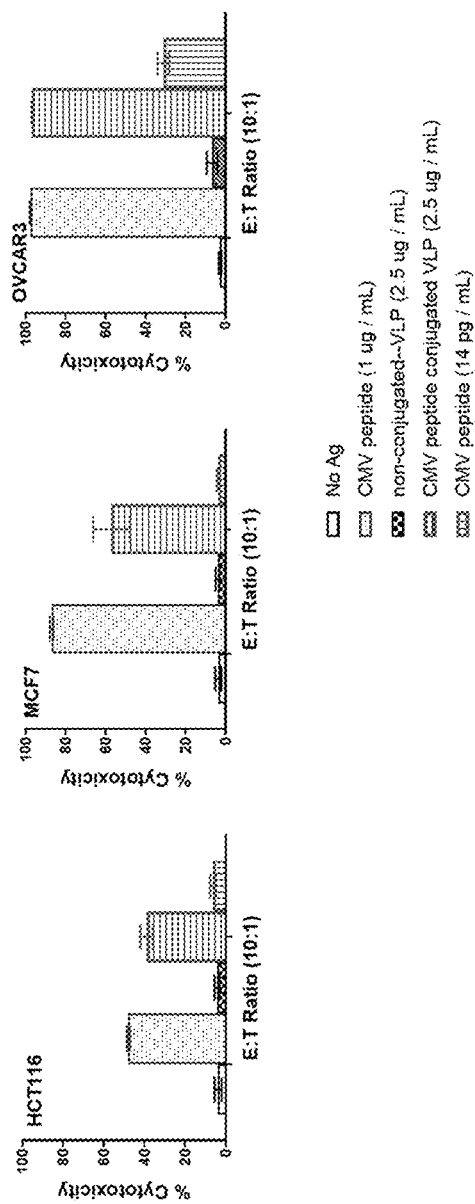
FIG. 10 provides bar graph data for CMV-conjugated VLP triggered immune redirection cytotoxicity of various immortalized human tumor cell lines including HLA.A2 positive HCT116 cells (FIG. 10A), OVCAR3 cells (FIG. 10B), and MCF7 cells (FIG. 10C). The bars in each graph, from left to right, represent tests performed with no antigen, CMV pp65 HLA-A*0201 (NLVPMVATV)(SEQ ID NO: 3) peptide (henceforth "CMV peptide") alone at 1 µg/mL, VLP alone, i.e. non-conjugated VLP at 2.51 µg/mL, CMV peptide conjugated to VLP at 2.5 µg/mL, and CMV peptide alone at 14 pg/mL.

Human target cells, HTC112, human colon cancer, MCF7, human breast cancer or OVCAR 3, human ovarian cancer (ATCC, Manassas, Va., US) were seeded overnight at 0.01 to $0.2 \times 10^6$ per well per 100 µL per 96 well plate. The next day (about 20 to 22 hrs later), each cell line was incubated for one hour at 37° C. under the following conditions: (1) CMV peptide at a final concentration of 1 µg/mL, (2) control VLP (no peptide) at a final concentration of 2.5 µg/mL, (3) CMV-conjugated VLP at a final concentration of 2.5 µg/mL, and CMV peptide at a final concentration of 14 pg/mL (equivalent to peptide conjugated to CMV-VLP at 2.5 µg/mL). After 1 hour, the cells were washed vigorously with 200 µL of media for three times to remove non-specific binding. Human patient donor CMV T cells (ASTARTE Biologics, Seattle, Wash., US) were added at the E:T (effector cell:target cell) ratio of 10:1 and incubated in a tissue culture incubator for 24 hrs. The total final volume after co-culture was 200 µL. The cell viability was measured after a certain time of co-culturing. In this example, because the above human cells does not express luciferase, the cell viability was measured using an establish cell viability assay reagent: CELLTITER-GLO® (PROMEGA, WI, US). This assay provides a luciferase-expressing chemical probe that detects and binds to ATP, a marker of cell viability. Reduced luciferase activity hence indicates more human immortalized cell death suggesting greater immune redirection and hence greater cytotoxicity The results are provided in FIG. 10. CMV conjugated VLP was effective in killing human healthy donor CMV pp65-specific CD8+ T-cells (Astarte Biologics, Inc., Bothell, Wash., US), immortalized HLA.A2 positive human colon cancer cells (HCT116, FIG. 10A), human ovarian cancer cells (OVCAR3, FIG. 10B) and human breast cancer cells (MCF7, FIG. 10C). In both the mouse and human systems, control VLPs, i.e., no peptide conjugation, did not induce killing of the target cells, nor did co-incubation of CD8+ T cells with tumor cells alone. In these series of in vitro studies using human cell lines, it was determined that 1 µg/mL of CMV peptide is equivalent to 1060 nM peptide, whereas the molar equivalent of CMV peptide conjugated to the surface of the VLP in 2.5 µg/mL of CMV-conjugated VLP was ~0.024 nM. Thus, a comparable T-cell redirection killing of tumor cells was triggered by the conjugated VLP despite using almost 44,000 times less than the CMV peptide alone. Importantly, it was determined that this 0.024 nM molar equivalent concentration of CMV (pp65) peptide alone that is conjugated to VLP was 14 pg/mL. When cytotoxicity was tested at 14 pg/mL of the free peptide alone, little to no killing of tumor cells was observed in all three human target cells (FIG. 10C). This highlights the potency of the conjugated VLP in enhancing peptide loading compared to exogenous free peptide loading-alone onto tumor cells to facilitate immune redirection.

Example 11

VLP Conjugation Methods

Two conjugation approaches were tested as candidates for conjugation of the VLP to the fusion protein: (1) wild type HPV vaccine (WT-VLP); and (2) a conjugated HPV vaccine (RG1 VLP which has 2 additional cysteine residues per single L1 monomer and therefore 720 extra cysteines on the RG1 VLP surface compared to WT VLP). For each test, the VLP was first reduced by reaction with tris(2-carboxyethyl) phosphine (TCEP), for 1 hour at room temperature. This reduction step was required to "release" free cysteines on the VLP surface for the next step—maleimide conjugation of the peptides to the VLP. Protocols followed for reduction and maleimide conjugation utilizing maleimide molecules directly synthesized upstream of the recall protein were as described above.

The RG1 VLP L1 protein sequence with the additional RG1 peptide sequence insertion is as follows (SEQ ID NO: 87):

```
MSLWLPSEAT VYLPPVPVSK VVSTDEYVAR TNIYYHAGTS

RLLAVGHPYF PIKKPNNNKI LVPKVSGLQY RVFRIHLPDP

NKFGFPDTSF YNPDTQRLVW ACVGVEVGRG QPLGVGISGH

PLLNKLDDTE NASAYAQLYK TCKQAGTCPP DIIPKVANAG

VDNRECISMD YKQTQLCLIG CKPPIGEHWG KGSPCTNVAV

NPGDCPPLEL INTVIQDGDM VDTGFGAMDF TTLQANKSEV

PLDICTSICK YPDYIKMVSE PYGDSLFFYL RREQMFVRHL

FNRAGAVGEN VPDDLYIKGS GSTANLASSN YFPTPSGSMV

TSDAQIFNKP YWLQRAQGHN NGICWGNQLF VTVVDTTRST

NMSLCAAIST SETTYKNTNF KEYLRHGEEY DLQFIFQLCK

ITLTADVMTY IHSMNSTILE DWNFGLQPPP GGTLEDTYRF

VTSQAIACQK HTPPAPKEDP LKKYTFWEVN LKEKFSADLD

QFPLGRKFLL QAGLKAKPKF TLGKRKATPT TSSTSTTAKR

KKRKLSR
```

Figure 11:
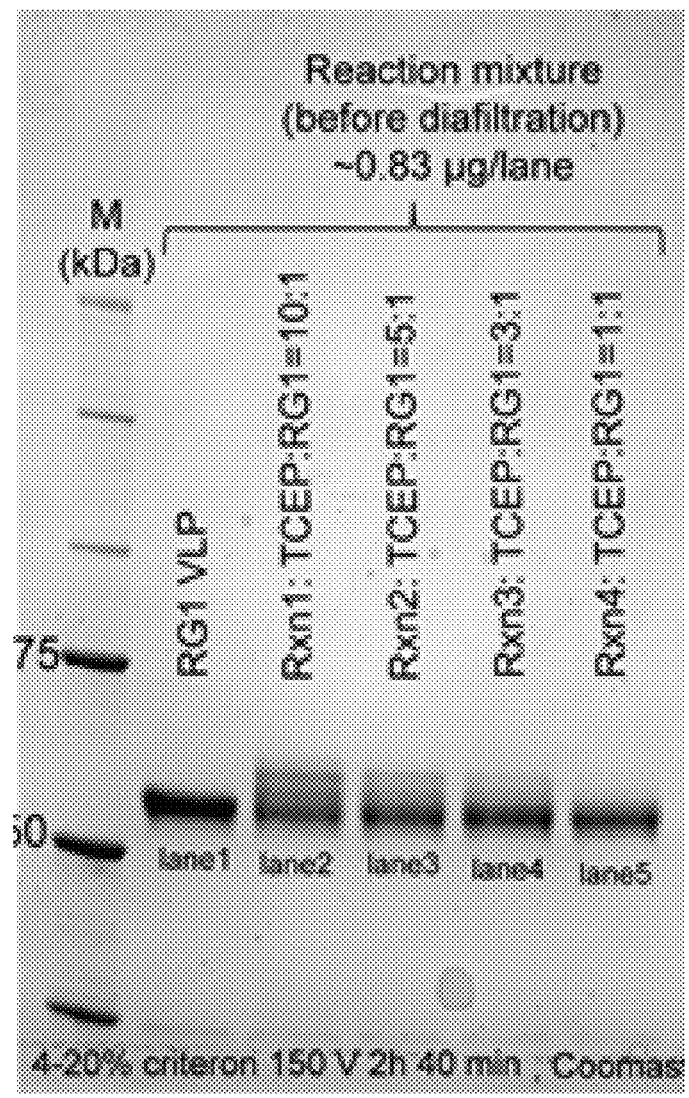
FIG. 11 is a photograph of an SDS-PAGE analysis of reducing conditions for VLP conjugation. The left lane is a molecular weight standards lane. The next lanes in the gel are various conjugation reaction conditions utilizing tris(2-carboxyethyl)phosphine (TCEP) in various ratios to RG1 VLP.
Figure 12:
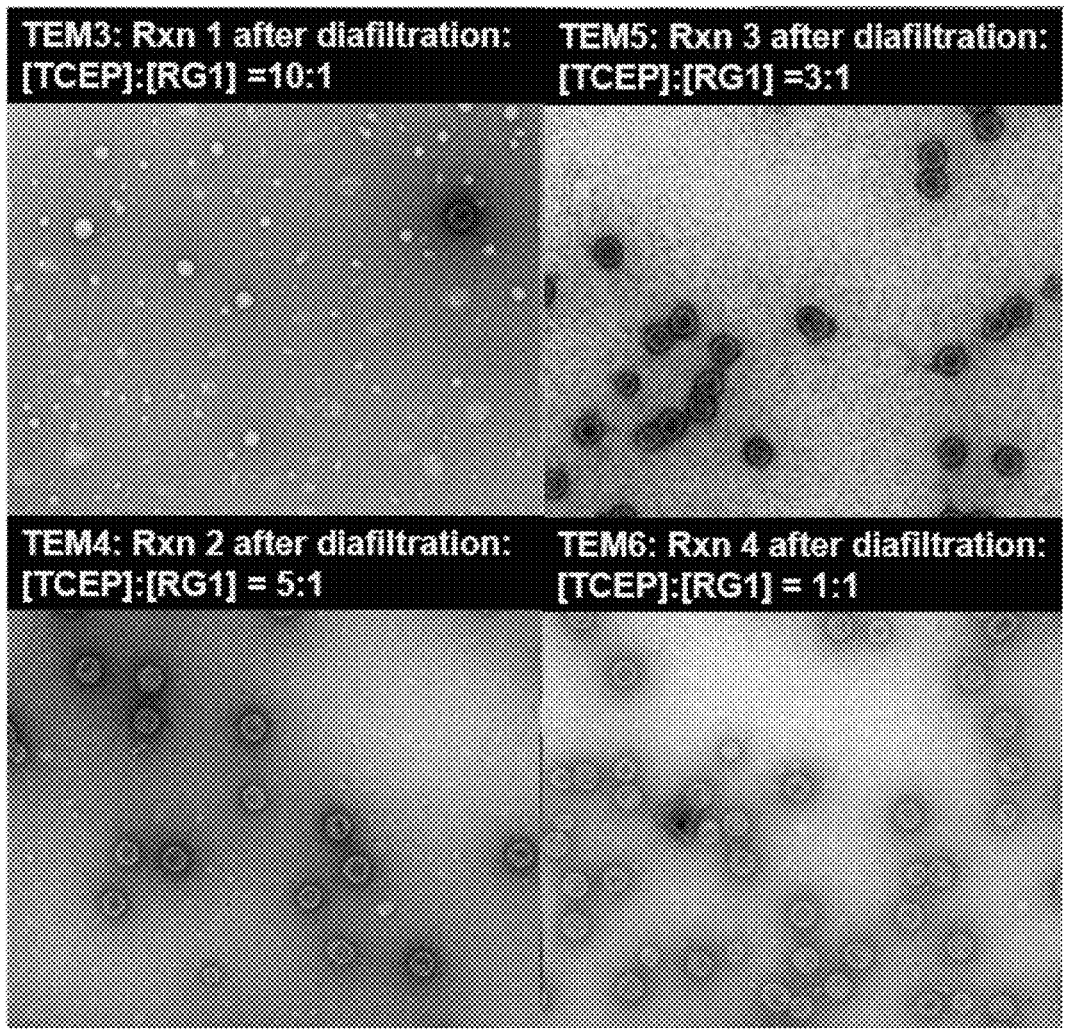
FIG. 12 is a photomicrograph generated by transmission electron microscopy (TEM) of conjugated VLPs post conjugation reaction utilizing varying ratios of TCEP to RG1 VLP. The upper left panel shows the results of conjugation following reaction of TCEP with RG1 at a 10:1 ratio. The such as inhibiting, reducing, or preventing or reducing tumor mass, progression and/or metastasis.
Figure 13:
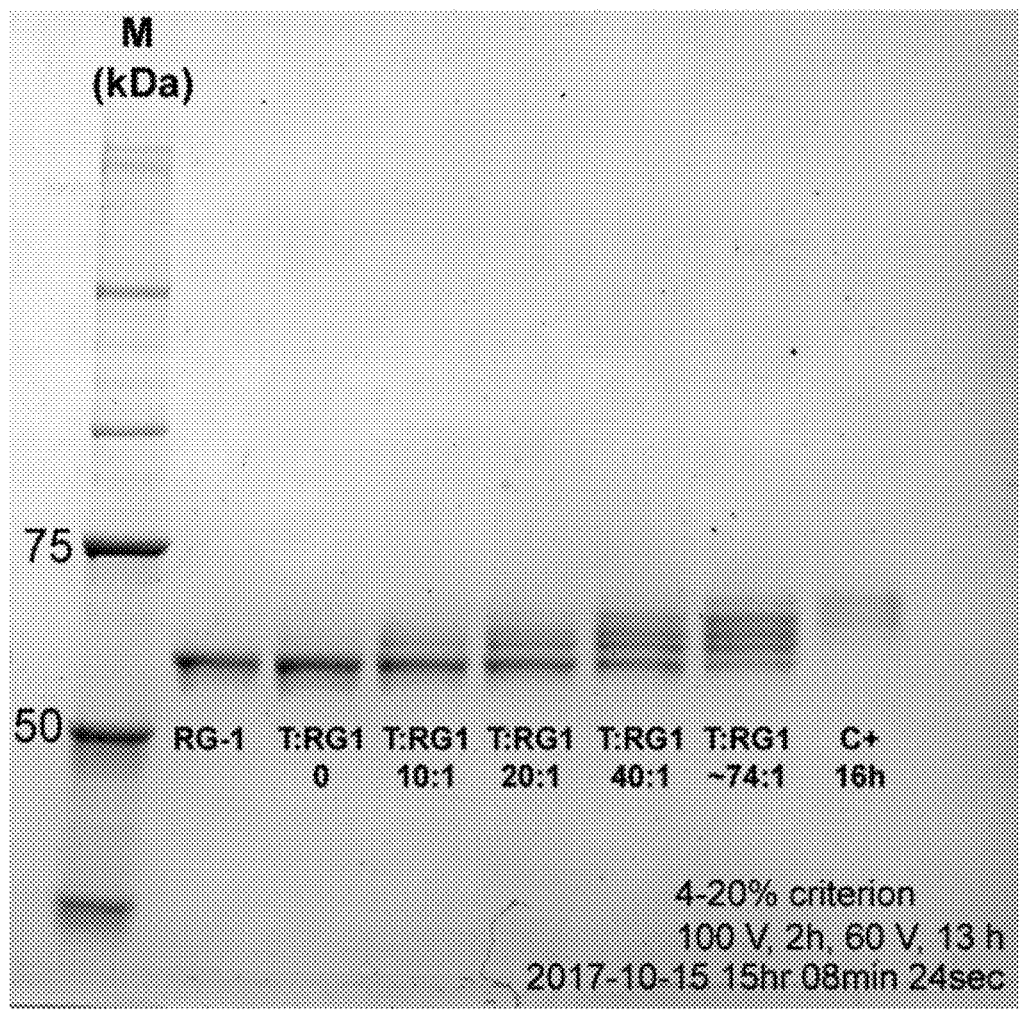
Figure 14A:
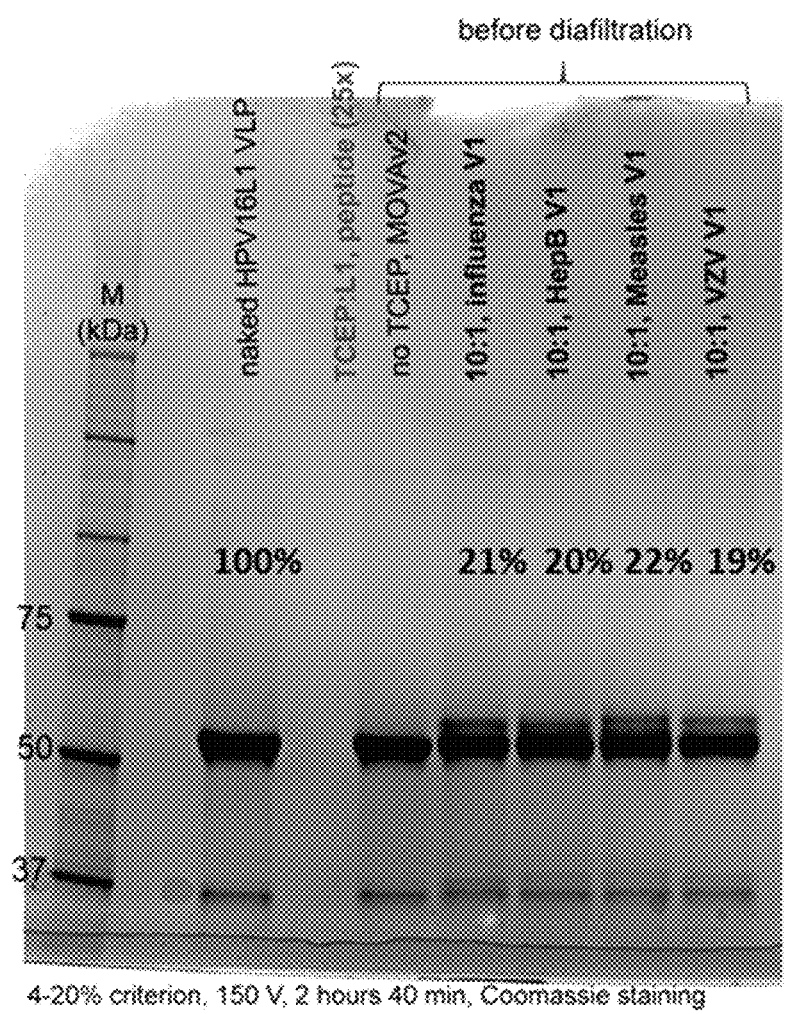
Figure 14B:
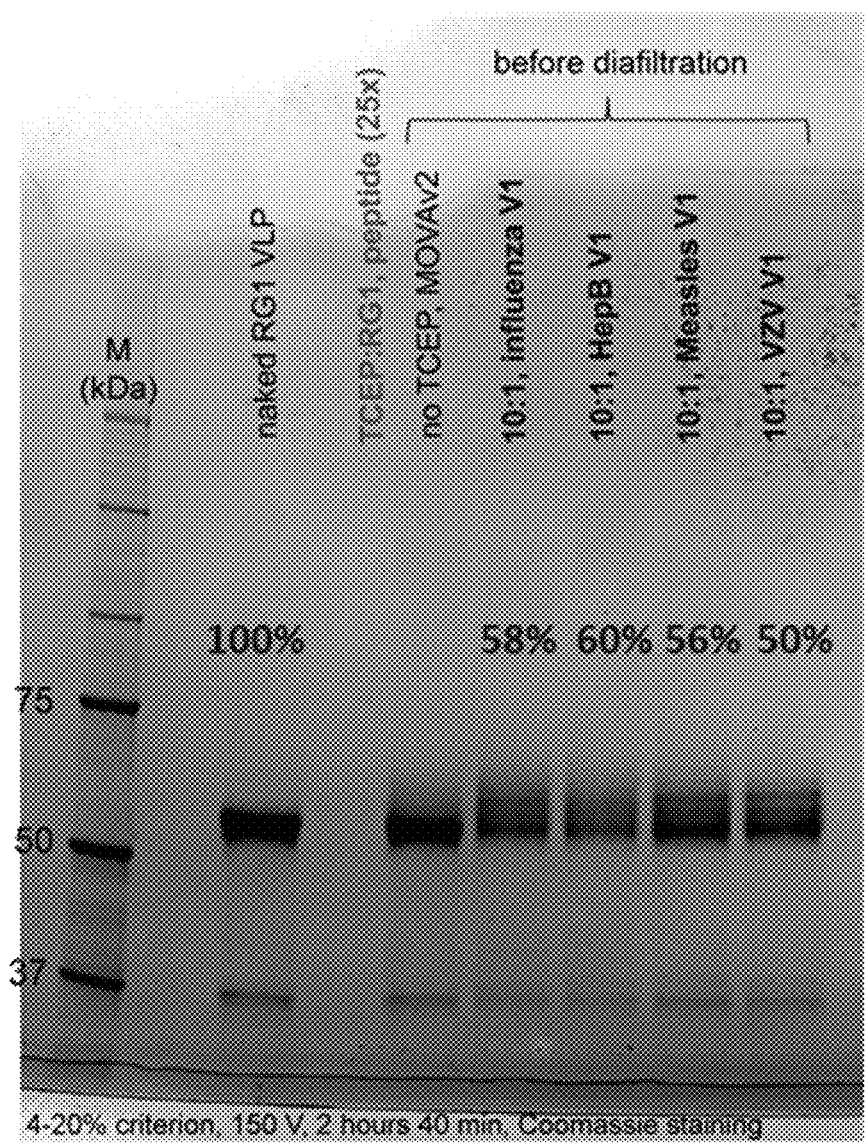

Little to no detectable conjugation occurs if there is no reduction step (see FIG. 13, lane 3, and FIG. 14, lane 5). The efficiency of conjugation is determined by performing Coomassie staining of the VLP on SDS-PAGE (CRITERION™ gels, 4-20% acrylamide, BioRad, Hercules, Calif., US) to determine relative amounts of conjugated and unconjugated VLP. (See, FIG. 11). If no conjugation occurs, there will only be a single band as seen in the TCEP:RG1 VLP 1:1 lane. In contrast, the multiple bands in the TCEP:RG1 ratios from 3:1-10:1 show conjugation occurring and therefore also validating the importance of the reduction step. It is also known that the VLPs are held by disulfide bonds and thus addition of TCEP might harm the VLP, however ratios of TCEP:RG1 of 5:1 and 3:1 show intact conjugated VLPs under TEM (transmission electron microscopy), thereby showing a TCEP amount suitable for RG1 conjugation without affecting particle integrity. (See, FIG. 12)

The relationship of how TCEP concentration determines the coupling efficiency of the fusion protein to the VLP was further investigated at additional ratios of reducing agent to VLP (up to 74:1). (See, FIG. 13). At the highest ratios of TCEP to RG1 (e.g. 74:1), up to 5 coupling sites were present on a single L1 monomer. In contrast, WT-VLP, no matter what ratio of TCEP was tested, yielded only one coupling site per L1 monomer.

Example 12

Human Conjugated VLP Trigger Tumor Cytotoxicity In Vitro and In-Vivo.

The ability to selectively load tumor cells with a common infectious viral antigenic peptide that can easily be recognized and be eliminated by a pre-existing immune recall response is to be evaluated both in vitro and in vivo using various murine models. As seen in Examples 1 through 11, using a murine MHC-restricted H-2D$^b$ HPV16 E7 peptide from the HPV (human papillomavirus) type 16 E7 antigen, a HPV16 E7-conjugated conjugated VLP (E7-VLP) was generated and shown to specifically bind to the tumor cells ID8 (ovarian), B16 (melanoma), and MC38 (colon). Cleavage of the E7 peptide from the E7-conjugated VLP leads to specific E7 peptide binding to MHC class I receptors on tumor cells thereby rendering those tumor cells susceptible to antigen-specific CTL-mediated killing, in this case murine CD8+ HPV16 E7 specific T cells. As seen in Example 10, using human cytomegalovirus (HCMV) pp65 antigen-conjugated VLPs, this result has also been extended to human healthy donor CMV pp65-specific CD8+ T-cells.

Since most human individuals have or might have pre-existing immunity against influenza, HPV16, CMV, EBV, and other childhood vaccines (MMR, chicken pox, HEPB), the same experimental methods may be adopted to conjugate the described VLPs to other immunogenic HLA-A2-restricted peptides. HLA-A2 restricted epitopes will be chosen for these experiments as these are the most prevalent human MHC class I allele in the U.S. Various VLPs were conjugated to an HLA-A2 restricted epitope with a furin cleavage site at its N2-terminus as described above. The specific epitopes are provided in Table 4.

TABLE 4

VLPs Conjugated to an HLA-A2 restricted epitope comprising a furin cleavage site

| Virus | Approved Human Vaccine where epitope can be detected (Source) | Epitope | SEQ ID NO |
|---|---|---|---|
| Influenza A | Afluria-Trivalent or Flublok Quadrivalent if aged 18-64, Fluzone High-dose OR Fluad if 65 and older, Flucelvax Quadrivalent for 4-18 years old (and older actually) | FMYSDFHFI<br>GILGFVFTL | 77<br>68 |
| Hepatitis B | Engerix (GSK) | FLPSDFFPSV | 41 |
| Measles | MMR-II, (Merck) | KLWESPQEI | 36 |
| Chicken Pox | VariVax (Merck) | SLPRSRTPI | 4 |
| | VariVax (Merck) | SAPLPSNRV | 5 |
| Cytomegalovirus | Natural Infection | NLVPMVATV | 3 |
| Human Papilloma virus 16 E7 | Natural Infection | YMLDLQPET | 88 |

Each construct was analyzed by SDS-PAGE as above. (See, FIG. 14). FIG. 14A depicts conjugates of WT HPV VLP to the following peptides: MOVA2 (SIINFEKL (SEQ ID NO: 2), influenza V1, HepB V1, measles V1, and VZV V1. (fusion proteins are synthesized by Genescript, NJ, US, 80% purity as described above). Likewise, FIG. 14B depicts conjugates of RG1 VLPs including MOVA2 (SIINFEKL), influenza V1, HepB V1, measles V1, and VZV V1.

These constructs will be tested in vitro for their ability to localize to tumor cells, bind to tumor cells, have their epitopes proteolytically cleaved, and the released epitope bound by the tumor MHC I receptors to trigger a T cell mediated immune response as in the examples above. Cell lines that are positive for HLA-A2 will be used, as above. Such cell lines include, for example, human tumors such as MDA-MB231, HCT116, and PC-3. In addition, a sub-clone of Murine B16 (Melanoma/Skin), TC-1 (cervical), and ID8 (ovarian) tumor cell subclones were generated that overexpress a luciferase gene and over-express HLA-A2 (B16-AAD, TC 1-AAD, and ID8-AAD, respectively). All of these cell lines can be grown in culture. Under normal circumstances, these cell lines will not be killed by the virus-specific CD8+ T cells specific for the epitopes listed in the table above since these cell lines do not express or display the respective childhood vaccine or natural infection antigen on their cell surface. Cells will be then incubated with: (1) a specific virus antigen peptide from Table 4, above at dosages of 1 µg/ml, 100 pg/ml, and 1 pg/mL; (2) a specific virus antigen conjugated VLP (2.5 µg/mL); (3) an unconjugated (control) VLP; or (4) untreated (with buffer). The cells are then washed and co-cultured with the respective antigen specific T cells at varying E:T ratios (Effector:Target ratio). The cell viability is to be measured either by CELLTITER-GLO® assay for the human tumors or by measuring the expression of luciferase in the murine tumors. Reduced luciferase activity will indicate greater cytotoxicity, suggesting greater immune redirection.

To test this in vivo, naïve transgenic HLA-A2 or HLA-AAD mice are to be vaccinated with childhood vaccines such as HepB, MMR, and chickenpox (see Table 2, above) to generate the pre-existing cytotoxic T lymphocyte (CTL) viral response. CTL responses are to be evaluated using the HLA-A2 specific tetramers to the respective viral peptides. Once sufficient CTL response is confirmed, the mice are then injected with luciferase expressing HLA-A2 positive tumor lines ID8-AAD (ovarian), B16-AAD (melanoma), or TC-1 AAD (cervical) tumor cells. Tumor growth is monitored daily. Once mice develop palpable tumors with average volume of 10 mm³, peptide-conjugated VLP are administered to the tumor-bearing mice at 100 µg/mouse/week and continued for three weeks. The efficacy of anti-tumor immune redirection therapy as described herein using conjugated VLP is measured via tumor volume and survival against the untreated group. In a separate experiment, the same study will be conducted as the above except that the naïve HLA-A2 or HLA-AAD mice will be directly vaccinated with the peptides instead of childhood vaccines.

Example 13

Survival of Mice Treated with Human Tumors after Exposure to Conjugated-VLP

Immunodeficient mice are to be injected with human tumor cells that overexpress MHC class 1 HLA-A2. Examples include: PC-3, HCT112, and MDA-MB231. At the same time, the mice are injected with human Peripheral Blood Mononuclear Cells (PBMC)(10⁶ cells) previously stimulated with a conjugated VLP that is conjugated to a fusion protein comprising one of the following epitopes (Table 5, below):

TABLE 5

Recall Protein Epitopes from Approved Vaccines

| Virus | Approved Human Vaccine where epitope can be detected (Source) | Epitope | SEQ ID NO |
|---|---|---|---|
| Influenza A | Afluria-Trivalent or Flublok Quadrivalent if aged 18-64, Fluzone High-dose OR Fluad if 65 and older, Flucelvax Quadrivalent for 4-18 years old (and older actually) | FMYSDFHFI GILGFVFTL | 77 68 |
| Hepatitis B | Engerix (GSK) | FLPSDFFPSV | 41 |
| Measles | MMR-II, (Merck) | KLWESPQEI | 36 |
| Chicken Pox | VariVax (Merck) | SLPRSRTPI | 4 |
|  | VariVax (Merck) | SAPLPSNRV | 5 |
| Cytomegalovirus | Natural Infection | NLVPMVATV | 3 |
| Human Papilloma virus 16 E7 | Natural Infection | YMLDLQPET | 88 |

The conjugated-VLP comprising a fusion protein containing a recall protein as described above is then injected into the mouse weekly for three weeks. A second injection of human PBMCs stimulated with the conjugated VLP will then be injected into the mouse at day 14. It is expected that tumor formation will be inhibited compared to controls that were not provided the conjugated VLPs.

Example 14

Conjugated VLP Immune Redirection Properties are Dependent on Furin Cleavage

Tumor specificity is in part due to the increased presence of furin on tumor cells. In order to confirm the specificity of conjugated VLPs conjugated to a fusion protein containing a furin cleavage cite, two experiments will be conducted. In the first experiment, a conjugated VLP will be created without a furin cleavage site. A cytotoxic assay will then be conducted to demonstrate that without the furin cleavage site, the peptides cannot be loaded onto the tumor cell. Murine B16 (Melanoma/Skin) and ID8 (ovarian) tumor cells overexpressing luciferase gene (B16-luc and ID8-luc) will be grown in culture. Cells will then be treated with: (1) an E7 peptide (1 µg/ml, 1 ng/ml); (2) HPV16 E7 (lacking the furin cleavage sequence) conjugated VLP (2.5 µg/ml, 0.025 µg/ml); or (3) an unconjugated (control, 2.5 µg/ml) VLP. The cells are then washed and co-cultured with CD8+ HPV16 E7 specific T cells at varying E:T ratios (Effector:Target ratio). The cell viability is then to be measured by detection of luciferase. Reduced luciferase activity indicates greater immune redirection and hence greater cytotoxicity.

In a second experiment, FD11, a furin deficient cell line will be engineered to over-express HLA-A2 MHC Class 1 molecules (FD11/AAD). A cytotoxic assay will then be conducted using this cell line to further demonstrate that without furin, the peptides cannot be loaded onto the tumor cell. FD11/AAD tumor cells overexpressing luciferase gene are to be grown in culture. Cells are then treated with: (1) an E7 peptide (1 µg/ml, 1 ng/ml); (2) HPV16 E7 conjugated VLP (2.5 µg/ml, 0.025 µg/ml); or (3) an unconjugated (control, 2.5 µg/ml) VLP. The cells are then washed and co-cultured with CD8+ HPV16 E7 specific T cells at varying E:T ratios (Effector:Target ratio). The cell viability is measured by measuring the activity/expression of luciferase. Reduced luciferase activity indicated greater immune redirection and hence greater cytotoxicity Example 15

Tumor Re-Challenge Experiments

The ability of mice previously cured of primary tumors by the described conjugated VLP to survive a tumor re-challenge is to be assessed. Mice (n=20) that have survived treatment of a tumor with a conjugated VLP are to be re-challenged with same tumor (1×10$^5$ live cells) four weeks following disappearance of the last tumor. A group of naïve mice (n=20) that have not been exposed to either a tumor or a conjugated VLP are to be injected with the same tumor as a control. Three treated and three naïve mice are then to be sacrificed pre-VLP therapy, post-VLP, and post re-challenge. Tumors and spleen are then prepared for TCRβ high-throughput sequencing by ImmunoSEQ assay (Adaptive Biotechnologies Corp., Seattle, Wash.). Mice previously cured of primary tumors by conjugated VLPs are expected to exhibit resistance to secondary re-challenge, indicating that the conjugated VLP strategy is able to induce a protective system immune response against tumor recurrence. Different TCR clonal profiles of mice at various stages, such as pre-VLP therapy, post-VLP, and post re-challenge will be observed.

What is claimed is:

1. A virus-like particle (VLP), consisting of:
at least one virus capsid protein, and
a fusion protein comprising in order from amino terminus to carboxy terminus as a single peptide:
a) one protease cleavage peptide sequence, attached directly to
b) at least one recall protein comprising at least one epitope,
wherein the at least one virus capsid protein is conjugated to one or more of the fusion protein through a disulfide bond, an ester bond, an amide bond, or a chemical linkage created by exposure of the at least one recall protein and at least one capsid protein simultaneously to a cross-linking agent under conditions amenable to formation of a chemical cross-link,
wherein the fusion protein is 45 amino acids or less in length,
wherein the one protease cleavage peptide sequence is recognized by a tumor microenvironment protease selected from one or more of: cathepsins, kallikreins, serine proteases, caspases, matrix metalloproteinases, disintegrin, and metalloproteinases (ADAMs), and
wherein the at least one epitope is at least one human T cell epitope that is from 8 to 17 amino acids in length.

2. The VLP of claim 1, wherein the at least one epitope:
is a pathogen epitope,
comprises a peptide sequence that complexes with an MHC molecule, and/or
has a sequence selected from one or more of SEQ ID NOS:1 to 83.

3. The VLP of claim 1, wherein the capsid protein is a papilloma virus L1 and/or L2 capsid protein.

4. The VLP of claim 3, wherein the L1 protein is from Bovine papilloma virus (BPV), Human papilloma virus (HPV), Rabbit papilloma virus (RPV), or Mouse papilloma virus (MPV).

5. The VLP of claim 3, wherein the L1 protein is from a bacteriophage or from a plant.

6. The VLP of claim 1, wherein the fusion protein comprises at least two recall proteins.

7. The VLP of claim 1, wherein the at least one capsid protein exhibits tropism for a specific type of tissue.

8. The VLP of claim 7, wherein the tropism is a tropism for cells or tissues expressing heparin sulfate proteoglycan (HSPG).

9. The VLP of claim 1, wherein the capsid protein is from human papilloma virus, hepatitis B virus, bacteriophage MS2, bacteriophage Qβ, bacteriophage P22, cowpea chlorotic mottle virus, cowpea mosaic virus, influenza virus, parvovirus, Norwalk virus, hamster polyoma virus, *Macrobrachium rosenbergii nodavirus*, hepatitis C virus, or a retrovirus.

10. The VLP of claim 1, wherein the epitope sequence is from a childhood vaccine.

11. The VLP of claim 2, wherein the at least one epitope is a viral epitope and is from vaccinia virus, varicella zoster virus, herpes zoster virus, rubella, hepatitis virus, influenza virus, measles virus, mumps virus, poliovirus, variola virus, rabies virus, dengue virus, Ebola virus, West Nile virus, yellow fever virus, zika virus, cytomegalovirus, or Epstein-Barr virus.

12. The VLP of claim 2, wherein the at least one epitope is a bacterial epitope and is from *Bordetella pertussis, Clostridium tetani, Chlamydia trachomatis*, diphtheria, *Hemophilus influenza, Meningococcus, Pneumococcus, Vibrio cholera, Mycobacterium tuberculosis, Bacillus* Calmette-Guérin (BCG), typhoid, *Escherichia coli, Salmonella, Legionella pneumophila, Rickettsia, Treponema pallidum, Streptococcus, Bacillus anthracis, Clostridium botulinum*, or *Yersinia*.

13. The VLP of claim 2, wherein the at least one epitope is a parasitic epitope and is from *Entamoeba histolytica, Toxoplasma gondii, Trichinella, Trichomonas, Trypanosoma*, or *Plasmodium*.

14. The VLP of claim 1, wherein the fusion protein is conjugated to one capsid protein via a cysteine, lysine, or arginine residue.

15. The VLP of claim 14, wherein about 20 to about 100 percent of the cysteine, lysine, and/or arginine residues of the at least one capsid protein are conjugated to the fusion protein.

16. A virus-like particle (VLP), comprising:
at least one virus capsid protein, and
a fusion protein consisting of, in order from amino terminus to carboxy terminus as a single peptide:
a) one protease cleavage peptide sequence, attached to
b) one recall protein comprising at least one epitope,
wherein the fusion protein is 45 amino acids or less in length,
wherein the protease cleavage peptide sequence is recognized by a tumor microenvironment protease selected from one or more of: cathepsins, kallikreins, serine proteases, caspases, matrix metalloproteinases, disintegrin and metalloproteinases (ADAMs),
wherein the at least one epitope is from 8 to 17 amino acids in length, and
wherein the at least one capsid protein exhibits tropism for a specific type of tissue.

17. The VLP of claim 16, wherein the at least one epitope is a viral epitope from vaccinia virus, varicella zoster virus, herpes zoster virus, rubella, hepatitis virus, influenza virus, measles virus, mumps virus, poliovirus, variola virus, rabies virus, dengue virus, Ebola virus, West Nile virus, yellow fever virus, zika virus, cytomegalovirus, or Epstein-Barr virus.

18. The VLP of claim 1, wherein the at least one epitope is heterologous to the at least one virus capsid protein.

19. The VLP of claim 16, wherein the at least one epitope is heterologous to the at least one virus capsid protein.

\* \* \* \* \*

SEQUENCE LISTING

```
<160> NUMBER OF SEQ ID NOS: 90

<210> SEQ ID NO 1
<211> LENGTH: 9
<212> TYPE: PRT
<213> ORGANISM: Human papillomavirus type 16

<400> SEQUENCE: 1

Arg Ala His Tyr Asn Ile Val Thr Phe
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic: fluorophore-conjugated anti-OVA

<400> SEQUENCE: 2

Ser Ile Ile Asn Phe Glu Lys Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic: CMV peptide

<400> SEQUENCE: 3

Asn Leu Val Pro Met Val Ala Thr Val
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 4

Ser Leu Pro Arg Ser Arg Thr Pro Ile
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 5
```

Ser Ala Pro Leu Pro Ser Asn Arg Val
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic: recall protein epitope

<400> SEQUENCE: 6

Gly Ser Ala Pro Leu Pro Ser Asn Arg Val
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 7

Ala Leu Trp Ala Leu Pro His Ala Ala
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 8

Ser Leu Ser Gly Leu Tyr Val Phe Val
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 9

Tyr Leu Gly Val Tyr Ile Trp Asn Met
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 10

Lys Ile His Glu Ala Pro Phe Asp Leu
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 11

```
Leu Leu Cys Leu Val Ile Phe Leu Ile
1               5
```

<210> SEQ ID NO 12
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 12

```
Asp Leu Leu Leu Glu Trp Leu Tyr Val
1               5
```

<210> SEQ ID NO 13
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 13

```
Ser Met Tyr Tyr Ala Gly Leu Pro Val
1               5
```

<210> SEQ ID NO 14
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 14

```
Ile Leu His Asp Gly Gly Thr Thr Leu
1               5
```

<210> SEQ ID NO 15
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 15

```
Trp Leu Tyr Val Pro Ile Asp Pro Thr
1               5
```

<210> SEQ ID NO 16
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 16

```
Val Leu Met Gly Phe Gly Ile Ile Thr
1               5
```

<210> SEQ ID NO 17
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 17

```
Cys Leu Val Ile Phe Leu Ile Cys Thr
```

```
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 18

Lys Glu Ala Asp Gln Pro Trp Ile Val
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 19

Val Val Ser Thr Val Asp His Phe Val
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 20

Phe Leu Ile Cys Thr Ala Lys Arg Met
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 21

Val Leu Arg Thr Glu Lys Gln Tyr Leu
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 22

His Met Trp Asn Tyr His Ser His Val
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 23

Thr Val Asn Lys Pro Val Val Gly Val
1               5
```

```
<210> SEQ ID NO 24
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 24

Phe Val Val Tyr Phe Asn Gly His Val
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 25

Trp Ile Val Val Asn Thr Ser Thr Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 26

Val Ala Tyr Thr Val Val Ser Thr Val
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 27

Phe Met Tyr Met Ser Leu Leu Gly Val
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 28

Ser Leu Trp Gly Ser Leu Leu Met Leu
1               5

<210> SEQ ID NO 29
<211> LENGTH: 10
<212> TYPE: PRT
<213> ORGANISM: Artificial Sequence
<220> FEATURE:
<223> OTHER INFORMATION: Synthetic: recall protein epitope

<400> SEQUENCE: 29

Leu Leu Ala Val Ile Phe Val Met Phe Leu
1               5                   10
```

<210> SEQ ID NO 30
<211> LENGTH: 10
<212> TYPE: PRT
<213> ORGANISM: Artificial Sequence
<220> FEATURE:
<223> OTHER INFORMATION: Synthetic: recall protein epitope

<400> SEQUENCE: 30

Ser Met Tyr Arg Val Phe Glu Val Gly Val
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic: recall protein epitope

<400> SEQUENCE: 31

Ile Leu Pro Gly Gln Asp Leu Gln Tyr Val
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 32

Lys Leu Trp Cys Arg His Phe Cys Val
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic: recall protein epitope

<400> SEQUENCE: 33

Lys Leu Trp Cys Arg His Phe Cys Val Leu
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic: recall protein epitope

<400> SEQUENCE: 34

Arg Leu Ser Asp Asn Gly Tyr Tyr Thr Val
1               5                   10

<210> SEQ ID NO 35
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 35

Lys Leu Leu Arg Tyr Tyr Thr Glu Ile
1               5

```
<210> SEQ ID NO 36
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 36

Lys Leu Trp Glu Ser Pro Gln Glu Ile
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 37

Arg Leu Leu Asp Arg Leu Val Arg Leu
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 38

Lys Leu Met Pro Asn Ile Thr Leu Leu
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 39

Thr Leu Leu Asn Asn Cys Thr Arg Val
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 40

Glu Met Leu Thr Leu Ala Thr Trp Val
1               5

<210> SEQ ID NO 41
<211> LENGTH: 10
<212> TYPE: PRT
<213> ORGANISM: Artificial Sequence
<220> FEATURE:
<223> OTHER INFORMATION: Synthetic: recall protein epitope

<400> SEQUENCE: 41

Phe Leu Pro Ser Asp Phe Phe Pro Ser Val
1               5                   10

<210> SEQ ID NO 42
```

```
<211> LENGTH: 10
<212> TYPE: PRT
<213> ORGANISM: Artificial Sequence
<220> FEATURE:
<223> OTHER INFORMATION: Synthetic: recall protein epitope

<400> SEQUENCE: 42

Phe Leu Pro Ala Asp Phe Phe Pro Ser Val
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic: recall protein epitope

<400> SEQUENCE: 43

Phe Leu Pro Ser Asp Phe Phe Pro Ser Ile
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Synthetic: recall protein epitope

<400> SEQUENCE: 44

Trp Leu Ser Leu Leu Val Pro Phe
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 45

Phe Leu Leu Thr Arg Ile Leu Thr Ile
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 46

Phe Leu Leu Thr Arg Ile Leu Thr Leu
1               5

<210> SEQ ID NO 47
<211> LENGTH: 10
<212> TYPE: PRT
<213> ORGANISM: Artificial Sequence
<220> FEATURE:
<223> OTHER INFORMATION: Synthetic: recall protein epitope

<400> SEQUENCE: 47

Gly Leu Ser Pro Thr Val Trp Leu Ser Val
1               5                   10

<210> SEQ ID NO 48
<211> LENGTH: 10
```

```
<212> TYPE: PRT
<213> ORGANISM: Artificial Sequence
<220> FEATURE:
<223> OTHER INFORMATION: Synthetic: recall protein epitope

<400> SEQUENCE: 48

Leu Leu Asp Tyr Gln Gly Met Leu Pro Val
1               5                   10

<210> SEQ ID NO 49
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 49

Leu Leu Cys Leu Ile Phe Leu Leu Val
1               5

<210> SEQ ID NO 50
<211> LENGTH: 10
<212> TYPE: PRT
<213> ORGANISM: Artificial Sequence
<220> FEATURE:
<223> OTHER INFORMATION: Synthetic: recall protein epitope

<400> SEQUENCE: 50

Ser Ile Val Ser Pro Phe Ile Pro Leu Leu
1               5                   10

<210> SEQ ID NO 51
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 51

Phe Leu Leu Thr Lys Ile Leu Thr Ile
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 52

Ile Leu Ser Pro Phe Leu Pro Leu Leu
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 53

Phe Leu Leu Ser Leu Gly Ile His Leu
1               5

<210> SEQ ID NO 54
<211> LENGTH: 9
<212> TYPE: PRT
```

```
<213> ORGANISM: Artificial Sequence
<220> FEATURE:
<223> OTHER INFORMATION: Synthetic: recall protein epitope

<400> SEQUENCE: 54

Gly Leu Ser Arg Tyr Val Ala Arg Leu
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 55

Ser Leu Tyr Ala Asp Ser Pro Ser Val
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 56

Tyr Met Asp Asp Val Val Leu Gly Ala
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 57

Ala Leu Met Pro Leu Tyr Ala Cys Ile
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 58

Val Leu His Lys Arg Thr Leu Gly Leu
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 59

Cys Leu Phe Lys Asp Trp Glu Glu Leu
1               5

<210> SEQ ID NO 60
<211> LENGTH: 11
<212> TYPE: PRT
<213> ORGANISM: Artificial Sequence
```

```
<220> FEATURE:
<223> OTHER INFORMATION: Synthetic: recall protein epitope

<400> SEQUENCE: 60

Ser Thr Leu Pro Glu Thr Thr Val Val Arg Arg
1               5                   10

<210> SEQ ID NO 61
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 61

Glu Tyr Leu Val Ser Phe Gly Val Trp
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 62

Phe Phe Pro Ser Ile Arg Asp Leu Leu
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 63

Ser Trp Leu Ser Leu Leu Val Pro Phe
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 64

Lys Tyr Thr Ser Phe Pro Trp Leu Leu
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 65

His Leu Ser Leu Arg Gly Leu Phe Val
1               5

<210> SEQ ID NO 66
<211> LENGTH: 9
<212> TYPE: PRT
<213> ORGANISM: Artificial Sequence
<220> FEATURE:
```

<223> OTHER INFORMATION: Synthetic: recall protein epitope

<400> SEQUENCE: 66

Cys Leu Phe Lys Asp Trp Glu Glu Leu
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 67

Leu Pro Ser Asp Phe Phe Pro Ser Val
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 68

Gly Ile Leu Gly Phe Val Phe Thr Leu
1               5

<210> SEQ ID NO 69
<211> LENGTH: 21
<212> TYPE: PRT
<213> ORGANISM: Artificial Sequence
<220> FEATURE:
<223> OTHER INFORMATION: Synthetic: recall protein epitope

<400> SEQUENCE: 69

Ile Leu Gly Phe Val Phe Thr Leu Thr Val Pro Ser Glu Arg Gly Leu
1               5                   10                  15

Gln Arg Arg Arg Phe
            20

<210> SEQ ID NO 70
<211> LENGTH: 17
<212> TYPE: PRT
<213> ORGANISM: Artificial Sequence
<220> FEATURE:
<223> OTHER INFORMATION: Synthetic: recall protein epitope

<400> SEQUENCE: 70

Leu Ile Arg His Glu Asn Arg Met Val Leu Ala Ser Thr Thr Ala Lys
1               5                   10                  15

Ala

<210> SEQ ID NO 71
<211> LENGTH: 14
<212> TYPE: PRT
<213> ORGANISM: Artificial Sequence
<220> FEATURE:
<223> OTHER INFORMATION: Synthetic: recall protein epitope

<400> SEQUENCE: 71

Leu Gln Ala Tyr Gln Lys Arg Met Gly Val Gln Met Gln Arg
1               5                   10

<210> SEQ ID NO 72

```
<211> LENGTH: 11
<212> TYPE: PRT
<213> ORGANISM: Artificial Sequence
<220> FEATURE:
<223> OTHER INFORMATION: Synthetic: recall protein epitope

<400> SEQUENCE: 72

Tyr Val Tyr Asp His Ser Gly Glu Ala Val Lys
1               5                   10

<210> SEQ ID NO 73
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 73

Trp Leu Ser Leu Leu Val Pro Phe Val
1               5

<210> SEQ ID NO 74
<211> LENGTH: 12
<212> TYPE: PRT
<213> ORGANISM: Artificial Sequence
<220> FEATURE:
<223> OTHER INFORMATION: Synthetic: recall protein epitope
<220> FEATURE:
<221> NAME/KEY: misc_feature
<222> LOCATION: (1)..(1)
<223> OTHER INFORMATION: Lys may or may not be present
<220> FEATURE:
<221> NAME/KEY: misc_feature
<222> LOCATION: (11)..(12)
<223> OTHER INFORMATION: Thr or Val may or may not be present

<400> SEQUENCE: 74

Lys Gly Ile Leu Gly Phe Val Phe Thr Leu Thr Val
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Synthetic: recall protein epitope

<400> SEQUENCE: 75

Lys Leu Ser Thr Arg Gly Val Gln Ile Ala Ser Asn Glu Asn
1               5                   10

<210> SEQ ID NO 76
<211> LENGTH: 17
<212> TYPE: PRT
<213> ORGANISM: Artificial Sequence
<220> FEATURE:
<223> OTHER INFORMATION: Synthetic: recall protein epitope

<400> SEQUENCE: 76

Arg Gly Leu Gln Arg Arg Arg Phe Val Gln Asn Ala Leu Asn Gly Asn
1               5                   10                  15

Gly

<210> SEQ ID NO 77
<211> LENGTH: 9
<212> TYPE: PRT
<213> ORGANISM: Artificial Sequence
<220> FEATURE:
```

```
<223> OTHER INFORMATION: Synthetic: recall protein epitope

<400> SEQUENCE: 77

Phe Met Tyr Ser Asp Phe His Phe Ile
1               5

<210> SEQ ID NO 78
<211> LENGTH: 18
<212> TYPE: PRT
<213> ORGANISM: Artificial Sequence
<220> FEATURE:
<223> OTHER INFORMATION: Synthetic: recall protein epitope

<400> SEQUENCE: 78

Val Ala Ile Ile Glu Val Asp Asn Glu Gln Pro Thr Thr Arg Ala Gln
1               5                   10                  15

Lys Leu

<210> SEQ ID NO 79
<211> LENGTH: 39
<212> TYPE: PRT
<213> ORGANISM: Artificial Sequence
<220> FEATURE:
<223> OTHER INFORMATION: Synthetic: recall protein epitope

<400> SEQUENCE: 79

Gly Ala Cys Val Ala Ile Ile Glu Val Asp Asn Glu Gln Pro Thr Thr
1               5                   10                  15

Arg Ala Gln Lys Leu Phe Ala Met Trp Arg Ile Thr Tyr Lys Asp Thr
            20                  25                  30

Val Gln Leu Arg Arg Lys Leu
        35

<210> SEQ ID NO 80
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 80

Ser Val Arg Asp Arg Leu Ala Arg Leu
1               5

<210> SEQ ID NO 81
<211> LENGTH: 10
<212> TYPE: PRT
<213> ORGANISM: Artificial Sequence
<220> FEATURE:
<223> OTHER INFORMATION: Synthetic: recall protein epitope

<400> SEQUENCE: 81

Leu Leu Asp Arg Val Arg Phe Met Gly Val
1               5                   10

<210> SEQ ID NO 82
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 82

Cys Leu Gly Gly Leu Leu Thr Met Val
1               5
```

```
<210> SEQ ID NO 83
<211> LENGTH: 9
<212> TYPE: PRT
<213> ORGANISM: Artificial Sequence
<220> FEATURE:
<223> OTHER INFORMATION: Synthetic: recall protein epitope

<400> SEQUENCE: 83

Gly Leu Cys Thr Leu Val Ala Met Leu
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic: peptide

<400> SEQUENCE: 84

Glu Glu Glu Glu Glu Glu Glu Glu Cys
1               5

<210> SEQ ID NO 85
<211> LENGTH: 10
<212> TYPE: PRT
<213> ORGANISM: Artificial Sequence
<220> FEATURE:
<223> OTHER INFORMATION: Synthetic: peptide

<400> SEQUENCE: 85

Cys Glu Glu Glu Glu Glu Glu Glu Glu Cys
1               5                   10

<210> SEQ ID NO 86
<211> LENGTH: 505
<212> TYPE: PRT
<213> ORGANISM: Human papillomavirus type 16

<400> SEQUENCE: 86

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
```

```
                    165                 170                 175
Asn Val Ala Val Asn Pro Gly Asp Cys Pro Leu Glu Leu Ile Asn
                180                 185                 190
Thr Val Ile Gln Asp Gly Asp Met Val Asp Thr Gly Phe Gly Ala Met
            195                 200                 205
Asp Phe Thr Thr Leu Gln Ala Asn Lys Ser Glu Val Pro Leu Asp Ile
210                 215                 220
Cys Thr Ser Ile Cys Lys Tyr Pro Asp Tyr Ile Lys Met Val Ser Glu
225                 230                 235                 240
Pro Tyr Gly Asp Ser Leu Phe Phe Tyr Leu Arg Arg Glu Gln Met Phe
                245                 250                 255
Val Arg His Leu Phe Asn Arg Ala Gly Thr Val Gly Glu Asn Val Pro
            260                 265                 270
Asp Asp Leu Tyr Ile Lys Gly Ser Gly Ser Thr Ala Asn Leu Ala Ser
        275                 280                 285
Ser Asn Tyr Phe Pro Thr Pro Ser Gly Ser Met Val Thr Ser Asp Ala
    290                 295                 300
Gln Ile Phe Asn Lys Pro Tyr Trp Leu Gln Arg Ala Gln Gly His Asn
305                 310                 315                 320
Asn Gly Ile Cys Trp Gly Asn Gln Leu Phe Val Thr Val Val Asp Thr
                325                 330                 335
Thr Arg Ser Thr Asn Met Ser Leu Cys Ala Ala Ile Ser Thr Ser Glu
            340                 345                 350
Thr Thr Tyr Lys Asn Thr Asn Phe Lys Glu Tyr Leu Arg His Gly Glu
        355                 360                 365
Glu Tyr Asp Leu Gln Phe Ile Phe Gln Leu Cys Lys Ile Thr Leu Thr
    370                 375                 380
Ala Asp Val Met Thr Tyr Ile His Ser Met Asn Ser Thr Ile Leu Glu
385                 390                 395                 400
Asp Trp Asn Phe Gly Leu Gln Pro Pro Gly Gly Thr Leu Glu Asp
                405                 410                 415
Thr Tyr Arg Phe Val Thr Ser Gln Ala Ile Ala Cys Gln Lys His Thr
            420                 425                 430
Pro Pro Ala Pro Lys Glu Asp Pro Leu Lys Lys Tyr Thr Phe Trp Glu
        435                 440                 445
Val Asn Leu Lys Glu Lys Phe Ser Ala Asp Leu Asp Gln Phe Pro Leu
    450                 455                 460
Gly Arg Lys Phe Leu Leu Gln Ala Gly Leu Lys Ala Lys Pro Lys Phe
465                 470                 475                 480
Thr Leu Gly Lys Arg Lys Ala Thr Pro Thr Thr Ser Ser Thr Ser Thr
                485                 490                 495
Thr Ala Lys Arg Lys Lys Arg Lys Leu
            500                 505

<210> SEQ ID NO 87
<211> LENGTH: 527
<212> TYPE: PRT
<213> ORGANISM: Artificial Sequence
<220> FEATURE:
<223> OTHER INFORMATION: Synthetic: RG1 VLP L1 peptide sequence

<400> SEQUENCE: 87

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
```

-continued

```
                20                  25                  30
Ile Tyr Tyr His Ala Gly Thr Ser Arg Leu Leu Ala Val Gly His Pro
             35                  40                  45
Tyr Phe Pro Ile Lys Lys Pro Asn Asn Asn Lys Ile Leu Val Pro Lys
         50                  55                  60
Val Ser Gly Leu Gln Tyr Arg Val Phe Arg Ile His Leu Pro Asp Pro
 65                  70                  75                  80
Asn Lys Phe Gly Phe Pro Asp Thr Ser Phe Tyr Asn Pro Asp Thr Gln
                 85                  90                  95
Arg Leu Val Trp Ala Cys Val Gly Val Glu Val Gly Arg Gly Gln Pro
                100                 105                 110
Leu Gly Val Gly Ile Ser Gly His Pro Leu Leu Asn Lys Leu Asp Asp
            115                 120                 125
Thr Glu Asn Ala Ser Ala Tyr Ala Gln Leu Tyr Lys Thr Cys Lys Gln
        130                 135                 140
Ala Gly Thr Cys Pro Pro Asp Ile Ile Pro Lys Val Ala Asn Ala Gly
145                 150                 155                 160
Val Asp Asn Arg Glu Cys Ile Ser Met Asp Tyr Lys Gln Thr Gln Leu
                165                 170                 175
Cys Leu Ile Gly Cys Lys Pro Pro Ile Gly Glu His Trp Gly Lys Gly
            180                 185                 190
Ser Pro Cys Thr Asn Val Ala Val Asn Pro Gly Asp Cys Pro Pro Leu
        195                 200                 205
Glu Leu Ile Asn Thr Val Ile Gln Asp Gly Asp Met Val Asp Thr Gly
    210                 215                 220
Phe Gly Ala Met Asp Phe Thr Thr Leu Gln Ala Asn Lys Ser Glu Val
225                 230                 235                 240
Pro Leu Asp Ile Cys Thr Ser Ile Cys Lys Tyr Pro Asp Tyr Ile Lys
                245                 250                 255
Met Val Ser Glu Pro Tyr Gly Asp Ser Leu Phe Phe Tyr Leu Arg Arg
            260                 265                 270
Glu Gln Met Phe Val Arg His Leu Phe Asn Arg Ala Gly Ala Val Gly
        275                 280                 285
Glu Asn Val Pro Asp Asp Leu Tyr Ile Lys Gly Ser Gly Ser Thr Ala
    290                 295                 300
Asn Leu Ala Ser Ser Asn Tyr Phe Pro Thr Pro Ser Gly Ser Met Val
305                 310                 315                 320
Thr Ser Asp Ala Gln Ile Phe Asn Lys Pro Tyr Trp Leu Gln Arg Ala
                325                 330                 335
Gln Gly His Asn Asn Gly Ile Cys Trp Gly Asn Gln Leu Phe Val Thr
            340                 345                 350
Val Val Asp Thr Thr Arg Ser Thr Asn Met Ser Leu Cys Ala Ala Ile
        355                 360                 365
Ser Thr Ser Glu Thr Thr Tyr Lys Asn Thr Asn Phe Lys Glu Tyr Leu
    370                 375                 380
Arg His Gly Glu Glu Tyr Asp Leu Gln Phe Ile Phe Gln Leu Cys Lys
385                 390                 395                 400
Ile Thr Leu Thr Ala Asp Val Met Thr Tyr Ile His Ser Met Asn Ser
                405                 410                 415
Thr Ile Leu Glu Asp Trp Asn Phe Gly Leu Gln Pro Pro Pro Gly Gly
            420                 425                 430
Thr Leu Glu Asp Thr Tyr Arg Phe Val Thr Ser Gln Ala Ile Ala Cys
        435                 440                 445
```

```
Gln Lys His Thr Pro Pro Ala Pro Lys Glu Asp Pro Leu Lys Lys Tyr
        450                 455                 460
Thr Phe Trp Glu Val Asn Leu Lys Glu Lys Phe Ser Ala Asp Leu Asp
465                 470                 475                 480
Gln Phe Pro Leu Gly Arg Lys Phe Leu Leu Gln Ala Gly Leu Lys Ala
                485                 490                 495
Lys Pro Lys Phe Thr Leu Gly Lys Arg Lys Ala Thr Pro Thr Thr Ser
            500                 505                 510
Ser Thr Ser Thr Thr Ala Lys Arg Lys Lys Arg Lys Leu Ser Arg
            515                 520                 525

<210> SEQ ID NO 88
<211> LENGTH: 9
<212> TYPE: PRT
<213> ORGANISM: Artificial Sequence
<220> FEATURE:
<223> OTHER INFORMATION: Synthetic: epitope

<400> SEQUENCE: 88

Tyr Met Leu Asp Leu Gln Pro Glu Thr
1               5

<210> SEQ ID NO 89
<211> LENGTH: 4
<212> TYPE: PRT
<213> ORGANISM: Artificial Sequence
<220> FEATURE:
<223> OTHER INFORMATION: Synthetic: furin cleavage sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: X is R or K

<400> SEQUENCE: 89

Arg Xaa Xaa Arg
1

<210> SEQ ID NO 90
<211> LENGTH: 4
<212> TYPE: PRT
<213> ORGANISM: Artificial Sequence
<220> FEATURE:
<223> OTHER INFORMATION: Synthetic: furin cleavage sequence

<400> SEQUENCE: 90

Arg Val Lys Arg
1
```